US012760318B2

(12) United States Patent
O'Connor

(10) Patent No.: US 12,760,318 B2
(45) Date of Patent: Oct. 13, 2026

(54) METHODS AND COMPOSITIONS FOR CONTROLLING MERISTEM SIZE FOR CROP IMPROVEMENT

(71) Applicant: Pairwise Plants Services, Inc., Durham, NC (US)

(72) Inventor: Devin Lee O'Connor, Hillsborough, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 389 days.

(21) Appl. No.: 18/342,767

(22) Filed: Jun. 28, 2023

(65) Prior Publication Data

US 2024/0002873 A1 Jan. 4, 2024

Related U.S. Application Data

(60) Provisional application No. 63/356,527, filed on Jun. 29, 2022.

(51) Int. Cl.

| | |
|---|---|
| ***C12N 15/82*** | (2006.01) |
| ***C07K 14/415*** | (2006.01) |
| ***C12N 9/22*** | (2006.01) |
| ***C12N 15/11*** | (2006.01) |

(52) U.S. Cl.

CPC ........ *C12N 15/8262* (2013.01); *C07K 14/415* (2013.01); *C12N 9/22* (2013.01); *C12N 15/11* (2013.01); *C12N 15/8213* (2013.01); *C12N 2310/20* (2017.05); *C12N 2800/80* (2013.01)

(58) Field of Classification Search

None

See application file for complete search history.

(56) References Cited

U.S. PATENT DOCUMENTS

| | | | | |
|---|---|---|---|---|
| 10,876,129 | B2 | 12/2020 | Pennell et al. | |
| 11,999,946 | B2 | 6/2024 | Karlson et al. | |
| 2019/0032071 | A1* | 1/2019 | Pennell | C12N 15/8247 |
| 2020/0377900 | A1* | 12/2020 | Cargill | C12N 15/8216 |
| 2021/0301282 | A1* | 9/2021 | Karlson | C12N 9/22 |
| 2021/0371873 | A1* | 12/2021 | O'Connor | A01H 6/4684 |
| 2024/0000031 | A1 | 1/2024 | O'Connor | |
| 2024/0279640 | A1 | 8/2024 | Karlson et al. | |
| 2024/0301400 | A1 | 9/2024 | Karlson et al. | |

FOREIGN PATENT DOCUMENTS

| | | | | |
|---|---|---|---|---|
| CN | 103088054 | A | 5/2013 | |
| CN | 108192912 | A | 6/2018 | |
| WO | 0170987 | A2 | 9/2001 | |
| WO | 03093450 | A2 | 11/2003 | |
| WO | 2008062049 | A1 | 5/2008 | |
| WO | 2013138544 | A1 | 9/2013 | |
| WO | 2017139309 | A1 | 8/2017 | |
| WO | WO-2018213547 | A1 * | 11/2018 | C12N 15/8213 |
| WO | 2020023258 | A1 | 1/2020 | |
| WO | 2021195458 | A1 | 9/2021 | |

OTHER PUBLICATIONS

Bommert et al. ("Quantitative variation in maize kernel row number is controlled by the Fasciated EAR2 locus" 2013 Nature Genetics 45(3):334-338. (Year: 2013).*

Taguchi-Shiobara et al. "The fascinated ear2 gene encodes a leucine-rich repeat receptor-like protein that regulates shoot meristem proliferation in maize" 2001 Genes & Development 15:2755-2766. (Year: 2001).*

Bommert et al. ("Quantitative variation in maize kernel row number is controlled by the Fasciated EAR2 locus" 2013 Nature Genetics 45(3):334-338 including supplemental information available at https://www.nature.com/articles/ng.2534). (Year: 2013).*

FEA2_MAIZE, version 102, UniProtKB Accession No. Q940E8 (B4G061); dated Feb. 13, 2019.

International Search Report and Written Opinion corresponding to International Application No. PCT/US2021/024283; dated Jul. 16, 2021, 13 pages.

International Search Report and Written Opinion corresponding to International Application No. PCT/US2021/027609 dated Sep. 28, 2021, 22 pages.

International Search Report and Written Opinion corresponding to International Application No. PCT/US2021/035114, mailed Sep. 21, 2021, 14 pages.

International Search Report and Written Opinion corresponding to International Application No. PCT/US2021/037740, mailed Dec. 2, 2021, 22 pages.

International Search Report and Written Opinion corresponding to International Application No. PCT/US2023/069210, mailed Oct. 16, 2023, 21 pages.

International Search Report and Written Opinion corresponding to International Application No. PCT/US2023/069211, mailed Oct. 16, 2023, 21 pages.

Leucine-rich repeat receptor-like protein fasciatef ear2, Uniprot Database Accession No. Q940E8 (Dec. 1, 2001).

Receptor-like protein kinase 5 [*Zea mays*], EMBL/GenBank Accession No. ONM34918.1 (2017).

Database: UniProt [online]: A0A5J9V4K0_9POAL. Protein Recommended Name: Protein kinase domain-containing protein, Dec. 11, 2019. Retrieved from: https://www.uniprot.org/uniprot/A0A5J9V4K0, 2 pages.

Fon2-like cle protein1 [*Zea mays*], Retrieved from https://www.ncbi.nlm.nih.gov/protein/ONM16738.1?report=genbank&log$=protalign&blast_rank=1&RID=BF2FPXGG013 on Jul. 19, 2023, 2023.

(Continued)

*Primary Examiner* — Amjad Abraham
*Assistant Examiner* — Rebecca Stephens
(74) *Attorney, Agent, or Firm* — Myers Bigel, P.A.

(57) ABSTRACT

This invention relates to compositions and methods for modifying FASCIATED EAR2 (FEA2) genes in plants, optionally to modify meristem size. The invention further relates to plants having increased kernel row number produced using the methods and compositions of the invention.

8 Claims, No Drawings

Specification includes a Sequence Listing.

(56) References Cited

OTHER PUBLICATIONS

Hypothetical protein ZEAMMB73_Zm00001d007576 [*Zea mays*], Retrieved from https://www.ncbi.nlm.nih.gov/protein/ONM27114.1?report=genbank&log$=protalign&blast_rank=1&RID=BHMXAB2Y016 on Jul. 20, 2023, 2023.
*Zea mays* clone 462207 mRNA sequence, Retrieved from https://www.ncbi.nlm.nih.gov/nucleotide/EU974983.1?report=genbank&log$=nuclalign&blast_rank=2&RID=BF1RUX1A013 on Jul. 19, 2023, 2023.
Bettembourg, Mathilde , et al., "Root cone angle is enlarged in docs1 LRR-RLK mutants in rice", Rice, 10(1), 2017, 1-8.
Bleckmann , et al., "Stem Cell Signaling in *Arabidopsis* Requires CRN to Localize CLV2 to the Plasma Membrane", Plant Physiology, 152:166-176 2010.
Bommert, Peter , et al., "Quantitative variation in maize kernel row number is controlled by the Fasciated EAR2 locus", Nature Genetics 45(3), 2013, 334-337.
Bommert, Peter , et al., "Thick tassel dwarf1 encodes a putative maize ortholog of the *Arabidopsis* Clavata1 leucine-rich repeat receptor-like kinase", Development, 132(6), 2005, 1235-1245.
Carballo, Jose , et al., "A high-quality genome of Eragrostis curvula grass provides insights into Poaceae evolution and supports new strategies to enhance forage quality", Scientific Reports, 9(Article: 10250), 2019, 1-15.
Crook, Ashley D., et al., "The systemic nodule number regulation kinase SUNN in Medicago truncatula interacts with MtCLV2 and MtCRN", The Plant Journal 88, 2016, 108-119.
Czyzewicz, Nathan , et al., "Antagonistic peptide technology for functional dissection of CLE peptides revisited", Journal of Experimental Botany 66, 2015, 5367-5374.
Deyoung, Brody J., et al., "The Clavata1-related BAM1, BAM2 and BAM3 receptor kinase-like proteins are required for meristem function in *Arabidopsis*", The Plant Journal, 45(1), 2006, 1-16.
Diévart, Anne , et al., "Clavata1 Dominant-Negative Alleles Reveal Functional Overlap between Multiple Receptor Kinases That Regulate Meristem and Organ Development", The Plant Cell, 15(5), 2003, 1198-1211.
Ellison, Erika L., et al., "Mutator transposon insertions within maize genes often provide a novel outward reading promoter", bioRxiv. https://doi.org/10.1101/2023.06.05.543741, 2023, 1-33.
Fan, C. , et al., "A Novel Single-Nucleotide Mutation in a Clavata3 Gene Homolog Controls a Multilocular Silique Trait in *Brassica rapa* L", Mol Plant 7, 2014, 1788-1792.
Fletcher, Jennifer C., "The CLV-WUS Stem Cell Signaling Pathway: A Roadmap to Crop Yield Optimization", Plants 7(4), 2018, 1-11.
Goad, David M., et al., "Comprehensive identification and clustering of CLV3/ESR-related (CLE) genes in plants finds groups with potentially shared function", New Phytologist 216, 2017, 605-616.
Guo, Y. , et al., "Clavata2 forms a distinct CLE-binding receptor complex regulating *Arabidopsis* stem cell specification", Plant J 63: 889-900, 2010.
Hu, Chong , et al., "A group of receptor kinases are essential for Clavata signalling to maintain stem cell homeostasis", Nature Plants, 4, 2018, 205-211.
Je, Byoung Il , et al., "Signaling from maize organ primordia via Fasciated EAR3 regulates stem cell proliferation and yield traits", Nature Genetics 48, 2016, 785-791.
Je, B. , et al., "The Clavata receptor Fasciated EAR2 responds to distinct CLE peptides by signaling through two downstream effectors", eLife 7: e35673.
Kinoshita, Atsuko , et al., "RPK2 is an essential receptor-like kinase that transmits the CLV3 signal in *Arabidopsis*", Development, 137(22), 2010, 3911-3920.
Laux, Thomas , et al., "The Wuschel gene is required for shoot and floral meristem integrity in *Arabidopsis*", Development (Cambridge, England) 122, 1996, 87-96.
Li, Manfei , et al., "Genetic and Molecular Mechanisms of Quantitative Trait Loci Controlling Maize Inflorescence Architecture", 2018 Plant Cell Physiology 59 (3), 2018, 448-457.
Liu, Lei , et al., "Enhancing grain-yield-related traits by CRISPR-Cas9 promoter editing of maize CLE genes", Nature plants, 7(3), 2021, 287-294.
Liu, Chang , et al., "Natural variation in the Thick Tassel Dwarf1 (TD1) gene in the regulation of maize (*Zea mays* L.) ear-related traits", Breeding Science, 69(2), 2019, 323-331.
Miwa, H. , "The Receptor-Like Kinase SOL2 Mediates CLE Signaling in *Arabidopsis*", Plant Cell Physiol 49: 1752-1757, 2008.
Muller, R. , et al., "The Receptor Kinase Coryne of *Arabidopsis* Transmits the Stem Cell-Limiting Signal Clavata3 Independently of Clavata1", The Plant Cell Online 20: 934-946, 2008.
Nimchuk, Z.L. , et al., "An Evolutionarily Conserved Pseudokinase Mediates Stem Cell Production in Plants", Plant Cell 23: 851-854, 2011.
Nimchuk, Zachary L., et al., "Plant stem cell maintenance by transcriptional cross-regulation of related receptor kinases", Development, 142(6), 2015, 1043-1049.
Nowak, Stephen , et al., "The Medicago truncatula Clavata3-Like CLE12/13 signaling peptides regulate nodule number depending on the Coryne but not the Compact Root Architecture2 receptor", Plant Signaling & Behavior. vol. 14, No. 6, 2019, e1598730.
Rodriguez-Leal, Daniel , et al., "Evolution of buffering in a genetic circuit controlling plant stem cell proliferation", Nature Genetics. 51, 2019, 786-792.
Rodriguez-Villalon, Antia , et al., "Molecular genetic framework for protophloem formation", Proceedings of the National Academy of Sciences 111, 2014, 11551-11556.
Schoof, Heiko , et al., "The Stem Cell Population of *Arabidopsis* Shoot Meristems Is Maintained by a Regulatory Loop between the Clavata and Wuschel Genes", Cell 100(6), 2000, 635-644.
Shpak, Elena D., et al., "Dominant-Negative Receptor Uncovers Redundancy in the *Arabidopsis* Erecta Leucine-Rich Repeat Receptor-Like Kinase Signaling Pathway That Regulates Organ Shape", The Plant Cell, 15(5), 2003, 1095-1110.
Somssich, Marc , "On Receptor Kinase Interactions and Complex Formations", Inaugural dissertation zur Erlangung des Doktorgrades der Mathematisch-Naturwissenschaftlichen Fakultat der Heinrich-Heine-Universitat D0sseldorf vorgelegt van Nov. 18, 2014 Dissertation.
Somssich, Marc , et al., "Shared and distinct functions of the pseudokinase Coryne (CRN) in shoot and root stem cell maintenance of *Arabidopsis*", Journal of Experimental Botany, vol. 67, No. 16, 20116, 4901-4915.
Song, Xiu-Fen , et al., "Antagonistic Peptide Technology for Functional Dissection of CLV3/ESR Genes in *Arabidopsis*", Plant Physiol 161, 2013, 1076-1085.
Song, Xiu-Fen , et al., "Contributions of Individual Amino Acid Residues to the Endogenous CLV3 Function in Shoot Apical Meristem Maintenance in *Arabidopsis*", Mol Plant 5, 2012, 515-523.
Taguchi-Shiobara, Fumio , et al., "The fasciated ear2 gene encodes a leucine-rich repeat receptor-like protein that regulates shoot meristem proliferation in maize", Gene Dev 15, 2001, 2755-2766.
Tran, Quan Hong , et al., "Mapping-by-Sequencing via MutMap Identifies a Mutation in ZmCLE7 Underlying Fasciation in a Newly Developed EMS Mutant Population in an Elite Tropical Maize Inbred", Genes vol. 11, No. 3, 2020.
Trung, Khuat Huu , et al., "A Weak Allele of Fasciated EAR 2 (FEA2) Increases Maize Kernel Row Number (KRN) and Yield in Elite Maize Hybrids", Agronomy 10, 2020, 1774.
Wu, Qingyu , et al., "All together now, a magical mystery tour of the maize shoot meristem", Current Opinion in Plant Biology 45(part A), 2018, 26-35.
Xu, Cao , et al., "A cascade of arabinosyltransferases controls shoot meristem size in tomato", Nature Genetics, 47(7), 2015, 784-792.
Yamaguchi, Yasuka L., et al., "A Collection of Mutants for CLE-Peptide-Encoding Genes in *Arabidopsis* Generated by CRISPR/Cas9-Mediated Gene Targeting", Plant and Cell Physiology vol. 58, No. 11, 2017, 1848-1856.

(56) References Cited

OTHER PUBLICATIONS

Yang, Yang , et al., "Precise editing of Clavata genes in *Brassica napus* L. regulates multilocular silique development", Plant Biotechnol J 16, 2018, 1322-1335.
Zhu, Y. , et al., "Analysis of interactions among the Clavata3 receptors reveals a direct interaction between Clavata2 and Coryne in *Arabidopsis*", Plant J 61: 223-233, 2009.
Zsogon, Agustin , et al., "Genome editing as a tool to achieve the crop ideotype and de novo domestication of wild relatives: Case study in tomato", Plant Science 256, 2017, 120-130.
Bohorquez, et al., "Mass & secondary structure propensity of amino acids explain their mutability and evolutionary replacements", Scientific Reports 7:7717, 2017 (12 pages).
Mosquna, et al., "Potent and selective activation of abscisic acid receptors in vivo by mutational stabilization of their agonist-bound conformation", PNAS 108, 2011, 20838-20843.

* cited by examiner

METHODS AND COMPOSITIONS FOR CONTROLLING MERISTEM SIZE FOR CROP IMPROVEMENT

STATEMENT OF PRIORITY

This application claims the benefit, under 35 U.S.C. § 119 (e), of U.S. Provisional Application No. 63/356,527 filed on Jun. 29, 2022, the entire content of which is incorporated by reference herein.

STATEMENT REGARDING ELECTRONIC FILING OF A SEQUENCE LISTING

A Sequence Listing in XML format, entitled 1499-104_ST26.xml, 222,389 bytes in size, generated on Jun. 8, 2023 and filed herewith, is hereby incorporated by reference into the specification for its disclosures.

PARTIES TO A JOINT RESEARCH AGREEMENT

The claimed invention was made by, or on behalf of, the below listed parties to a joint research agreement. The parties to the joint research agreement are Pairwise Plants Services, Inc. and Monsanto Company.

FIELD OF THE INVENTION

This invention relates to compositions and methods for modifying FASCIATED EAR2 (FEA2) genes in plants, optionally to modify meristem size. The invention further relates to plants having increased kernel row number produced using the methods and compositions of the invention.

BACKGROUND OF THE INVENTION

New plant organs are initiated at the growing tip of the plant called the meristem. In the meristem a population of undifferentiated stem cells is maintained. During growth, the meristem allocates stem-cells to newly formed organs, including seeds, while at the same time reserving some stem-cells to continually maintain the meristem. Several conserved molecular mechanisms have been described that control the size of the stem cell population to ensure organized growth and proper meristem size.

As a result of the modular nature of maize ear development, larger meristems tend to initiate more flowers, and thus, meristem size has a direct effect on kernel row number and yield. The number of flowers initiated during the development of the maize ear directly limits grain yield. An increased number of flowers initiated around the circumference of the ear (kernel row number or KRN) was a major trait selected during maize domestication. Significant advancements through breeding have resulted in dramatic increases in kernel row number, from 2 in teosinte, the ancestor of maize, to ~8-20 rows in modern elite maize varieties. In diverse maize lines kernel row number can get as high as 36.

In the canonical regulatory pathway described in the model plant *Arabidopsis, CLAVATA*3 (CLV3) peptide is secreted from cells in the meristem apex and moves through the apoplast into the central stem-cell domain where it interacts with several Leucine Rich Receptors (LRRs) including *CLAVATA*1 (CLV1) and *CLAVATA*2 (CLV2). This receptor-ligand interaction stimulates signaling that ultimately acts to reduce WUS expression and restrict the expansion of the stem cell population. One of the targets of WUS is the CLV3 gene itself, and in this way WUS acts to limit its own expression and maintain stem cell homeostasis (Fletcher, J. C., *Plants* 7:87 (2018)).

Loss of function mutations in CLV1, CLV2, or CLV3 result in an expansion of the WUS domain and increased meristem size (Schoof et al., *Cell* 100:635-644 (2000)). Often this increase in meristem size results in aberrant plant growth because the meristem expands uncontrollably and becomes disorganized, a phenomenon called fasciation (Je et al., *Nat Genet* 48: ng.3567 (2016a)). Importantly, a larger meristem does not just make larger organs, but rather an increased number of organs around a larger area. Because of this relationship between meristem size and organ number, mutations in maize CLV-WUS signaling genes can lead to increased flower number and yield. However, while strong loss-of-function mutations in the maize CLV2 ortholog FASCIATED EAR2 (FEA2) result in enlarged meristems and an increase in KRN, the ear is disordered and as a result there is no yield increase (Taguchi-Shiobara et al., *Gene Dev* 15:2755-2766 (2001)).

Novel strategies for modulating meristem size are needed to improve crop performance.

SUMMARY OF THE INVENTION

One aspect of the invention provides a corn plant or plant part thereof comprising at least one mutation in an endogenous FASCIATED EAR2 (FEA2) gene that encodes a FEA2 protein, optionally wherein the at least one mutation may be a non-natural mutation.

A second aspect of the invention provides a corn plant cell, comprising an editing system comprising: (a) a CRISPR-Cas effector protein; and (b) a guide nucleic acid (gRNA, gDNA, crRNA, crDNA, sgRNA, sgDNA) comprising a spacer sequence with complementarity to an endogenous target gene encoding an FEA2 protein.

A third aspect of the invention provides a corn plant cell comprising at least one mutation within a FEA2 gene, wherein the mutation is a substitution, insertion or a deletion that is introduced using an editing system that comprises a nucleic acid binding domain that binds to a target site in the FEA2 gene, optionally wherein the at least one mutation may be a non-natural mutation.

A fourth aspect of the invention provides a method of producing/breeding a transgene-free edited corn plant, comprising: crossing the corn plant of the invention with a transgene-free corn plant, thereby introducing the at least one mutation into the corn plant that is transgene-free; and selecting a progeny corn plant that comprises the at least one mutation and is transgene-free, thereby producing a transgene-free edited corn plant, optionally wherein the at least one mutation may be a non-natural mutation.

A fifth aspect of the invention provides a method of providing a plurality of corn plants having increased kernel row number, the method comprising planting two or more plants of the invention in a growing area, thereby providing a plurality of corn plants having increased kernel row number as compared to a plurality of control corn plants not comprising the mutation.

A sixth aspect of the invention provides a method of generating variation in a region of a corn FEA2 protein, comprising: introducing an editing system into a corn plant cell, wherein the editing system is targeted to a region of a FEA2 gene that encodes a FEA2 polypeptide, and contacting the region of the FEA2 gene with the editing system, thereby introducing a mutation into the FEA2 gene and generating variation in in a region of the FEA2 protein of the corn plant cell.

A seventh aspect of the invention provides a method of detecting a mutant FEA2 gene (a mutation in an endogenous FEA2 gene) in a corn plant, the method comprising detecting in the genome of the corn plant a FEA2 gene having at least one mutation in a region having at least 90% sequence identity to any one of the nucleotide sequences of SEQ ID NOs: 75-77.

In an eighth aspect, a method of creating a mutation in an endogenous FEA2 gene in a corn plant is provided, the method comprising: (a) targeting a gene editing system to a portion of the FEA2 gene that comprises a sequence having at least 80% sequence identity to any one of SEQ ID NOs: 75-77; and (b) selecting a corn plant that comprises a modification located in a region of the FEA2 gene having at least 80% sequence identity to any one of SEQ ID NOs: 75-77.

A ninth aspect provides a method for editing a specific site in the genome of a corn plant cell, the method comprising: cleaving, in a site specific manner, a target site within an endogenous FEA2 gene in the corn plant cell, the endogenous FEA2 gene (a) comprising a nucleotide sequence having at least 90% sequence identity to SEQ ID NO:72 or SEQ ID NO: 73, (b) comprising a region having at least 90% sequence identity to any one of the nucleotide sequences of SEQ ID NOs: 75-77, (c) encoding an amino acid sequence having at least 90% sequence identity to SEQ ID NO:74, and/or (d) encoding a polypeptide comprising a region having at least 90% sequence identity to SEQ ID NOs: 78-80, thereby generating an edit in the endogenous FEA2 gene of the corn plant cell and producing a corn plant cell comprising the edit in the endogenous FEA2 gene.

A tenth aspect provides a method for making a corn plant, comprising: (a) contacting a population of corn plant cells comprising a wild type endogenous FEA2 gene with a nuclease linked to a nucleic acid binding domain (e.g., editing system) that binds to a sequence having at least 90% sequence identity to the nucleotide sequence of any one of SEQ ID NOs: 75-77 or to a sequence encoding an amino acid sequence having at least 90% sequence identity to any one of SEQ ID NOs: 78-80; (b) selecting a corn plant cell from the population in which an endogenous FEA2 gene has been mutated, thereby producing a corn plant cell comprising at least one mutation in the endogenous FEA2 gene; and (c) growing the selected corn plant cell into a corn plant.

An eleventh aspect provides a method for increasing kernel row number in a corn plant, comprising (a) contacting a corn plant cell comprising an endogenous FEA2 gene with a nuclease targeting the endogenous FEA2 gene, wherein the nuclease is linked to a nucleic acid binding domain (e.g., editing system) that binds to a target site within the endogenous FEA2 gene, wherein the endogenous FEA2 gene: (i) comprises a nucleotide sequence having at least 90% sequence identity to the sequence of SEQ ID NO:72 or SEQ ID NO:73; (ii) encodes an amino acid sequence having at least 90% sequence identity to the sequence of SEQ ID NO:74; (iii) comprises a region having at least 90% sequence identity to the nucleotide sequence of any one of SEQ ID NOs: 75-77; and/or (iv) encodes a region of a polypeptide having at least 90% sequence identity to any one of the amino acid sequences of SEQ ID NOs: 78-80 to produce a corn plant cell comprising a mutation in the wild type endogenous FEA2 gene; and (b) growing the corn plant cell into a corn plant comprising the mutation in the endogenous FEA2 gene, thereby producing a corn plant have a mutated endogenous FEA2 gene and exhibiting increased yield and/or an increased kernel row number, optionally exhibiting an increased kernel row number without substantially reducing ear length.

A twelfth aspect provides method for producing a corn plant or part thereof comprising at least one cell having a mutation in an endogenous FEA2 gene, the method comprising contacting a target site within an endogenous FEA2 gene in the corn plant or plant part with a nuclease comprising a cleavage domain and a nucleic acid binding domain, wherein the nucleic acid binding domain binds to a target site in the endogenous FEA2 gene, wherein the endogenous FEA2 gene (a) comprises a nucleotide sequence having at least 90% sequence identity to the sequence of SEQ ID NO:72 or SEQ ID NO:73; (b) encodes an amino acid sequence having at least 90% sequence identity to the sequence of SEQ ID NO:74; (c) comprises a region having at least 90% sequence identity to the nucleotide sequence of any one of SEQ ID NOs: 75-77; and/or (d) encodes a region of a polypeptide having at least 90% sequence identity to any one of the amino acid sequences of SEQ ID NOs: 78-80, thereby producing the corn plant or part thereof comprising at least one cell having a mutation in the endogenous FEA2 gene.

A thirteenth aspect of the invention provides a method for producing a corn plant or part thereof comprising a mutated endogenous FEA2 gene and exhibiting increased kernel row number (e.g., producing ears having increased kernel row number, optionally without substantially decreasing the length of the ears), the method comprising contacting a target site within an endogenous FEA2 gene in the corn plant or plant part with a nuclease comprising a cleavage domain and a nucleic acid binding domain, wherein the nucleic acid binding domain binds to a target site within the endogenous FEA2 gene, wherein the endogenous FEA2 gene: (a) comprises a nucleotide sequence having at least 90% sequence identity to the sequence of SEQ ID NO:72 or SEQ ID NO:73; (b) encodes an amino acid sequence having at least 90% sequence identity to the sequence of SEQ ID NO:74; (c) comprises a region having at least 90% sequence identity to the nucleotide sequence of any one of SEQ ID NOs: 75-77; and/or (d) encodes a region of a polypeptide comprising a region having at least 90% sequence identity to the amino acid sequence of any one of SEQ ID NOs: 78-80, thereby producing the corn plant or part thereof comprising an endogenous FEA2 gene having a mutation and exhibiting increased yield and/or increased kernel row number, optionally wherein when kernel row number is increased, ear length is not substantially reduced.

In a fourteenth aspect, a method is provided for modifying an endogenous FEA2 gene in a corn plant or part thereof for improving a yield trait in the corn plant or part thereof, the method comprising modifying a target site within the endogenous FEA2 gene in the corn plant or a part thereof, wherein the endogenous FEA2 gene: (a) comprises a sequence having at least 90% sequence identity to the nucleotide sequence of SEQ ID NO:72 or SEQ ID NO:73; (b) comprises a region having at least 90% sequence identity to any one of the nucleotide sequences of SEQ ID NOs: 75-77; (c) encodes a polypeptide comprising a sequence having at least 90% sequence identity to the amino acid sequence of SEQ ID NO:74; and/or (d) encodes a region of a polypeptide comprising a region having at least 90% sequence identity to the amino acid sequence of SEQ ID NO:78-80, thereby modifying the endogenous FEA2 gene and improving a yield trait in the corn plant or part thereof.

In a fifteenth aspect, a guide nucleic acid is provided that binds to a target site in a FEA2 gene, the target site comprising the nucleotide sequence of any one of SEQ ID NOs: 75-77 or a nucleotide sequence that encodes an amino acid sequence of any one of SEQ ID NOs: 78-80.

A sixteenth aspect provides, a system is provided comprising a guide nucleic acid of the invention and a CRISPR-Cas effector protein that associates with the guide nucleic acid In a seventeenth aspect, a gene editing system is provided comprising a CRISPR-Cas effector protein in association with a guide nucleic acid, wherein the guide nucleic acid comprises a spacer sequence that binds to an endogenous FEA2 gene.

In an eighteenth aspect, a complex is provided, the complex comprising a guide nucleic acid and a CRISPR-Cas effector protein comprising a cleavage domain, wherein the guide nucleic acid binds to a target site within an endogenous FEA2 gene, wherein the endogenous FEA2 gene, wherein the endogenous FEA2 gene: (a) comprises a nucleotide sequence having at least 90% sequence identity to the sequence of SEQ ID NO:72 or SEQ ID NO:73; (b) encodes an amino acid sequence having at least 90% sequence identity to the sequence of SEQ ID NO: 74; (c) comprises a region having at least 90% sequence identity to the nucleotide sequence of any one of SEQ ID NOs: 75-77; and/or (d) encodes a region of a polypeptide comprising a region having at least 90% sequence identity to the amino acid sequence of any one of SEQ ID NOs: 78-80, wherein the cleavage domain cleaves a target strand in the FEA2 gene.

In a nineteenth aspect, an expression cassette is provided, the expression cassette comprising (a) a polynucleotide encoding CRISPR-Cas effector protein comprising a cleavage domain and (b) a guide nucleic acid that binds to a target site within an endogenous FEA2 gene, wherein the guide nucleic acid comprises a spacer sequence that is complementary to and binds to (i) a portion of a nucleic acid encoding an amino acid sequence having at least 90% sequence identity the amino acid sequence of SEQ ID NO:74; (ii) a portion of a sequence having at least 90% sequence identity to the nucleotide sequence of SEQ ID NO:72 or SEQ ID NO: 73; (iii) a portion of a sequence having at least 90% sequence identity to any one of the nucleotide sequences of any one of SEQ ID NOs: 75-77; and/or (iv) a portion of a nucleic acid encoding a region of a polypeptide having at least 90% sequence identity to the amino acid sequence of any one of SEQ ID NOs: 78-80.

In a twentieth aspect, a nucleic acid is provided that encodes a dominant negative mutation, a semi-dominant mutation or a weak loss-of-function mutation of a corn FEA2 protein.

Also provided herein is a FEA2 polypeptide having at least 90% sequence identity to any one of SEQ ID NOs: 83, 85, 87, 89, 91, 93, 95, 97, or 99, the modified FEA2 polypeptide comprising a mutation in at least one non-natural mutation is located in the 10th LRR repeat of the encoded FEA2 polypeptide, SEQ ID NO:74.

In an additional aspect, a corn plant or part thereof is provided comprising one or more mutated FEA2 genes, wherein the one or more mutated FEA2 genes comprise a sequence having at least 90% sequence identity to any one of SEQ ID NOs: 82, 84, 86, 88, 90, 92, 94, 96 or 98 and/or encoding a mutated FEA2 polypeptide having at least 90% sequence identity to any one of SEQ ID NOs: 83, 85, 87, 89, 91, 93, 95, 97, or 99.

In a further aspect, a corn plant or part thereof is provided comprising at least one mutation in an endogenous FEA2 gene that exhibits increased yield and/or increased kernel row number (e.g., producing ears having increased kernel row number, optionally without substantially decreasing the length of the ears), optionally wherein the at least one mutation may be a non-natural mutation. In some aspects, a corn plant is provided that also exhibits increased yield and larger floral meristems.

Further provided are corn plants comprising in their genome one or more mutated FASCIATED EAR2 (FEA2) genes produced by the methods of the invention as well as polypeptides, polynucleotides, nucleic acid constructs, expression cassettes and vectors for making a corn plant of this invention.

These and other aspects of the invention are set forth in more detail in the description of the invention below.

BRIEF DESCRIPTION OF THE SEQUENCES

SEQ ID NOs: 1-17 are exemplary Cas12a amino acid sequences useful with this invention.

SEQ ID NOs: 18-20 are exemplary Cas12a nucleotide sequences useful with this invention.

SEQ ID NO:21-22 are exemplary regulatory sequences encoding a promoter and intron.

SEQ ID NOs: 23-29 are exemplary cytosine deaminase sequences useful with this invention.

SEQ ID NOs: 30-40 are exemplary adenine deaminase amino acid sequences useful with this invention.

SEQ ID NO:41 is an exemplary uracil-DNA glycosylase inhibitor (UGI) sequences useful with this invention.

SEQ ID NOs: 42-44 provides an example of a protospacer adjacent motif position for a Type V CRISPR-Cas12a nuclease.

SEQ ID NOs: 45-47 provide example peptide tags and affinity polypeptides useful with this invention.

SEQ ID NOs: 48-58 provide example RNA recruiting motifs and corresponding affinity polypeptides useful with this invention.

SEQ ID NOs: 59-60 are exemplary Cas9 polypeptide sequences useful with this invention.

SEQ ID NOs: 61-71 are exemplary Cas9 polynucleotide sequences useful with this invention.

SEQ ID NO:72 is an example FEA2 genomic sequence.

SEQ ID NO:73 is an example FEA2 coding (cds) sequence.

SEQ ID NO:74 is an example FEA2 polypeptide sequence.

SEQ ID NOs: 75-77 are example target regions of an FEA2 genomic sequence useful with this invention.

SEQ ID NOs: 77-80 are example target regions of an FEA2 polypeptide useful with this invention.

SEQ ID NO:81 is an example spacer sequence for nucleic acid guides useful with this invention.

SEQ ID NOs: 82, 84, 86, 88, 90, 92, 94, 96 and 98 are example edited FEA2 nucleic acid sequences produced as described herein.

SEQ ID NOs: 83, 85, 87, 89, 91, 93, 95, 97, and 99 are example mutated FEA2 polypeptides produced by the edited nucleic acid sequences of SEQ ID NOs: 82, 84, 86, 88, 90, 92, 94, 96 and 98, respectively.

DETAILED DESCRIPTION

The present invention now will be described hereinafter with reference to the accompanying examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms “a,” “an” and “the” are intended to include the plural forms as well, unless the context clearly indicates otherwise.

Also as used herein, “and/or” refers to and encompasses any and all possible combinations of one or more of the associated listed items, as well as the lack of combinations when interpreted in the alternative (“or”).

The term “about,” as used herein when referring to a measurable value such as an amount or concentration and the like, is meant to encompass variations of ±10%, ±5%, ±1%, ±0.5%, or even ±0.1% of the specified value as well as the specified value. For example, “about X” where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as “between X and Y” and “between about X and Y” should be interpreted to include X and Y. As used herein, phrases such as “between about X and Y” mean “between about X and about Y” and phrases such as “from about X to Y” mean “from about X to about Y.”

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term “comprise,” “comprises” and “comprising” as used herein, specify the presence of the stated features, integers, steps, operations, elements, and/or components, but do not preclude the presence or addition of one or more other features, integers, steps, operations, elements, components, and/or groups thereof.

As used herein, the transitional phrase “consisting essentially of” means that the scope of a claim is to be interpreted to encompass the specified materials or steps recited in the claim and those that do not materially affect the basic and novel characteristic(s) of the claimed invention. Thus, the term “consisting essentially of” when used in a claim of this invention is not intended to be interpreted to be equivalent to “comprising.”

As used herein, the terms “increase,” “increasing,” “increased,” “enhance,” “enhanced,” “enhancing,” and “enhancement” (and grammatical variations thereof) describe an elevation of at least about 5%, 10%, 15%, 20%, 25%, 50%, 75%, 100%, 150%, 200%, 300%, 400%, 500% or more as compared to a control. For example, a corn plant comprising a mutation in an FEA2 gene as described herein can exhibit increased kernel row number (e.g., producing ears having increased kernel row number) that is at least about 5% or greater than that of a control plant not comprising the same mutation, optionally wherein the length of the ears comprising increased kernel row number is not substantially decreased (e.g., a decrease in length of less than 30% as compared to an ear of a corn plant not comprising the same FEA2 mutation). A control plant is typically the same plant as the edited plant but the control plant has not been similarly edited and therefore does not comprise the mutation. A control plant maybe an isogenic plant and/or a wild type plant. Thus, a control plant can be the same breeding line, variety, or cultivar as the subject plant into which a mutation as described herein is introgressed, but the control breeding line, variety, or cultivar is free of the mutation. In some embodiments, a comparison between a plant of the invention and a control plant is made under the same growth conditions, e.g., the same environmental conditions (soil, hydration, light, heat, nutrients and the like).

As used herein, the terms “reduce,” “reduced,” “reducing,” “reduction,” “diminish,” and “decrease” (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In particular embodiments, the reduction can result in no or essentially no (i.e., an insignificant amount, e.g., less than about 10% or even 5%) detectable activity or amount.

As used herein, the terms “express,” “expresses,” “expressed” or “expression,” and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

A “heterologous” or a “recombinant” nucleotide sequence is a nucleotide sequence not naturally associated with a host cell into which it is introduced, including non-naturally occurring multiple copies of a naturally occurring nucleotide sequence. A “heterologous” nucleotide/polypeptide may originate from a foreign species, or, if from the same species, is substantially modified from its native form in composition and/or genomic locus by deliberate human intervention.

A corn plant in which at least one (e.g., one or more, e.g., 1, 2, 3, or 4, or more) endogenous FEA2 genes is modified as described herein (e.g., comprises a modification as described herein) may have improved yield traits as compared to a corn plant that does not comprise (is devoid of) the modification in the at least one endogenous FEA2 gene. As used herein, "improved yield traits" refers to any plant trait associated with growth, for example, biomass, yield, nitrogen use efficiency (NUE), inflorescence size/weight, fruit yield, fruit quality, fruit size, seed size (e.g., seed area, seed size), seed number, foliar tissue weight, nodulation number, nodulation mass, nodulation activity, number of seed heads, number of tillers, number of branches, number of flowers, number of tubers, tuber mass, bulb mass, number of seeds, total seed mass, rate of leaf emergence, rate of tiller/branch emergence, rate of seedling emergence, length of roots, number of roots, size and/or weight of root mass, or any combination thereof. In some aspects, "improved yield traits" may include, but are not limited to, increased inflorescence production, increased fruit production (e.g., increased number, weight and/or size of fruit; e.g., increased number, weight, and/or length of ears for, e.g., maize), increased fruit quality, increased number, size and/or weight of roots, increased meristem size, increased seed size (e.g., seed area and/or seed weight), increased biomass, increased leaf size, increased nitrogen use efficiency, increased height, increased internode number and/or increased internode length as compared to a control plant or part thereof (e.g., a corn plant that does not comprise a mutated endogenous FEA2 nucleic acid as described herein). In some aspects, improved yield traits can be expressed as quantity of grain/seed produced per area of land (e.g., bushels per acre of land). In some embodiments, a corn plant that comprises a mutated endogenous FEA2 nucleic acid as described herein exhibits increased yield as compared to a control plant devoid of the at least one mutation, optionally wherein the corn plant exhibits a phenotype of increased kernel row number (KRN), optionally wherein ear length is not substantially reduced.

As used herein a "control plant" means a plant that does not contain an edited FEA2 gene or gene as described herein that imparts an enhanced/improved trait (e.g., yield trait) or altered phenotype (e.g., increased yield, increased kernel row number, optionally without a substantial decrease in ear length). A control plant is used to identify and select a plant edited as described herein and that has an enhanced trait or altered phenotype as compared to the control plant. A suitable control plant can be a plant of the parental line used to generate a plant comprising a mutated FEA2 gene(s), for example, a wild type plant devoid of an edit in an endogenous FEA2 gene as described herein. A suitable control plant can also be a plant that contains recombinant nucleic acids that impart other traits, for example, a transgenic plant having enhanced herbicide tolerance. A suitable control plant can in some cases be a progeny of a heterozygous or hemizygous transgenic plant line that is devoid of the mutated FEA2 gene as described herein, known as a negative segregant, or a negative isogenic line. The comparison to a control plant may be under the same environmental conditions.

An enhanced trait (e.g., improved yield trait) may include, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, increased yield, increased nitrogen use efficiency, and/or increased water use efficiency as compared to a control plant. An altered phenotype may be, for example, plant height, biomass, canopy area, anthocyanin content, chlorophyll content, water applied, water content, and water use efficiency.

In some embodiments, a plant of this invention may comprise one or more improved yield traits including, but not limited to, In some embodiments, the one or more improved yield traits includes higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods, including an increased number of pods per node and/or an increased number of pods per plant, increased number of seeds per pod, increased number of seeds, increased seed size, and/or increased seed weight (e.g., increase in 100-seed weight) as compared to a control plant devoid of the at least one mutation. In some embodiments, a plant of this invention may comprise one or more improved yield traits including, but not limited to, optionally an increase in yield (bu/acre), seed size (including kernel size), seed weight (including kernel weight), increased kernel row number (optionally wherein ear length is not substantially reduced), increased number of pods, increased number of seeds per pod and an increase in ear length as compared to a control plant or part thereof.

As used herein a "trait" is a physiological, morphological, biochemical, or physical characteristic of a plant or particular plant material or cell. In some instances, this characteristic is visible to the human eye and can be measured mechanically, such as seed or plant size, weight, shape, form, length, height, growth rate and development stage, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. However, any technique can be used to measure the amount of, the comparative level of, or the difference in any selected chemical compound or macromolecule in the transgenic plants.

As used herein an "enhanced trait" means a characteristic of a plant resulting from mutations in a FEA2 gene(s) as described herein. Such traits include, but are not limited to, an enhanced agronomic trait characterized by enhanced plant morphology, physiology, growth and development, yield, nutritional enhancement, disease or pest resistance, or environmental or chemical tolerance. In some embodiments, an enhanced trait/altered phenotype may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, drought tolerance, increased water use efficiency, cold tolerance, increased nitrogen use efficiency, and/or increased yield. In some embodiments, a trait is increased yield under nonstress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. “Yield” can be affected by many properties including without limitation, plant height, plant biomass, pod number, pod position on the plant, number of internodes, incidence of pod shatter, grain size, ear size, ear tip filling, kernel abortion, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), flowering time and duration, ear number, ear size, ear weight, seed number per ear or pod, seed size, composition of seed (starch, oil, protein) and characteristics of seed fill.

Also used herein, the term “trait modification” encompasses altering the naturally occurring trait by producing a detectable difference in a characteristic in a plant comprising a mutation in an endogenous FEA2 gene as described herein relative to a plant not comprising the mutation, such as a wild type plant, or a negative segregant. In some cases, the trait modification can be evaluated quantitatively. For example, the trait modification can entail an increase or decrease in an observed trait characteristic or phenotype as compared to a control plant. It is known that there can be natural variations in a modified trait. Therefore, the trait modification observed can entail a change of the normal distribution and magnitude of the trait characteristics or phenotype in the plants as compared to a control plant.

The present disclosure relates to a corn plant with improved economically relevant characteristics, more specifically increased yield and/or increased KRN, optionally wherein the increase in KRN does not results in a substantial decrease in ear length (e.g., a decrease of 30% or less) compared to a control plant. More specifically the present disclosure relates to a corn plant comprising a mutation(s) in a FEA2 gene(s) as described herein, wherein the corn plant exhibits exhibiting increased yield and/or increased kernel row number (KRN), optionally wherein ear length is not substantially reduced, as compared to a control plant devoid of said mutation(s). In some embodiments, a plant of the present disclosure exhibits further improved traits related to yield, including but not limited to increased nitrogen use efficiency, increased nitrogen stress tolerance, increased water use efficiency and/or increased drought tolerance, as defined and discussed infra.

Yield can be defined as the measurable produce of economic value from a crop. Yield can be defined in the scope of quantity and/or quality. Yield can be directly dependent on several factors, for example, the number and size of organs (e.g., number of flowers), plant architecture (such as the number of branches, plant biomass, e.g., increased root biomass, steeper root angle and/or longer roots, and the like), flowering time and duration, grain fill period. Root architecture and development, photosynthetic efficiency, nutrient uptake, stress tolerance, early vigor, delayed senescence and functional stay green phenotypes may be factors in determining yield. Optimizing the above-mentioned factors can therefore contribute to increasing crop yield.

Reference herein to an increase/improvement in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term “yield” of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens.

“Increased yield” can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination.

“Early vigor” refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor, for example, can be a combination of the ability of seeds to germinate and emerge after planting and the ability of the young plants to grow and develop after emergence. Plants having early vigor also show increased seedling survival and better establishment of the crop, which often results in highly uniform fields with the majority of the plants reaching the various stages of development at substantially the same time, which often results in increased yield. Therefore, early vigor can be determined by measuring various factors, such as kernel weight, percentage germination, percentage emergence, seedling growth, seedling height, root length, root and shoot biomass, canopy size and color and others.

Further, increased yield can also manifest as increased total seed yield, which may result from one or more of an increase in seed biomass (seed weight) due to an increase in the seed weight on a per plant and/or on an individual seed basis an increased number of, for example, flowers/panicles per plant; an increased number of pods; an increased number of nodes; an increased number of flowers (“florets”) per panicle/plant; increased seed fill rate; an increased number of filled seeds; increased seed size (length, width, area, perimeter, and/or weight), which can also influence the composition of seeds; and/or increased seed volume, which can also influence the composition of seeds. In one embodiment, increased yield can be increased seed yield, for example, increased seed weight; increased number of filled seeds; and/or increased harvest index.

Increased yield can also result in modified architecture, or can occur because of modified plant architecture.

Increased yield can also manifest as increased harvest index, which is expressed as a ratio of the yield of harvestable parts, such as seeds, over the total biomass The disclosure also extends to harvestable parts of a plant such as, but not limited to, seeds, leaves, fruits, flowers, bolls, pods, siliques, nuts, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance and can also improve crop quality and biochemical constituents of the seed such as protein yield and oil yield. The terms "increased nitrogen use efficiency", "enhanced nitrogen use efficiency", and "nitrogen stress tolerance" are used interchangeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Typically, plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein, "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein, "water deficit" refers to the conditions or environments that provide less than optimal amounts of water needed for adequate/successful growth and development of plants.

As used herein, "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

A "native" or "wild type" nucleic acid, nucleotide sequence, polypeptide or amino acid sequence refers to a naturally occurring or endogenous nucleic acid, nucleotide sequence, polypeptide, or amino acid sequence. In some contexts, a "wild type" nucleic acid is a nucleic acid that is not edited as described herein and can differ from an "endogenous" gene that may be edited as described herein (e.g., a mutated endogenous gene). In some contexts, a "wild type" nucleic acid (e.g., unedited) may be heterologous to the organism in which the wild type nucleic acid is found (e.g., a transgenic organism). As an example, a "wild type endogenous FASCIATED EAR2 (FEA2) gene" is a FEA2 gene that is naturally occurring in or endogenous to the reference organism, e.g., a plant (e.g., a corn plant), and may be subject to modification as described herein, after which, such a modified endogenous gene is no longer wild type.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is non-functional.

A "recessive mutation" is a mutation in a gene that produces a phenotype when homozygous but the phenotype is not observable when the locus is heterozygous.

A "dominant mutation" is a mutation in a gene that produces a mutant phenotype in the presence of a non-mutated copy of the gene. A dominant mutation may be a loss or a gain of function mutation, a hypomorphic mutation, a hypermorphic mutation or a weak loss of function or a weak gain of function.

A "dominant negative mutation" is a mutation that produces an altered gene product (e.g., having an aberrant function relative to wild type), which gene product adversely affects the function of the wild type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wildtype gene product.

A "hypomorphic mutation" is a mutation that results in a partial loss of gene function, which may occur through reduced expression (e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

A "hypermorphic mutation" is a mutation that results in increased expression of the gene product and/or increased activity of the gene product.

A "gain-of-function" allele or mutation is a mutation that confers a new function on the encoded gene product and/or confers a new gene expression pattern. In some embodiments, a gain-of-function mutation may be dominant or semi-dominant.

As used herein, a "non-natural mutation" refers to a mutation that is generated through human intervention and differs from mutations found in the same gene that have occurred in nature (e.g., occurred naturally and not as a result of a modification made by a human).

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. Marker-assisted Backcrossing: A Practical Example, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the World Intellectual Property Organization (WIPO) Standard ST.26. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20, 20, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, or 900 or more nucleotides or any range or value therein) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a "portion" of a wild type CRISPR-Cas repeat sequence (e.g., a wild Type CRISPR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

In some embodiments, a nucleic acid fragment may comprise, consist essentially of or consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 320, 330, 340, 350, 360, 370, 380, 390, 395, 400, 410, 415, 420, 425, 430, 435, 440, 445, 450, 500, 550, 600, 650, 700, 750, 800, 850, 900, 950, 1000, 1100, 1150, 1200, 1250, 1300, 1350, 1400, 1450, 1500, 1550, 1600, 1650, 1700, 1750, 1800, 1850, 1900, 1950, 2000, 2500, 3000, 3500, or 4000 or more consecutive nucleotides or any range or value therein of a nucleic acid encoding a FEA2 polypeptide, optionally a fragment of a FEA2 gene may be about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 115, 120, 125, 130, 135, 140, 145, 150 consecutive nucleotides to about 155, 160, 165, 170, 175, 180, 185, 190, 195, 200, 205, 210, 215, 220, 221, 222, 223, 224, 225, 230, 240, 245, 250, 255, 260, 265, 270, 275, 280, 285, 290, 295, 300, 305, 310, 315, 320, 325, 330, 340, 345, 350, 355, 360, 365, 370, 375, 380, 385, 390, 395, or 400, or more consecutive nucleotides in length, or any range or value therein (e.g., a fragment or portion of SEQ ID NO:72 or SEQ ID NO: 73 (e.g., of SEQ ID NOs: 75-77).

In some embodiments, a "sequence-specific nucleic acid binding domain" (e.g., sequence-specific DNA binding domain) may bind to one or more fragments or portions of nucleotide sequences encoding FEA2 polypeptides as described herein.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 260, 270, 280, 290, or more consecutive amino acids of a reference polypeptide. In some embodiments, a FEA2 polypeptide fragment may comprise, consist essentially of or consist of about 10, 11, 12, 13, 14, 15, 16, 17, 18, 19, 20, 21, 22, 23, 24, 25, 26, 27, 28, 29, 30, 35, 40, 45, 50, 60, 70, 71, 72, 73, 74, 75, 80, 90, 100, 125, 150, 175, 200, 225, 250, 275, 300, 350, 400, 450, 500, 550, or 600 consecutive amino acid residues, or any range or value therein (e.g., a fragment or a portion of SEQ ID NO:74 (e.g., SEQ ID NOs: 78-80)). In some embodiments, a fragment of an FEA2 polypeptide or an FEA2 polynucleotide maybe the result of a deletion generated in the FEA2 gene or may be the result of an amino acid substitution resulting in a truncated polypeptide. A deletion may result in an in-frame deletion allele or an out-of-frame deletion allele. An FEA2 gene may be edited in more than one location, thereby providing an FEA2 gene comprising more than one mutation.

In some embodiments, a "portion" or "region" in reference to a nucleic acid means at least 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103,104, 105, 106, 107, 108, 109, 110, 115, 120, 125, 130, 135,140, 145, 150, 155, 160, 165, 170, 175, 180, 185, 190, 195, 200, 210, 220, 221, 222, 223, 224, 225, 226, 227, 228, 229, 230, 240, 250, 260, 270, 280, 285, 290, 300, 310, 320, 330, 340, 350, 360, 370, 380, 390, 395, 400, 405, 410, 415, 420, 425, 430, 435, 440, 445, 450, 500, 600, 700, 800, 900, 1000, 1100, 1200, 1300, 1400, 1500, 1600, 1700, 1800, 1900, 2000, 2500, 3000, 3500, 4000, 4500, or 5000 or more consecutive nucleotides from a gene (e.g., consecutive nucleotides from an FEA2 gene), optionally a "portion" or "region" of a FEA2 gene may be about 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 80, 90, 100, 101, 102, 103, 104, 105, 110, 115, 120, 125, 130, 135, 140, 141, 142, 143, 144, 145, or 150 consecutive nucleotides to about 155, 160, 165, 170, 175, 180, 185, 190, 195, 200, 205, 210, 215, 220, 221, 222, 223, 224, 225, 230, 235, 240, 245, 250, 255, 255, 260, 265, 270, 275, 280, 285, 290, 295, 300, 305, 310, 315, 320, 325, 326, 327, 328, 329, 330, 340, 345, 350, 355, 360, 365, 370, 375, 380, 385, 390, 395, 400, 405, 410, 415, 420, 425, 430, 435, 440, 445, or 450, or more consecutive nucleotides in length, or any range or value therein (e.g., a portion or region of consecutive nucleotides from SEQ ID NO:72; e.g., SEQ ID NOs: 75-77). In some embodiments, a "portion" or "region" in reference to a polypeptide means at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 consecutive amino acid residues to about 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 75, 75, 76, 77, 78, 79 or 80 or more consecutive amino acid residues from a polypeptide (e.g., a FEA2 polypeptide, e.g., SEQ ID NO:74; for example, see SEQ ID NOs: 78-80).

In some embodiments, a "sequence-specific nucleic acid binding domain" may bind to one or more fragments or portions of nucleotide sequences encoding FEA2 polypeptides as described herein.

As used herein with respect to nucleic acids, the term "functional fragment" refers to nucleic acid that encodes a functional fragment of a polypeptide. A "functional fragment" with respect to a polypeptide is a fragment of a polypeptide that retains one or more of the activities of the native reference polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. A truncation can include a truncation at the C-terminal end of a polypeptide or at the N-terminal end of a polypeptide. A truncation of a polypeptide can be the result of a deletion of the corresponding 5' end or 3' end of the gene encoding the polypeptide. A frameshift mutation can occur when deletions or insertions of one or more base pairs are introduced into a gene. Frameshift mutations in a gene can result in the production of a polypeptide that is longer, shorter or the same length as the wild type polypeptide depending on when the first stop codon occurs following the mutated region of the gene.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein, "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent sequence identity" can refer to the percentage of identical amino acids in an amino acid sequence as compared to a reference polypeptide. In regard to a FEA2 gene, a sequence may have at least 90% sequence identity to the nucleotide sequence of SEQ ID NO:72 or SEQ ID NO:73. In some embodiments, a FEA2 gene may have at least 95% sequence identity to the nucleotide sequence of SEQ ID NO:72 or SEQ ID NO: 73, optionally wherein the FEA2 gene may have 100% sequence identity to the nucleotide sequence of SEQ ID NO:72 or SEQ ID NO:73. A FEA2 polypeptide as described herein may have at least 90% sequence identity to the polypeptide sequence of SEQ ID NO:74. In some embodiments, a FEA2 polypeptide may have at least 95% sequence identity to the polypeptide sequence of SEQ ID NO:74, optionally wherein the FEA2 polypeptide may have 100% sequence identity to the polypeptide sequence of SEQ ID NO:74. With regard to regions or portions of a FEA2 gene, the region or portion may have at least 90% sequence identity to the nucleotide sequence of any one of SEQ ID NOs: 75-77, optionally at least 90% sequence identity to any one of SEQ ID NOs: 75, 76, and/or 77. In some embodiments, a region or portion of a FEA2 gene may have at least 95% sequence identity to the nucleotide sequence of any one of SEQ ID NOs: 75-77, optionally at least 90% sequence identity to any one of SEQ ID NOs: 75, 76, and/or 77. In some embodiments, a region or portion of a FEA2 gene may have 100% sequence identity to the nucleotide sequence of any one of SEQ ID NOs: 75-77, optionally 100% sequence identity to any one of SEQ ID NOs: 75, 76, and/or 77. In some embodiments, a region or portion of a FEA2 polypeptide may have at least 90% sequence identity to the amino acid sequence of SEQ ID NOs: 78-80, optionally at least 90% sequence identity to any one of SEQ ID NOs: 78, 79, and/or 80. In some embodiments, a region or portion of a FEA2 polypeptide may have at least 95% sequence identity to the amino acid sequence of SEQ ID NOs: 78-80, optionally at least 95% sequence identity to any one of SEQ ID NOs: 78, 79, and/or 80. In some embodiments, a region or portion of a FEA2 polypeptide may have 100% sequence identity to the amino acid sequence of SEQ ID NOs: 78-80, optionally 100% sequence identity to any one of SEQ ID NOs: 78, 79, and/or 80. With regard to mutated or edited FEA2 genes, a mutated or edited FEA2 gene may have at least 90% sequence identity to the nucleotide sequence of any one of SEQ ID NOs: 82, 84, 86, 88, 90, 92, 94, 96 or/or 98. In some embodiments, a mutated or edited FEA2 gene may have at least 95% sequence identity to the nucleotide sequence of any one of SEQ ID NOs: 82, 84, 86, 88, 90, 92, 94, 96 or/or 98. In some embodiments, a mutated or edited FEA2 gene may have 100% sequence identity to the nucleotide sequence of any one of SEQ ID NOs: 82, 84, 86, 88, 90, 92, 94, 96 or/or 98. In some embodiments, a mutated FEA2 polypeptide may have at least 90% sequence identity to the amino acid sequence of any one of SEQ ID NOs: 83, 85, 87, 89, 91, 93, 95, 97, or 99. In some embodiments, a mutated FEA2 polypeptide may have at least 95% sequence identity to the amino acid sequence of any one of SEQ ID NOs: 83, 85, 87, 89, 91, 93, 95, 97, or 99. In some embodiments, a mutated FEA2 polypeptide may have 100% sequence identity to the amino acid sequence of any one of SEQ ID NOs: 83, 85, 87, 89, 91, 93, 95, 97, or 99.

As used herein, the phrase "substantially identical," or "substantial identity" in the context of two nucleic acid molecules, nucleotide sequences, or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, or more in length, or any range therein, up to the full length of the sequence. In some embodiments, nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40, 50, 60, 70, or 80 nucleotides or more).

In some embodiments of the invention, the substantial identity exists over a region of consecutive amino acid residues of a polypeptide of the invention that is about 3 amino acid residues to about 20 amino acid residues, about 5 amino acid residues to about 25 amino acid residues, about 7 amino acid residues to about 30 amino acid residues, about 10 amino acid residues to about 25 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8 to about 350 consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 300, 350 or more amino acids in length or more consecutive amino acid residues). In some embodiments, two or more FEA2 polypeptides may be identical or substantially identical (e.g., at least 70% to 99.9% identical, e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9% identical or any range or value therein) over at least 8, 9, 10, 11, 12, 13, 14, or 15 consecutive amino acids to about 20, 21, 22, 23, 24, 25, 26, 27, 28, 29, 30, 31, 32, 33, 34, 35, 36, 37, 38, 39, or 40 consecutive amino acids.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific nucleic acid binding domain (e.g., a sequence-specific nucleic acid binding domain from a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9% or 100%) identity or more to the reference nucleic acids, polynucleotides, expression cassettes, and/or vectors that have not been codon optimized.

In embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a nucleic acid binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid, or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g., extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in *Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. Gene 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. Gene 403:132-142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) Nature 313:810-812), CaMV 19S promoter (Lawton et al. (1987) *Plant Mol. Biol.* 9:315-324), nos promoter (Ebert et al. (1987) Proc. Natl. Acad. Sci USA 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79:87-94), maize (Christensen et al., 1989. *Plant Molec. Biol.* 12:619-632), and *arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231:150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as B-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP U.S. Pat. No. 255,378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9 (5): 297-306 (2015)), ZmSTK2_USP from maize (Wang et al. *Genome* 60 (6): 485-495 (2017)), LAT52 and LAT59 from tomato (Twell et al. *Development* 109 (3): 705-713 (1990)), Zm13 (U.S. Pat. No. 10,421,972), $PLA_2$-δ promoter from *arabidopsis* (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958- 2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37 (8): 1108-1115), corn light harvesting complex promoter (Bansal et al. (1992) Proc. Natl. Acad. Sci. USA 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) Mol. Gen. Genet. 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-0 tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g., SEQ ID NO:21 and SEQ ID NO:22).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific nucleic acid (e.g., DNA) binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific nucleic acid binding domain, a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter, or they may be different promoters. Thus, a polynucleotide encoding a sequence specific nucleic acid binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific nucleic acid binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific nucleic acid binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, “selectable marker” means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term “vector” refers to a composition for transferring, delivering or introducing a nucleic acid (or nucleic acids) into a cell. A vector comprises a nucleic acid construct (e.g., expression cassette(s)) comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g., autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g., higher plant, mammalian, yeast, or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, “contact,” “contacting,” “contacted,” and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific nucleic acid binding protein (e.g., polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific nucleic acid binding protein, the reverse transcriptase and/or the deaminase are expressed and the sequence-specific nucleic acid binding protein binds to the target nucleic acid, and the reverse transcriptase and/or deaminase may be fused to either the sequence-specific nucleic acid binding protein or recruited to the sequence-specific nucleic acid binding protein (via, for example, a peptide tag fused to the sequence-specific nucleic acid binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, "modifying" or "modification" in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a corn plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

The present invention provides methods and compositions for reducing the influence of genes that normally act to restrict meristem size in order to generate plants with larger floral meristems, to increase kernel row number (optionally without substantially decreasing ear length (e.g., without decreasing ear length more than 30% as compared to an ear of a corn plant not comprising the same FEA2 mutation)) and yield (e.g., increased seed number).

CLV1, CLV2, and CLV3 genes are part of several overlapping signaling pathways that utilize a similar mechanism to regulate meristem size. Plants express many CLV3-like (CLE) peptides which are sensed by many leucine-rich repeat (LRR) domains, and the downstream signaling regulates a myriad of growth processes in the plant (Fletcher, J. C., Plants 7:87 (2018)). The CLV2 ortholog in maize is FASCIATED EAR2 (FEA2). Similar to FEA2, other CLV orthologues may be edited using the strategy described herein, thereby improving yield traits in a variety of plant species.

Thus, a plant of the present invention may comprise one or more improved yield traits that may include, but are not limited to, increased floral meristem size and/or increased kernel row number (KRN), optionally wherein the increase in KRN does not result in a substantial decrease in the length of the ear. Plants having increased kernel row number may further exhibit an increased yield.

As used herein, an "increased yield" means an increase in yield of about 15% to about 100% % (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% or any range or value therein) as compared to a control plant. An increase in yield may be measured by, for example, seed or kernel number, size or weight.

As used herein, "larger floral meristem" or a "floral meristem that is increased in size" refers to an increase in size of about 1% to about 20% (e.g., about 1, 2, 3, 4, 5, 6, 7, 8, 9, 10, 11, 12, 13, 14, 15, 16, 17, 18, 19, or 20%, or any range or value therein).

As used herein, an "increase in KRN" refers to an increase in KRN of about 5% to about 35% (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35%, or any range or value therein) as compared to a control plant.

As used herein, an "increase in kernel row number (KRN)" means an increase in the number of rows in an ear of at least about one to about ten (e.g., about 1, 2, 3, 4, 5, 6, 7, 8, 9, or 10 or more) as compared to a control plant that is devoid of the mutation as described herein, optionally wherein ear length is not substantially reduced. An "increase in KRN" refers to an increase in KRN of about 5% to about 50% (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% or any range or value therein; e.g., about 5% to about 10%, about 5% to about 15%, about 5% to about 20%, about 10% to about 50%, about 20% to about 50%, about 30% to about 50%, and any range or value therein) as compared to a control plant devoid of the mutated endogenous FEA2 gene.

As used herein, the phrase "ear length is not substantially reduced" can mean that the ear is not decreased in length by more than about 5, 6, 7, 8, 9, 10, 11, 12, 13, 14, 15, 16, 17, 18, 19, 20, 21, 22, 23, 24, 25, 26, 27, 28, 29, or 30%, or any range or value therein, as compared to an ear of a plant devoid of the same mutation(s). In some embodiments, an ear having increased KRN may have an ear length that is at least about 70% or more the length of an ear of a plant devoid of the same mutation(s) (e.g., at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% or any range or value therein).

Accordingly, as described herein, editing technology is used to target FEA2 genes in plants to generate plants with larger floral meristems, having increased kernel row number, and/or increased yield. Mutations that may be useful for production of plants exhibiting increased kernel row number include, for example, substitutions, deletions and insertions. In some aspects, a mutation generated by the editing technology can be a point mutation, a dominant negative mutation, a semi-dominant mutation, or a weak loss-of-function mutation.

In some embodiments, the invention provides a corn plant or plant part thereof, the corn plant or plant part comprising at least one mutation (e.g., 1, 2, 3, 4, or 5, or more mutations) in an endogenous FASCIATED EAR2 (FEA2) gene that encodes a FEA2 protein. In some embodiments, the endogenous FASCIATED EAR2 (FEA2) gene has a gene identification number (gene ID) of Zm00001d051012. In some embodiments, the at least one mutation may result in a dominant negative mutation and/or a weak loss-of-function mutation. In some embodiments, the at least one mutation may be a non-natural mutation.

A mutation in a FEA2 gene of the corn plant, plant part thereof or the corn plant cell may be any type of mutation, including a substitution, a deletion and/or an insertion. In some embodiments, a mutation may be a non-natural mutation. In some embodiments, a mutation may comprise a base substitution to an A, a T, a G, or a C. In some embodiments, a mutation may be a deletion of at least one base pair (e.g., 1 base pair to about 50 base pairs) or an insertion of at least one base pair (e.g., 1 base pair to about 50 base pairs). In some embodiments, a deletion may comprise 1 base pair to about 10 consecutive base pairs (e.g., 1, 2 bp to about 3, 4, 5, 6, 7, 8, 9, or 10 bp; e.g., 1, 2, 3, 4, 5, 6, 7, 8, 9, 10 consecutive base pairs), 1 base pair to about 20 consecutive base pairs (e.g., 1, 2, 3, 4, 56, 7, 8, 9, 101, 12, 13, 14, 15, 16, 17, 18, 19, or 20 consecutive base pairs; e.g., 1, 2 3, 4, 5, 6 bp to about 7, 8, 9, 10, 11, 12, 13, 14, 15, 16, 17, 18, 19, or 20 consecutive base pairs), 1 base pair to about 30 consecutive base pairs, 1 base pair to about 40 consecutive base pairs, 1 base pair to about 50 consecutive base pairs (e.g., 1, 2, 4, 5, 6, 7, 8, 9, 10, 11, 12, 13, 14, 15, 16, 17, 18, 19, 20, 21, 22, 23, 24, 25 consecutive base pairs to about 26, 27, 28, 29, 30, 31, 32, 33, 34, 35, 36, 37, 38, 39, 40, 41, 42, 43, 44, 45, 46, 47, 48, 49, 50 consecutive base pairs, or more, or any value or range therein of an FEA2 gene.

In some embodiments, the at least one mutation may be an out-of-frame deletion or insertion or an in-frame deletion or insertion, optionally resulting in a dominant negative mutation and/or a weak loss-of-function mutation. In some embodiments, the at least one mutation may be an out-of-frame deletion or an out-of-frame insertion that results in a dominant negative mutation and/or a weak loss-of-function mutation. In some embodiments, the at least one mutation may be an in-frame deletion or an in-frame insertion that results in a dominant negative mutation and/or a weak loss-of-function mutation. In some embodiments, the at least one mutation may be located in the 10th LRR repeat of the encoded FEA2 polypeptide. In some embodiments, the at least one mutation may result in a modified FEA2 polypeptide that is truncated. In some embodiments, the at least one mutation may be a base substitution that results in one or more amino acid substitutions. In some embodiments, the at least one mutation may result in a substituted amino acid residue located at or adjacent to position 332 of the encoded FEA2 polypeptide with reference to amino acid position numbering of SEQ ID NO:74, optionally a substitution of G332. As used herein, “adjacent to position 332” means that the at least one mutation (e.g., a substituted amino acid residue) may occur within about 15 consecutive amino acids of position 332 (toward the N-terminal end or toward the C-terminal end) with reference to amino acid position numbering of SEQ ID NO: 74, e.g., from about residue position 318 to about residue position 348; e.g., positions 317, 318, 319, 320, 321, 322, 323, 324, 325, 326, 327, 328, 329, 330, 331, 332, 333, 334, 335, 336, 337, 338, 339, 340, 341, 342, 343, 345, 346, 347 and/or 348 with reference to amino acid position numbering of SEQ ID NO:74.

An endogenous FEA2 gene useful with this invention may (a) comprise a nucleotide sequence having at least 90% sequence identity to SEQ ID NO:72 or SEQ ID NO:73, (b) comprise a region having at least 90% sequence identity to any one of the nucleotide sequences of SEQ ID NOs: 75-77, (c) encode an amino acid sequence having at least 90% sequence identity to SEQ ID NO:74, and/or (d) encode a polypeptide comprising a region having at least 90% sequence identity to any one of SEQ ID NOs: 78-80, optionally wherein the sequence identity of (a), (b), (c), and/or (d) may be at least 95%, optionally the sequence identity may be 100%. A mutation in an endogenous FEA2 gene may result in a mutated FEA2 polypeptide, optionally wherein the mutated FEA2 protein may exhibit altered ability to complex with other polypeptides, optionally wherein the mutated FEA2 protein may exhibit altered ability to transit the plasma membrane (e.g., when complexed with such proteins as CRN, an FEA2 modified as described herein has a reduced ability to locate to plasma membrane, thereby trapping the FEA2 in the ER). In some embodiments, a mutated FEA2 gene may comprise a nucleotide sequence having at least about 90% sequence identity to any one of SEQ ID NOs: 82, 84, 86, 88, 90, 92, 94, 96 or 98, optionally wherein the sequence identity may be at least 95%, optionally the sequence identity may be 100%.

In some embodiments, a corn plant comprising at least one mutation (e.g., non-natural mutation) in an endogenous FEA2 gene may exhibit increased maintenance of meristems and/or increased kernel row number as compared to a control corn plant without the at least one mutation (e.g., non-natural mutation), optionally without substantially decreasing ear length (e.g., a decrease of less than 30%, optionally having an ear length of at least 70% of a control ear). In some embodiments, the corn plant comprising at least one mutation in an endogenous FEA2 gene exhibits increased kernel row number. In some embodiments, the corn plant comprising at least one mutation in an endogenous FEA2 gene may exhibit increased yield. In some embodiments, a corn plant may be regenerated from a corn plant part and/or corn plant cell of the invention, wherein the regenerated corn plant comprises the mutated endogenous FEA2 gene and exhibits a phenotype of increased kernel row number as compared to a control corn plant not comprising the mutation, optionally wherein the length of the ear(s) having an increased kernel row number is not substantially decreased (e.g., exhibits a decrease in ear length of no more than 30% as compared to an ear of a corn plant not comprising the same FEA2 mutation, optionally an ear length of at least 70% of an ear of the control plant), optionally the regenerated corn plant further exhibits increased yield.

In some embodiments, a corn plant cell is provided, the corn plant cell comprising an editing system comprising: (a) a CRISPR-Cas effector protein; and (b) a guide nucleic acid (gRNA, gDNA, crRNA, crDNA, sgRNA, sgDNA) comprising a spacer sequence with complementarity to an endogenous target gene encoding a FEA2 protein. The editing system may be used to generate a mutation in the endogenous target gene encoding an FEA2 protein. In some embodiments, the mutation is a non-natural mutation. In some embodiments, a guide nucleic acid of an editing system may comprise the nucleotide sequence (a spacer sequence) of SEQ ID NO:81.

In some embodiments, a corn plant cell is provided, the corn plant cell comprising at least one mutation within a FEA2 gene, wherein the mutation is a substitution, an insertion or a deletion that is introduced using an editing system that comprises a nucleic acid binding domain that binds to a target site within the FEA2 gene. In some embodiments, the substitution, insertion, or deletion within a FEA2 gene results in a dominant negative allele or a weak loss-of-function allele. In some embodiments, the mutation may be a non-natural mutation. In some embodiments, the mutation may be a point mutation. In some embodiments, the target site is within a region of the FEA2 gene, the region comprising a sequence having at least 90% sequence identity (e.g., about 90, 91, 92, 93, 94, 95, 96, 97, 98, 99, 99.5, 99.6, 99.7, 99.8, 99.9, or 100% sequence identity) to the nucleotide sequence of any one of SEQ ID NOs: 75-77, optionally wherein the sequence identity may be at least 95% or it may be 100%, and/or encoding a sequence having at least 90% sequence identity (e.g., about 95, 96, 97, 98, 99, 99.5, 99.5, 99.6, 99.7, 99.8, 99.9, or 100% sequence identity) to the amino acid sequence of any one of SEQ ID NOs: 78-80, optionally wherein the sequence identity may be at least 95% or it may be 100%. In some embodiments, the editing system further comprises a nuclease, the nucleic acid binding domain binds to a target site within a sequence having at least 90% sequence identity to the nucleotide sequence of any one of SEQ ID NOs: 75-77, optionally wherein the sequence identity may be at least 95% or it may be 100%, and the at least one mutation within a FEA2 gene is made following cleavage by the nuclease. In some embodiments, the endogenous FEA2 gene comprises a sequence having at least 90% sequence identity to the nucleotide sequence of SEQ ID NO:72 or SEQ ID NO:73, optionally wherein the sequence identity may be at least 95% or it may be 100%, or encodes a sequence having at least 90% sequence identity to the amino acid sequence of SEQ ID NO:74, optionally wherein the sequence identity may be at least 95% or it may be 100%. In some embodiments, the mutation results in an amino acid substitution in the encoded polypeptide. In some embodiments, the mutation is an out-of-frame insertion or an out-of-frame deletion that results in a mutated FEA2 polypeptide, optionally wherein the mutation in the FEA2 polypeptide is in the 10th LRR.

In some embodiments, the least one mutation within a FEA2 gene in a corn plant cell may result in a modification of the ability of the encoded FEA2 polypeptide to complex with other polypeptides, and/or to transit from the endoplasmic reticulum to the plasma membrane after forming a protein complex with other proteins such as the pseudokinase, e.g., CORYNE (CRN) (e.g., a decreased ability of the FEA2 complex to interact with the export machinery for transfer from the ER to the plasma membrane) and/or the heterotrimeric G protein COMPACT PLANT2.

In some embodiments, a mutated FEA2 gene that is comprised in a corn plant cell may have at least 90% sequence identity to any one of SEQ ID NOs: 82, 84, 86, 88, 90, 92, 94, 96 or 98, optionally wherein the sequence identity may be at least 95%, optionally the sequence identity may be 100%.

In some embodiments, a corn plant cell or corn plant part comprising a mutated FEA2 gene as described herein may be regenerated into a corn plant comprising the mutated FEA2 gene, optionally comprising a mutated FEA2 polypeptide. In some embodiments, a corn plant part or corn plant cell comprising a mutated FEA2 gene as described herein is not regenerated into a corn plant.

In some embodiments, a method of producing/breeding a transgene-free edited corn plant is provided, the method comprising: crossing a corn plant of the present invention (e.g., a corn plant comprising a mutation in a FEA2 gene and having increased kernel row number, optionally without substantially decreasing ear length (e.g., a decrease of less than 30%)) with a transgene free corn plant, thereby introducing the at least one mutation into the corn plant that is transgene-free; and selecting a progeny corn plant that comprises the at least one mutation and is transgene-free, thereby producing a transgene free edited corn plant. In some embodiments, a method of providing a plurality of corn plants having increased kernel row number is provided, the method comprising planting two or more corn plants of the invention (e.g., 2, 3, 4, 5, 6, 7, 8, 9, 10, 20, 30, 40, 50, 100, 200, 300, 400, 500, 1000, 2000, 3000, 400, 5000, or 10,000 or more corn plants comprising a mutation in a FEA2 polypeptide and having increased kernel row number, optionally without having substantially decreased ear length (e.g., a decrease of less than 30%)) in a growing area (e.g., a field (e.g., a cultivated field, an agricultural field), a growth chamber, a greenhouse, a recreational area, a lawn, and/or a roadside and the like), thereby providing a plurality of corn plants having increased kernel row number as compared to a plurality of control corn plants not comprising the mutation. In some embodiments, the plurality of corn plants may also exhibit larger floral meristems and/or increased yield.

In some embodiments, a method of generating variation in a region of a corn FEA2 polypeptide is provided, comprising introducing an editing system into a corn plant cell, wherein the editing system is targeted to a region of an FEA2 gene that encodes a FEA2 polypeptide, and contacting the region of the FEA2 gene with the editing system, thereby introducing a mutation into the FEA2 gene and generating variation in the region of a corn FEA2 polypeptide of the corn plant cell. In some embodiments, the FEA2 gene: (a) comprises a nucleotide sequence having at least 90% sequence identity to SEQ ID NO:72 or SEQ ID NO: 73, (b) comprises a region having at least 90% sequence identity to any one of the nucleotide sequences of SEQ ID NOs: 75-77, (c) encodes an amino acid sequence having at least 90% sequence identity to SEQ ID NO:74, and/or (d) encodes a polypeptide comprising a region having at least 90% sequence identity to any one of SEQ ID NOs: 78-80, optionally wherein the sequence identity of (a), (b), (c), and/or (d) may be at least 95%, optionally the sequence identity may be 100%. In some embodiments, the region of the FEA2 gene that is targeted comprises at least 90% sequence identity to any one of the nucleotide sequences of SEQ ID NOs: 75-77, optionally wherein the sequence identity may be at least 95%, optionally the sequence identity may be 100%. In some embodiments, contacting the region of the endogenous FEA2 gene in the corn plant cell with the editing system produces a corn plant cell comprising in its genome an edited endogenous FEA2 gene and the method further comprises (a) regenerating a corn plant from the corn plant cell; (b) selfing the corn plant to produce corn progeny plants (E1); (c) assaying the progeny plants of (b) for increased yield and/or increase kernel row number (optionally wherein when kernel row number is increased, ear length is not substantially reduced); and (d) selecting the progeny corn plants exhibiting increased yield and/or increase kernel row number (optionally wherein when kernel row number is increased, ear length is not substantially reduced) to produce selected progeny corn plants exhibiting increased yield and/or increase kernel row number (optionally wherein when kernel row number is increased, ear length is not substantially reduced) as compared to a control corn plant. In some embodiments, the method may further comprise (e) selfing the selected progeny corn plants of (d) to produce progeny corn plants (E2); (f) assaying the progeny corn plants of (e) for increased yield and/or increase kernel row number (optionally wherein when kernel row number is increased, ear length is not substantially reduced); and (g) selecting the progeny corn plants exhibiting increased yield and/or increase kernel row number (optionally wherein when kernel row number is increased, ear length is not substantially reduced) to produce selected progeny corn plants exhibiting increased yield and/or increase kernel row number (optionally wherein when kernel row number is increased, ear length is not substantially reduced) as compared to a control corn plant, optionally repeating (e) through (g) one or more additional times.

In some embodiments, the invention provides a method of detecting a mutant FEA2 gene (detecting a mutation in an endogenous FEA2 gene) in a corn plant, the method comprising detecting in the genome of the corn plant a FEA2 gene having at least one mutation in a region having at least 90% sequence identity to any one of the nucleotide sequences of SEQ ID NOs: 75-77, optionally wherein the sequence identity may be at least 95%, optionally the sequence identity may be 100%. In some embodiments, the mutant FEA2 gene that is detected may comprise a mutated nucleotide sequence as described herein.

In some embodiments, a method for editing a specific site in the genome of a corn plant cell is provided, the method comprising: cleaving, in a site specific manner, a target site within an endogenous FEA2 gene in the corn plant cell, the endogenous FEA2 gene (a) comprising a nucleotide sequence having at least 90% sequence identity to SEQ ID NO:72 or SEQ ID NO: 73, (b) comprising a region having at least 90% sequence identity to any one of the nucleotide sequences of SEQ ID NOs: 75-77, (c) encoding an amino acid sequence having at least 90% sequence identity to SEQ ID NO:74, and/or (d) encoding a polypeptide comprising a region having at least 90% sequence identity to any one of SEQ ID NOs: 78-80, optionally wherein the sequence identity of (a), (b), (c), and/or (d) may be at least 95%, optionally the sequence identity may be 100%, thereby generating an edit in the endogenous FEA2 gene of the corn plant cell and producing a corn plant cell comprising the edit in the endogenous FEA2 gene. The endogenous FEA2 gene encodes a FEA2 protein and the edit results in variation of amino acids in the coding region of the FEA2 protein, e.g., the edit results in an amino acid substitution in the encoded FEA2 polypeptide. In some embodiments, the edit results in a deletion, substitution, or insertion, optionally, wherein the deletion, substitution, or insertion may be a dominant negative allele or a weak loss-of-function allele. In some embodiments, the edit results in a mutation that is an out-of-frame deletion or an out-of-frame insertion. In some embodiments, the target site comprises a sequence having at least 90% sequence identity to the nucleotide sequence of any one of SEQ ID NOs: 75-77, optionally wherein the sequence identity may be at least 95%, optionally the sequence identity may be 100% or comprises a sequence that encodes an amino acid sequence having at least 90% sequence identity to any one of SEQ ID NOs: 78-80, optionally wherein the sequence identity may be at least 95%, optionally the sequence identity may be 100%. In some embodiments, the edit results an amino acid substitution at residue 332 with reference to amino acid position numbering of SEQ ID NO:74, optionally wherein the edit results in a substitution of G332. In some embodiments, the edit is located at or adjacent to residue 332 with reference to amino acid position numbering of SEQ ID NO:74, optionally wherein the edit results in an out-of-frame deletion or an out-of-frame insertion. In some embodiments, the mutation alters the ability of the FEA2 polypeptide to complex with other proteins and/or, when the FEA2 polypeptide is complexed with another protein such as the pseudokinase CORYNE (CRN), the mutation alters the ability of the FEA2 polypeptide to transit to the plasma membrane from the endoplasmic reticulum (ER) (e.g., FEA2 when complexed with such polypeptides as CRN is trapped in the ER). In some embodiments, the edit results in a non-natural mutation, optionally resulting in a mutated FEA2 gene comprising a nucleotide sequence having at least 90% sequence identity to the nucleotide sequence of any one of SEQ ID NOs: 82, 84, 86, 88, 90, 92, 94, 96 or 98, optionally wherein the sequence identity may be at least 95%, optionally the sequence identity may be 100%.

In some embodiments, a method of editing may further comprise regenerating a corn plant from the corn plant cell comprising the edit in the endogenous FEA2 gene, thereby producing a corn plant comprising the edit in its endogenous FEA2 gene and having a phenotype of increased kernel row number (e.g., producing one or more ears having an increased kernel row number) when compared to a control corn plant that does not comprise the edit, optionally wherein the length of the one or more ears having an increased kernel row number is not substantially decreased, optionally wherein the corn plant exhibits increased yield when compared to a control corn plant that does not comprise the edit.

In some embodiments, a method for making a corn plant is provided, comprising: (a) contacting a population of corn plant cells comprising an endogenous FEA2 gene with a nuclease linked to a nucleic acid binding domain (e.g., DNA binding domain, e.g., editing system) that binds to a sequence having at least 90% sequence identity to the nucleotide sequence of any one of SEQ ID NOs: 75-77 (optionally, wherein the sequence identity may be at least 95%, or it may be 100%) or to a region of a sequence that encodes an amino acid sequence having at least 90% sequence identity to any one of SEQ ID NOs: 78-80 (optionally, wherein the sequence identity may be at least 95%, or it may be 100%); (b) selecting a corn plant cell from the population in which an endogenous FEA2 gene has been mutated, thereby producing a corn plant cell comprising at least one mutation in the endogenous FEA2 gene; and (c) growing the selected corn plant cell into a corn plant.

In some embodiments, a method increasing kernel row number in a corn plant is provided, optionally without decreasing ear length, the method comprising (a) contacting a corn plant cell comprising an endogenous FEA2 gene with a nuclease targeting the endogenous FEA2 gene, wherein the nuclease is linked to a nucleic acid binding domain (e.g., editing system) that binds to a target site in endogenous FEA2 gene, wherein the endogenous FEA2 gene: (i) comprises a nucleotide sequence having at least 90% sequence identity to the sequence of SEQ ID NO:72 or SEQ ID NO:73; (ii) encodes an amino acid sequence having at least 90% sequence identity to the sequence of SEQ ID NO:74; (iii) comprises a region having at least 90% sequence identity to the nucleotide sequence of any one of SEQ ID NOs: 75-11770; and/or (iv) encodes a region of a polypeptide comprising a region having at least 90% sequence identity to the amino acid sequence of any one of SEQ ID NOs: 78-80, optionally wherein the sequence identity of (i), (ii), (iii), and/or (iv) may be at least 95%, optionally the sequence identity may be 100%, to produce a corn plant cell comprising a mutation in the endogenous FEA2 gene; and (b) growing the corn plant cell into a corn plant comprising the mutation in the endogenous FEA2 gene, thereby producing a corn plant have a mutated endogenous FEA2 gene and exhibiting increased yield and/or an increased kernel row number, optionally exhibiting an increased kernel row number without substantially reducing ear length, optionally wherein ear length is not substantially decreased (e.g., a decrease of less than 30%).

In some embodiments, a method is provided for producing a corn plant or part thereof comprising at least one cell having a mutated endogenous FEA2 gene, the method comprising contacting a target site within an endogenous FEA2 gene in the corn plant or plant part with a nuclease comprising a cleavage domain and a nucleic acid binding domain (e.g., DNA binding domain), wherein the nucleic acid binding domain binds to a target site in the endogenous FEA2 gene, wherein the endogenous FEA2 gene (a) comprises a nucleotide sequence having at least 90% sequence identity to the sequence of SEQ ID NO:72 or SEQ ID NO:73; (b) encodes an amino acid sequence having at least 90% sequence identity to the sequence of SEQ ID NO: 74; (c) comprises a region having at least 90% sequence identity to the nucleotide sequence of any one of SEQ ID NOs: 75-77; and/or (d) encodes a region of a polypeptide comprising a region having at least 90% sequence identity to the amino acid sequence of any one of SEQ ID NO:78-80, optionally wherein the sequence identity of (a), (b), (c), and/or (d) may be at least 95%, optionally the sequence identity may be 100%, thereby producing the corn plant or part thereof comprising at least one cell having a mutation in the endogenous FEA2 gene.

Also provided herein is a method for producing a corn plant or part thereof comprising a mutated endogenous FEA2 gene and exhibiting increased kernel row number increased yield, and larger floral meristems, the method comprising contacting a target site in an endogenous FEA2 gene in the corn plant or plant part with a nuclease comprising a cleavage domain and a nucleic acid binding domain, wherein the nucleic acid binding domain binds to a target site in the endogenous FEA2 gene, wherein the endogenous FEA2 gene: (a) comprises a nucleotide sequence having at least 90% sequence identity to the sequence of SEQ ID NO:72 or SEQ ID NO: 73; (b) encodes an amino acid sequence having at least 90% sequence identity to the sequence of SEQ ID NO:74; (c) comprises a region having at least 90% sequence identity to the nucleotide sequence of any one of SEQ ID NOs: 75-77; and/or (d) encodes a region of a polypeptide comprising a region having at least 90% sequence identity to the amino acid sequence of any one of SEQ ID NOs: 78-80, optionally wherein the sequence identity of (a), (b), (c), and/or (d) may be at least 95%, optionally the sequence identity may be 100%, thereby producing the corn plant or part thereof comprising an endogenous FEA2 gene having a mutation and exhibiting increased kernel row number (e.g., producing one or more ears having an increased kernel row number) as compared to a control corn plant not comprising the mutation, optionally wherein the length of the one or more ears having an increased kernel row number is not substantially decreased (e.g., a decrease of less than 30%). In some embodiments, the corn plant may further exhibit increased yield as compared to a control corn plant not comprising the mutation.

In some embodiments, a nuclease contacting a corn plant cell, a population of corn plant cells and/or a target site cleaves an endogenous FEA2 gene, thereby introducing a mutation into the endogenous FEA2 gene. In some embodiments, a nuclease useful with the invention may cleave an endogenous FEA2 gene, thereby introducing a mutation into the endogenous FEA2 gene. In some embodiments, the nuclease can include, but is not limited to a zinc finger nuclease, transcription activator-like effector nucleases (TALEN), endonuclease (e.g., Fok1) and/or a CRISPR-Cas effector protein. Likewise, a nucleic acid binding domain (e.g., DNA binding domain, RNA binding domain) useful with the invention may be any nucleic acid binding domain that may be utilized to edit/modify a target nucleic acid. Such nucleic acid binding domains include, but are not limited to, a zinc finger, transcription activator-like DNA binding domain (TAL), an argonaute and/or a CRISPR-Cas effector DNA binding domain.

In some embodiments, a corn plant or part thereof comprising at least one cell having a mutation in an endogenous FEA2 gene as described herein comprises a sequence having at least 90% identity to any one of SEQ ID NOs: 82, 84, 86, 88, 90, 92, 94, 96 or 98, and/or encodes a mutated FEA2 polypeptide having at least 90% sequence identity to any one of SEQ ID NOs: 83, 85, 87, 89, 91, 93, 95, 97, or 99, optionally wherein the sequence identity may be at least 95%, optionally the sequence identity may be 100%.

In some embodiments, a method is provided for modifying an endogenous FEA2 gene in a corn plant or part thereof for improving a yield trait in the corn plant or part thereof, the method comprising modifying a target site within the endogenous FEA2 gene in the corn plant or a part thereof, wherein the endogenous FEA2 gene: (a) comprises a sequence having at least 90% sequence identity to the nucleotide sequence of SEQ ID NO:72 or SEQ ID NO:73; (b) comprises a region having at least 90% sequence identity to any one of the nucleotide sequences of SEQ ID NOs: 75-77; (c) encodes a polypeptide comprising a sequence having at least 90% sequence identity to the amino acid sequence of SEQ ID NO:74; and/or (d) encodes a region of a polypeptide comprising a region having at least 90% sequence identity to the amino acid sequence of SEQ ID NO:78-80, optionally wherein the sequence identity of (a), (b), (c), and/or (d) may be at least 95%, optionally the sequence identity may be 100%, thereby modifying the endogenous FEA2 gene and improving a yield trait in the corn plant or part thereof.

In some embodiments, a method of editing an endogenous FEA2 gene in a corn plant or plant part is provided, the method comprising contacting a target site in an FEA2 gene in the corn plant or plant part with a cytosine base editing system comprising a cytosine deaminase and a nucleic acid binding domain that binds to a target site in the FEA2 gene, wherein the FEA2 gene (a) comprises a nucleotide sequence having at least 90% sequence identity to the sequence of SEQ ID NO:72 or SEQ ID NO:73; (b) encodes an amino acid sequence having at least 90% sequence identity to the sequence of SEQ ID NO:74; (c) comprises a region having at least 90% sequence identity to the nucleotide sequence of any one of SEQ ID NOs: 75-77; and/or (d) encodes a region of a polypeptide comprising a region having at least 90% sequence identity to the amino acid sequence of any one of SEQ ID NOs: 78-80, thereby editing the endogenous FEA2 gene in the corn plant or part thereof and producing a corn plant or part thereof comprising at least one cell having a mutation in the endogenous FEA2 gene.

In some embodiments, a method of editing an endogenous FEA2 gene in a corn plant or plant part is provided, the method comprising contacting a target site in an FEA2 gene in the corn plant or plant part with an adenosine base editing system comprising an adenosine deaminase and a nucleic acid binding domain that binds to a target site in the FEA2 gene, wherein the FEA2 gene (a) comprises a nucleotide sequence having at least 90% sequence identity to the sequence of SEQ ID NO:72 or SEQ ID NO:73; (b) encodes an amino acid sequence having at least 90% sequence identity to the sequence of SEQ ID NO:74; (c) comprises a region having at least 90% sequence identity to the nucleotide sequence of any one of SEQ ID NOs: 75-77; and/or (d) encodes a region of a polypeptide comprising a region having at least 90% sequence identity to the amino acid sequence of any one of SEQ ID NOs: 78-80, thereby editing the endogenous FEA2 gene in the corn plant or part thereof and producing a corn plant or part thereof comprising at least one cell having a mutation in the endogenous FEA2 gene.

In some embodiments, a method of creating a mutation in an endogenous FEA2 gene in a corn plant is provided, the method comprising: (a) targeting a gene editing system to a portion of the FEA2 gene that comprises a sequence having at least 90% sequence identity to any one of SEQ ID NOs: 75-77; and (b) selecting a corn plant that comprises a modification located in a region of the FEA2 gene having at least 90% sequence identity to any one of SEQ ID NOs: 75-77, optionally wherein the sequence identity of (a) and/or (b) may be at least 95%, optionally the sequence identity may be 100%.

In some embodiments, a mutation in an endogenous FEA2 gene edited as described herein results in a sequence having at least 90% identity to any one of SEQ ID NOs: 82, 84, 86, 88, 90, 92, 94, 96 or 98, optionally wherein the sequence identity may be at least 95%, optionally the sequence identity may be 100%, and/or encodes a mutated FEA2 polypeptide having at least 90% sequence identity to any one of SEQ ID NOs: 83, 85, 87, 89, 91, 93, 95, 97, or 99, optionally wherein the sequence identity may be at least 95%, optionally the sequence identity may be 100%.

In some embodiments, a method of detecting a mutant FEA2 gene (a mutation in an endogenous FEA2 gene) is provide, the method comprising detecting in the genome of the corn plant a FEA2 gene having at least one mutation in a region having at least 90% sequence identity to any one of the nucleotide sequences of SEQ ID NOs: 75-77, optionally wherein the sequence identity may be at least 95%, optionally the sequence identity may be 100%.

In some embodiments, a method of detecting a mutant FEA2 gene (a mutation in an endogenous FEA2 gene) is provide, the method comprising detecting in the genome of a corn plant a mutation in a nucleic acid encoding the amino acid sequence of SEQ ID NO:74, wherein the mutation is located in the 10th LRR of the encoded polypeptide.

In some embodiments, a method of detecting a mutant FEA2 gene (a mutation in an endogenous FEA2 gene) is provide, the method comprising detecting in the genome of a corn plant a mutation in a nucleic acid encoding the amino acid sequence of SEQ ID NO:74, wherein the mutation is located at or adjacent to amino acid residue 332 with reference to amino acid position numbering of SEQ ID NO:74.

In some embodiments, a method of detecting a mutation in an endogenous FEA2 gene is provided, comprising detecting in the genome of a corn plant a mutated FEA2 gene. In some embodiments, the mutated FEA2 gene comprises a sequence having at least 90% sequence identity to any one of SEQ ID NOs: 82, 84, 86, 88, 90, 92, 94, 96 or 98, optionally wherein the sequence identity may be at least 95%, optionally the sequence identity may be 100%, and/or encodes a mutated FEA2 polypeptide having at least 90% sequence identity to any one of SEQ ID NOs: 83, 85, 87, 89, 91, 93, 95, 97, or 99, optionally wherein the sequence identity may be at least 95%, optionally the sequence identity may be 100%.

In some embodiments, a method of producing a corn plant comprising a mutation in an endogenous FEA2 gene and at least one polynucleotide of interest is provided, the method comprising crossing a corn plant of the invention comprising at least one mutation in an endogenous FEA2 gene (a first plant) with a second plant that comprises the at least one polynucleotide of interest to produce progeny plants; and selecting progeny plants comprising at least one mutation in the FEA2 gene and the at least one polynucleotide of interest, thereby producing the corn plant comprising a mutation in an endogenous FEA2 gene and at least one polynucleotide of interest.

In some embodiments, the present invention provides a method of producing a corn plant comprising a mutation in an endogenous FEA2 gene and at least one polynucleotide of interest, the method comprising introducing at least one polynucleotide of interest into a corn plant of the invention comprising at least one mutation in an endogenous FEA2 gene, thereby producing a corn plant comprising at least one mutation in a FEA2 gene and at least one polynucleotide of interest.

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, disease resistance, increased yield, increased nutrient use efficiency or abiotic stress resistance.

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, nematode resistance, disease resistance, increased yield, increased nutrient use efficiency or abiotic stress resistance.

Thus, plants or plant cultivars which are to be treated with preference in accordance with the invention include all plants which, through genetic modification, received genetic material which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

Further examples of such properties are an increased resistance against animal and microbial pests, such as against insects, arachnids, nematodes, mites, slugs and snails owing, for example, to toxins formed in the plants. Among DNA sequences encoding proteins which confer properties of tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the CryIA, CryIAb, CryIAc, CryIIA, CryIIIA, CryIIIB2, Cry9c Cry2Ab, Cry3Bb and CryIF proteins or toxic fragments thereof and also hybrids or combinations thereof, especially the CryIF protein or hybrids derived from a CryIF protein (e.g. hybrid CryIA-CryIF proteins or toxic fragments thereof), the CryIA-type proteins or toxic fragments thereof, preferably the CryIAc protein or hybrids derived from the CryIAc protein (e.g. hybrid CryIAb-CryIAc proteins) or the CryIAb or Bt2 protein or toxic fragments thereof, the Cry2Ae, Cry2Af or Cry2Ag proteins or toxic fragments thereof, the CryIA. 105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), Proc Natl Acad Sci US A. 28; 93 (11): 5389-94, the Cry proteins as described in WO2001/47952, the insecticidal proteins from Xenorhabdus (as described in WO98/50427), *Serratia* (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins (i.e., polynucleotides of interest) which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-Synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g., WO2007/024782), a mutated *Arabidopsis* ALS/AHAS gene (e.g., U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further examples of such properties are increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated with preference in accordance with the invention include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US-A 2005-216969); Event 3006-210-23 (cotton, insect control-herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control-herbicide tolerance, deposited as ATCC PTA-11508, described in WO 11/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLRL (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480);); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control-herbicide tolerance, deposited as ATCC PTA 11384, described in US-A 2006-070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLINL (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR 162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait-herbicide tolerance, deposited as ATCC PTA-9241, described in US-A 2010-0080887 or WO2010/037016); Event MON87708 (soybean, herbicide tolerance, deposited as ATCC PTA- 9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control-herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MSL 1 (oilseed rape, pollination control-herbicide tolerance, deposited as ATCC PTA-850 or PTA-2485, described in WO2001/031042); Event MS8 (oilseed rape, pollination control-herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control-herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHTOH2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control-herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control-herbicide tolerance, not deposited, described in US-A 2005-039226 or WO2004/099447); Event VIP1034 (corn, insect control-herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession N° PTA-11041) optionally stacked with event EE-GM1/LL27 or event EE-GM2/LL55 (WO2011/063413A2), event DAS-68416-4 (soybean, herbicide tolerance, ATCC Accession N° PTA-10442, WO2011/066360A1), event DAS-68416-4 (soybean, herbicide tolerance, ATCC Accession N° PTA-10442, WO2011/066384A1), event DP-040416-8 (corn, insect control, ATCC Accession N° PTA-11508, WO2011/075593A1), event DP-043A47-3 (corn, insect control, ATCC Accession N° PTA-11509, WO2011/075595A1), event DP-004114-3 (corn, insect control, ATCC Accession N° PTA-11506, WO2011/084621A1), event DP-032316-8 (corn, insect control, ATCC Accession N° PTA-11507, WO2011/084632A1), event MON-88302-9 (oilseed rape, herbicide tolerance, ATCC Accession N° PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession N°. PTA-10296, WO2012/051199A2), event DAS-44406-6 (soybean, stacked herbicide tolerance, ATCC Accession N°. PTA-11336, WO2012/075426A1), event DAS-14536-7 (soybean, stacked herbicide tolerance, ATCC Accession N°. PTA-11335, WO2012/075429A1), event SYN-000H2-5 (soybean, herbicide tolerance, ATCC Accession N°. PTA-11226, WO2012/082548A2), event DP-061061-7 (oilseed rape, herbicide tolerance, no deposit N° available, WO2012071039A1), event DP-073496-4 (oilseed rape, herbicide tolerance, no deposit N° available, US2012131692), event 8264.44.06.1 (soybean, stacked herbicide tolerance, Accession N° PTA-11336, WO2012075426A2), event 8291.45.36.2 (soybean, stacked herbicide tolerance, Accession N°. PTA-11335, WO2012075429A2), event SYHTOH2 (soybean, ATCC Accession N°. PTA-11226, WO2012/082548A2), event MON88701 (cotton, ATCC Accession N° PTA-11754, WO2012/134808A1), event KK179-2 (alfalfa, ATCC Accession N° PTA-11833, WO2013/003558A1), event pDAB8264.42.32.1 (soybean, stacked herbicide tolerance, ATCC Accession N° PTA-11993, WO2013/010094A1), event MZDT09Y (corn, ATCC Accession N° PTA-13025, WO2013/012775A1).

The genes/events (e.g., polynucleotides of interest), which impart the desired traits in question, may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETER, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEND™, INTACTA RR2 PRO®, VISTIVE GOLD®, and/or XTENDFLEX™ trade names.

An FEA2 gene useful with this invention includes any FEA2 gene in which a mutation as described herein can confer increased kernel row number and optionally, increased yield, in a corn plant or part thereof comprising the mutation. In some embodiments, an FEA2 polypeptide comprises an amino acid sequence having at least 90% identity (e.g., about 90, 91, 92, 93, 94, 95, 96, 97, 98, 99, 99.5, 100% sequence identity, optionally wherein the sequence identity may be at least 95% sequence identity or 100% sequence identity) to SEQ ID NO:74 or comprising a region having at least 90% sequence identity to the amino acid sequence of any one of SEQ ID NOs: 78-80 within the FEA2 polypeptide. In some embodiments, a FEA2 gene may comprise a sequence having at least about 90% sequence identity (e.g., about 90, 91, 92, 93, 94, 95, 96, 97, 98, 99, 99.5, 100% sequence identity, optionally wherein the sequence identity may be at least 95% sequence identity or 100% sequence identity) to the nucleotide sequence of SEQ ID NO:72 or SEQ ID NO:73, or the FEA2 gene comprises within it a sequence (a region or portion) having at least 90% identity (e.g., about 90, 91, 92, 93, 94, 95, 96, 97, 98, 99, 99.5, 100% sequence identity, optionally wherein the sequence identity may be at least 95% sequence identity or 100% sequence identity) to any one of the nucleotide sequences of SEQ ID NO:75-77.

In some embodiments, an at least one mutation generated in an endogenous FEA2 gene in a corn plant may be a substitution, a deletion and/or an insertion. In some embodiments, the at least one mutation in an endogenous FEA2 gene in a corn plant may be a substitution, a deletion and/or an insertion that results in a dominant negative mutation or a weak loss-of-function mutation, optionally wherein the corn plant comprising the mutation may exhibit a phenotype of increased kernel row number (e.g., a phenotype of producing ears having increased kernel row number) and/or increased yield as compared to a control corn plant not comprising the edit/mutation, optionally wherein the ears having increased kernel row number do not have a substantially decreased length (e.g., a decrease of less than 30% as compared to a corn plant not comprising the same FEA2 mutation). For example, the mutation may be a substitution, a deletion and/or an insertion of one or more amino acid residues (e.g., 1, 2, 3, 4, 5, 6, 7, 8, 9, 10 or more amino acids of the FEA2 polypeptide) or the mutation may be a substitution, a deletion and/or an insertion of at least 1 nucleotide to about 50 consecutive nucleotides (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 consecutive nucleotides, or any range or value therein) (e.g., a base substitution, deletion and/or insertion) in the gene encoding the FEA2 polypeptide. In some embodiments, the mutation may be a point mutation. In some embodiments, the at least one mutation may be a base substitution to an A, a T, a G, or a C. In some embodiments, a mutation or edit may be an out-of-frame insertion or deletion and/or may result in one or more than one amino acid substitution. In some embodiments, a mutation or edit in an FEA2 gene may modify the ability of the mutated FEA2 polypeptide to complex with other proteins, and/or when the FEA2 polypeptide is complexed with another protein, such as the pseudokinase CORYNE (CRN), the mutation alters the ability of the FEA2 polypeptide to transit to the plasma membrane from the ER (e.g., FEA2 when complexed with such polypeptides as CRN is trapped in the ER) . . .

In some embodiments, a mutation generated by the methods of the invention results in a mutated FEA2 gene comprising an edited nucleotide sequence having at least 90% sequence identity to any one of SEQ ID NOs: 82, 84, 86, 88, 90, 92, 94, 96 or 98, optionally wherein the sequence identity may be at least 95%, optionally the sequence identity may be 100%, and/or encodes a mutated FEA2 polypeptide having at least 90% sequence identity to any one of SEQ ID NOs: 83, 85, 87, 89, 91, 93, 95, 97, or 99, optionally wherein the sequence identity may be at least 95% sequence identity or 100% sequence identity.

In some embodiments, a mutation in an endogenous FEA2 gene may be made following cleavage by an editing system that comprises a nuclease and a nucleic acid binding domain (e.g., DNA binding domain) that binds to a target site within a target nucleic acid (e.g., a FEA2 gene), wherein the target nucleic acid: (a) comprises a nucleotide sequence having at least 90% sequence identity to the sequence of SEQ ID NO:72 or SEQ ID NO:73; (b) encodes an amino acid sequence having at least 90% sequence identity to the sequence of SEQ ID NO: 74; (c) comprises a region having at least 90% sequence identity to the nucleotide sequence of any one of SEQ ID NOs: 75-77; and/or (d) encodes a region of a polypeptide comprising a region having at least 90% sequence identity to the amino acid sequence of any one of SEQ ID NOs: 78-80, optionally wherein the sequence identity of (a), (b), (c), and/or (d) may be at least 95%, optionally the sequence identity may be 100%. In some embodiments, the nuclease cleaves the endogenous FEA2 gene, and a mutation is introduced into the endogenous FEA2 gene. In some embodiments, the mutation that is made by the editing system may result in one or more than one amino acid substitution. In some embodiments, the mutation may modify the ability of the FEA2 polypeptide to complex with other proteins. In some embodiments, the mutation may modify the ability of the FEA2 polypeptide when complexed with another protein such as the pseudokinase CORYNE (CRN) to transit to the plasma membrane from the endoplasmic reticulum (ER) (e.g., FEA2 when complexed with such polypeptides as CRN is trapped in the ER). In some embodiments, the mutation may be an out-of-frame mutation (e.g., an out-of-frame deletion or insertion). In some embodiments, the mutation may result in a substitution of one or more amino acid residue(s) optionally a substitution of a residue located at position 332 with reference to amino acid position numbering of SEQ ID NO:74. In some embodiments, the mutation is located in the 10th LRR of the FEA2 polypeptide. In some embodiments, the mutation is located at or near residue 332 of the FEA2 polypeptide with reference to amino acid position numbering of SEQ ID NO:74. In some embodiments, the cleavage results in a mutated endogenous FEA2 gene comprising a sequence having at least 90% identity to any one of SEQ ID NOs: 82, 84, 86, 88, 90, 92, 94, 96 or 98, optionally wherein the sequence identity may be at least 95%, optionally the sequence identity may be 100%, and/or encoding a mutated FEA2 polypeptide having at least 90% sequence identity to any one of SEQ ID NOs: 83, 85, 87, 89, 91, 93, 95, 97, or 99, optionally wherein the sequence identity may be at least 95%, optionally the sequence identity may be 100%.

A nuclease useful with this invention may cleave an endogenous FEA2 gene, thereby introducing a mutation into the endogenous FEA2 gene. Such nucleases include, but are not limited to a zinc finger nuclease, transcription activator-like effector nucleases (TALEN), endonuclease (e.g., Fok1) and/or a CRISPR-Cas effector protein. Likewise, a nucleic acid binding domain (e.g., DNA binding domain, RNA binding domain) useful with the invention includes any nucleic acid binding domain that can be utilized to edit/modify a target nucleic acid. Such nucleic acid binding domains include, but are not limited to, a zinc finger, transcription activator-like DNA binding domain (TAL), an argonaute and/or a CRISPR-Cas effector DNA binding domain.

Further provided herein are guide nucleic acids (e.g., gRNA, gDNA, crRNA, crDNA) that bind to a target site within and endogenous FEA2 gene, wherein the endogenous FEA2 gene: (a) comprises a nucleotide sequence having at least 90% sequence identity to the sequence of SEQ ID NO:72 or SEQ ID NO:73; (b) encodes an amino acid sequence having at least 90% sequence identity to the sequence of SEQ ID NO:74; (c) comprises a region having at least 90% sequence identity to the nucleotide sequence of any one of SEQ ID NOs: 75-77; and/or (d) encodes a region of a polypeptide comprising a region having at least 90% sequence identity to the amino acid sequence of any one of SEQ ID NOs: 78-80. In some embodiments, the target site may be a region in any one of the nucleotide sequences of SEQ ID NOs: 75-77 or in a region of a nucleotide sequence that encodes a region having the amino acid sequence of any one of SEQ ID NOs: 78-80, optionally wherein the sequence identity of (a), (b), (c), and/or (d) may be at least 95%, optionally the sequence identity may be 100%. In some embodiments, a guide nucleic acid is provided that binds to a target nucleic acid in a FASCIATED EAR2 (FEA2) gene in a corn plant, wherein the FEA2 gene has the gene identification number (gene ID) of Zm00001d051012. In some embodiments, a guide nucleic acid comprises a spacer having the nucleotide sequence of SEQ ID NOs: 81.

In some embodiments, a system is provided that comprises a guide nucleic acid of the invention and a CRISPR-Cas effector protein that associates with the guide nucleic acid. In some embodiments, a system is provided comprising a guide nucleic acid comprising a spacer having the nucleotide sequence of SEQ ID NOs: 81 and a CRISPR-Cas effector protein that associates with the guide nucleic acid. In some embodiments, the system may further comprise a tracr nucleic acid that associates with the guide nucleic acid and a CRISPR-Cas effector protein, optionally wherein the tracr nucleic acid and the guide nucleic acid are covalently linked.

In some embodiments, further provided is a gene editing system comprising a CRISPR-Cas effector protein in association with a guide nucleic acid and the guide nucleic acid comprises a spacer sequence that binds to a FEA2 gene, wherein the FEA2 gene (a) comprises a nucleotide sequence having at least 90% sequence identity to the sequence of SEQ ID NO: 72 or SEQ ID NO:73; (b) encodes an amino acid sequence having at least 90% sequence identity to the sequence of SEQ ID NO:74; (c) comprises a region having at least 90% sequence identity to the nucleotide sequence of any one of SEQ ID NOs: 75-77; and/or (d) encodes a region of a polypeptide comprising a region having at least 90% sequence identity to the amino acid sequence of any one of SEQ ID NOs: 78-80, optionally wherein the sequence identity of (a), (b), (c), and/or (d) may be at least 95%, optionally the sequence identity may be 100%. In some embodiments, a spacer sequence of the guide nucleic acid may comprise the nucleotide sequence of SEQ ID NO:81. In some embodiments, the gene editing system may further comprise a tracr nucleic acid that associates with the guide nucleic acid and a CRISPR-Cas effector protein, optionally wherein the tracr nucleic acid and the guide nucleic acid are covalently linked.

As used herein, "a CRISPR-Cas effector protein in association with a guide nucleic acid" refers to the complex that is formed between a CRISPR-Cas effector protein and a guide nucleic acid in order to direct the CRISPR-Cas effector protein to a target site in a gene.

In some embodiments, a complex is provided comprising a guide nucleic acid and a CRISPR-Cas effector protein comprising a cleavage domain, wherein the guide nucleic acid binds to a target site in an endogenous FEA2 gene, wherein the endogenous FEA2 gene: (a) comprises a nucleotide sequence having at least 90% sequence identity to the sequence of SEQ ID NO: 72 or SEQ ID NO:73; (b) encodes an amino acid sequence having at least 90% sequence identity to the sequence of SEQ ID NO:74; (c) comprises a region having at least 90% sequence identity to the nucleotide sequence of any one of SEQ ID NOs: 75-77; and/or (d) encodes a region of a polypeptide comprising a region having at least 90% sequence identity to the amino acid sequence of any one of SEQ ID NOs: 78-80, optionally wherein the sequence identity of (a), (b), (c), and/or (d) may be at least 95%, optionally the sequence identity may be 100%, and the cleavage domain cleaves a target strand in the FEA2 gene. In some embodiments, the cleavage domain cleaves a target strand in the FEA2 gene resulting in a mutation in an endogenous FEA2 gene comprising a sequence having at least 90% identity to any one of SEQ ID NOs: 82, 84, 86, 88, 90, 92, 94, 96 or 98, optionally wherein the sequence identity may be at least 95%, optionally the sequence identity may be 100%, and/or encoding a mutated FEA2 polypeptide having at least 90% sequence identity to any one of SEQ ID NOs: 83, 85, 87, 89, 91, 93, 95, 97, or 99, optionally wherein the sequence identity may be at least 95%, optionally the sequence identity may be 100%.

In some embodiments, expression cassettes are provided that comprise (a) a polynucleotide encoding CRISPR-Cas effector protein comprising a cleavage domain and (b) a guide nucleic acid that binds to a target site in an endogenous FEA2 gene, wherein the guide nucleic acid comprises a spacer sequence that is complementary to and binds to (i) a portion of a nucleic acid encoding an amino acid sequence having at least 90% sequence identity the amino acid sequence of SEQ ID NO:74; (ii) a portion of a sequence having at least 90% sequence identity to the nucleotide sequence of SEQ ID NO:72 or SEQ ID NO:73; (iii) a portion of a sequence having at least 90% sequence identity to any one of the nucleotide sequences of any one of SEQ ID NOs: 75-77; and/or (iv) a portion of a nucleic acid encoding a region of a polypeptide having at least 90% sequence identity to the amino acid sequence of any one of SEQ ID NOs: 78-80 optionally wherein the sequence identity of (i), (ii), (iii), and/or (iv) may be at least 95%, optionally the sequence identity may be 100%.

Also provided herein are nucleic acids encoding a mutated FEA2 gene that when present in a corn plant or plant part results in the corn plant comprising a phenotype of increased kernel row number (e.g., a phenotype of producing ears having increased kernel row number), and optionally increased yield, as compared to a control corn plant not comprising the FEA2 mutation, optionally wherein the ears having increased kernel row number do not have a substantially decreased length (e.g., a decrease in length of less than 30% as compared to an ear of a corn plant not comprising the same FEA2 mutation). In some embodiments, a mutated FEA2 gene may comprise a sequence having at least 90% sequence identity to any one of SEQ ID NOs: 82, 84, 86, 88, 90, 92, 94, 96 or 98, optionally wherein the sequence identity may be at least 95%, optionally the sequence identity may be 100%, or encodes a polypeptide having at least 90% sequence identity to any one of SEQ ID NOs: 83, 85, 87, 89, 91, 93, 95, 97, or 99, optionally wherein the sequence identity may be at least 95%, optionally the sequence identity may be 100%.

Nucleic acid constructs of the invention (e.g., a construct comprising a sequence specific nucleic acid binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids (e.g., endogenous FEA2 genes) and/or their expression.

Any corn plant comprising an endogenous FEA2 gene that is capable of conferring increased kernel row number may be modified (e.g., mutated, e.g., base edited, cleaved, nicked, etc.) as described herein (e.g., using the polypeptides, polynucleotides, RNPs, nucleic acid constructs, expression cassettes, and/or vectors of the invention) to increase kernel row number in the corn plant. A corn plant exhibiting increased kernel row number may have an increase in kernel row number of about 5% to about 50% (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% or any range or value therein; e.g., about 5% to about 10%, about 5% to about 15%, about 5% to about 20%, about 10% to about 50%, about 20% to about 50%, about 30% to about 50%, and any range or value therein) as compared to a corn plant or part thereof that does not comprise the mutated endogenous FEA2 gene. In some embodiments, corn plants exhibiting increased kernel row number as described herein (e.g., a plant that produces ears having increased kernel row number) produce ears that are also not substantially decreased in length. As used herein, an ear of a corn plant comprising a mutation as described herein that is "not substantially decreased in length" has a length that is reduced by less than 30% (e.g., reduced by 0% or reduced by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30% or any range or value therein) as compared to a corn plant that does not comprise the same FEA2 mutation.

In some embodiments, a corn plant or plant part thereof is provided comprising at least one mutation in at least one endogenous FASCIATED EAR2 (FEA2) gene having the gene identification number (gene ID) of Zm00001d051012, wherein the mutated endogenous FEA2 gene comprises a nucleic acid sequence having at least 90% sequence identity to any one of SEQ ID NOs: 82, 84, 86, 88, 90, 92, 94, 96 or 98, optionally wherein the sequence identity may be at least 95%, optionally the sequence identity may be 100%, and/or encodes a mutated FEA2 polypeptide having at least 90% sequence identity to any one of SEQ ID NOs: 83, 85, 87, 89, 91, 93, 95, 97, or 99, optionally wherein the sequence identity may be at least 95%, optionally the sequence identity may be 100%, optionally wherein the at least one mutation is a non-natural mutation.

The term "plant part," as used herein, includes but is not limited to reproductive tissues (e.g., petals, sepals, stamens, pistils, receptacles, anthers, pollen, flowers, fruits, flower bud, ovules, seeds, and embryos); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

An editing system useful with this invention can be any site-specific (sequence-specific) genome editing system now known or later developed, which system can introduce mutations in target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system can comprise one or more sequence-specific nucleic acid binding domains (DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing an FEA2 gene may comprise contacting a target nucleic acid (e.g., a nucleic acid encoding an FEA2) with a base-editing fusion protein (e.g., a sequence specific nucleic acid binding protein, a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid. In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific nucleic acid binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing an FEA2 gene may comprise contacting a target nucleic acid (e.g., a nucleic acid encoding an FEA2) with a sequence-specific nucleic acid binding fusion protein (e.g., a sequence-specific DNA binding protein (e.g., a CRISPR-Cas effector protein or domain) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific nucleic acid binding fusion protein to the target nucleic acid and the sequence-specific nucleic acid binding fusion protein is capable of recruiting the deaminase fusion protein to the target nucleic acid via the peptide tag-affinity polypeptide interaction, thereby editing a locus within the target nucleic acid. In some embodiments, the sequence-specific nucleic acid binding fusion protein may be fused to the affinity polypeptide that binds the peptide tag and the deaminase may be fuse to the peptide tag, thereby recruiting the deaminase to the sequence-specific nucleic acid binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific nucleic acid binding fusion proteins, deaminase fusion proteins and guides may be provided as ribonucleoproteins (RNPs).

In some embodiments, methods such as prime editing may be used to generate a mutation in an endogenous FEA2 gene. In prime editing, RNA-dependent DNA polymerase (reverse transcriptase, RT) and reverse transcriptase templates (RT template) are used in combination with sequence specific nucleic acid binding domains that confer the ability to recognize and bind the target in a sequence-specific manner, and which can also cause a nick of the PAM-containing strand within the target. The nucleic acid binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantageous of the various methods of recruiting proteins for use in the editing to the target site, such methods including both non-covalent and covalent interactions between the proteins and nucleic acids used in the selected process of genome editing.

As used herein, a "CRISPR-Cas effector protein" is a protein or polypeptide or domain thereof that cleaves or cuts a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid.

In some embodiments, a sequence-specific nucleic acid binding domain (e.g., a sequence-specific DNA binding domain) may be a CRISPR-Cas effector protein. In some embodiments, a CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, CaslB, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Cscl, Csc2, Csa5, Csn2, Csm2, Csm3, Csm4, Csm5, Csm6, Cmr1, Cmr3, Cmr4, Cmr5, Cmr6, Csbl, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain, e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g., Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes, S. thermophilus*), *Lactobacillus* spp., *Bifidobacterium* spp., Kandleria spp., *Leuconostoc* spp., Oenococcus spp., *Pediococcus* spp., Weissella spp., and/or Olsenella spp. Example Cas9 sequences include, but are not limited to, the amino acid sequences of SEQ ID NO: 59 and SEQ ID NO:60 or the nucleotide sequences of SEQ ID NOs: 61-71.

In some embodiments, the CRISPR-Cas effector protein may be a Cas9 polypeptide derived from *Streptococcus pyogenes* and recognizes the PAM sequence motif NGG, NAG, NGA (*Mali* et al, Science 2013; 339 (6121): 823-826). In some embodiments, the CRISPR-Cas effector protein may be a Cas9 polypeptide derived from *Streptococcus* thermophiles and recognizes the PAM sequence motif NGGNG and/or NNAGAAW (W=A or T) (See, e.g., Horvath et al, Science, 2010; 327 (5962): 167-170, and Deveau et al, J Bacteriol 2008; 190 (4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, J BACTERIOL 2008; 190 (4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S. aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas effector protein may be a Cas13a protein derived from *Leptotrichia shahii*, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease see, e.g., SEQ ID NOs: 1-20). Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas 12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. Nat. Biotechnol. 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally occurring cytosine deaminase, including but not limited to a primate (e.g., a human, monkey, chimpanzee, gorilla), a dog, a cow, a rat or a mouse. Thus, in some embodiments, a cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:27, SEQ ID NO: 28 or SEQ ID NO:29). In some embodiments, the cytosine deaminase may be an APOBEC1 deaminase having the amino acid sequence of SEQ ID NO:23. In some embodiments, the cytosine deaminase may be an APOBEC3A deaminase having the amino acid sequence of SEQ ID NO:24. In some embodiments, the cytosine deaminase may be an CDA1 deaminase, optionally a CDA1 having the amino acid sequence of SEQ ID NO:25. In some embodiments, the cytosine deaminase may be a FERNY deaminase, optionally a FERNY having the amino acid sequence of SEQ ID NO:26. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of any one of SEQ ID NO:23, SEQ ID NO:24, SEQ ID NO:25 or SEQ ID NO:26 (e.g., at least 80%, at least 85%, at least 90%, at least 92%, at least 95%, at least 96%, at least 97%, at least 98%, at least 99%, or at least 99.5% identical to the amino acid sequence of any one of SEQ ID NO:23, SEQ ID NO:24, SEQ ID NO:25, SEQ ID NO:26, SEQ ID NO:27, SEQ ID NO: 28 or SEQ ID NO:29). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode a uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:41 or a polypeptide having about 70% to about 99.5% sequence identity to the amino acid sequence of SEQ ID NO:41 (e.g., at least 80%, at least 85%, at least 90%, at least 92%, at least 95%, at least 96%, at least 97%, at least 98%, at least 99%, or at least 99.5% identical to the amino acid sequence of SEQ ID NO:41). For example, in some embodiments, a UGI domain may comprise a fragment of the amino acid sequence of SEQ ID NO:41 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:41. In some embodiments, a UGI domain may be a variant of a known UGI (e.g., SEQ ID NO:41) having about 70% to about 99.5% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% sequence identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:30. In some embodiments, a mutated/evolved *E. coli* TadA* comprises the amino acid sequence of SEQ ID NOs: 31-40 (e.g., SEQ ID NOs: 31, 32, 33, 34, 35, 36, 37, 38, 39 or 40). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific nucleic acid binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt function; and/or generation of point mutations in genomic DNA to disrupt splice junctions.

The nucleic acid constructs of the invention encoding a base editor comprising a sequence-specific nucleic acid binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt function; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Casl, CaslB, Cas2, Cas3, Cas3', Cas3", Cas4, Cas5, Cas6, Cas7, Cas8, Cas9 (also known as Csnl and Csx12), Cas10, Csy1, Csy2, Csy3, Csel, Cse2, Cscl, Csc2, Csa5, Csn2, Csm2, Csm3, Csm4, Csm5, Csm6, Cmr1, Cmr3, Cmr4, Cmr5, Cmr6, Csbl, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Casl, CaslB, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Cscl, Csc2, Csa5, Csn2, Csm2, Csm3, Csm4, Csm5, Csm6, Cmr1, Cmr3, Cmr4, Cmr5, Cmr6, Csbl, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild type CRISPR-Cas locus may be determined through established algorithms, such as using the CRISPRfinder offered through CRISPRdb (see, Grissa et al. *Nucleic Acids Res.* 35 (Web Server issue): W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is substantially complementary to a target nucleic acid (e.g., target DNA) (e.g., protospacer) (e.g., substantially complementary to consecutive nucleotides of a portion/region of a nucleotide sequence (a) having at least 90% sequence identity to any one of SEQ ID NOs: 72, 73 and/or 75-77, or (b) encoding an amino acid sequence having at least 90% sequence identity to SEQ ID NO:74 or SEQ ID NO:78-80, optionally wherein the sequence identity of (a) or (b) may be at least 95%, optionally the sequence identity may be 100%). In some embodiments, a spacer sequence may include, but is not limited to, the nucleotide sequences of SEQ ID NOs: 81. A spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can be 70% complementary to a target nucleic acid. In other embodiments, the spacer nucleotide sequence can be 80% complementary to a target nucleic acid. In still other embodiments, the spacer nucleotide sequence can be 85%, 90%, 95%, 96%, 97%, 98%, 99% or 99.5% complementary, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity (e.g., at least 70% complementarity) over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (see, for example, a spacer sequence of a Type V CRISPR-Cas system), or the 3' region of a spacer sequence of a guide nucleic acid may be identical to a target DNA, while the 5' region of the spacer may be substantially complementary to the target DNA (see, for example, a spacer sequence of a Type II CRISPR-Cas system), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

```
    5'-NNNNNNNNNNNNNNNNNNNN-3' RNA Spacer          (SEQ ID NO: 42)
       ||||||||||||||||||||
3'AAANNNNNNNNNNNNNNNNNNNNN-5' Target strand        (SEQ ID NO: 43)
  ||||
5'TTTNNNNNNNNNNNNNNNNNNNNN-3' Non-target strand    (SEQ ID NO: 44)
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types, and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be S'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific nucleic acid binding domains, CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a octapeptide sold under the tradename FLAG®, a strep tag or strep tag II, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26 (5): 910-924 (2017)); Gilbreth (*Curr Opin Struc Biol* 22 (4): 413-420 (2013)), U.S. Pat. No. 9,982,053, each of which are incorporated by reference in their entireties for the teachings relevant to affibodies, anticalins, monobodies and/or DARPins. Example peptide tag sequences and their affinity polypeptides include, but are not limited to, the amino acid sequences of SEQ ID NOs: 45-47.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases). Example RNA recruiting motifs and their affinity polypeptides include, but are not limited to, the sequences of SEQ ID NOs: 48-58.

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat-spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide *Pumilio*/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide *Pumilio*/fem-3 mRNA binding factor (PUF).

In some embodiments, the components for recruiting polypeptides and nucleic acids may those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together, e.g. dihyrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

Further provided herein are cells comprising one or more polynucleotides, guide nucleic acids, nucleic acid constructs, expression cassettes or vectors of the invention.

The invention will now be described with reference to the following examples. It should be appreciated that these examples are not intended to limit the scope of the claims to the invention but are rather intended to be exemplary of certain embodiments. Any variations in the exemplified methods that occur to the skilled artisan are intended to fall within the scope of the invention.

EXAMPLES

Example 1. Design of the Editing Constructs for Fea2 Editing

The genomic sequence of the FEA2 gene was identified in a proprietary maize line. From this reference sequence, spacer sequences (e.g., SEQ ID NO:81) were designed for use in editing constructs. The editing constructs contained a CRISPR-Cas effector and a spacer sequence designed to target the 10th LRR repeat of the FEA2 protein encoded by the FEA2 gene (e.g., SEQ ID NO:72). Spacers were deployed with either a Cas-effector cutting enzyme or a Cas-effector base editing complex.

Example 2. Transformation and Selection of Edited E0 Plants

A vector encoding the spacer (SEQ ID NO:81) as well as the chosen CRISPR-Cas effector were introduced into dried excised maize embryos using *Agrobacterium*. Transformed tissue was maintained in vitro with antibiotic selection to regenerate positive transformants. Healthy non-chimeric plants (E0) were selected and planted in growth trays. Tissue was collected from regenerating plants (E0 generation) for DNA extraction and subsequent molecular screening was employed to identify edits in the FEA2. Plants identified to be (1) healthy, non-chimeric and fertile, with (2) low transgene copy and (3) an edit in the $10^{th}$ LRR repeat of the FEA2 polypeptide encoded by the FEA2 gene were advanced to the next generation. E0 plants that satisfied all the above criteria were selfed to produce the E1 generation. Selected Els were selfed to generate the E2 generation. We identified several families with deletions and substitutions in and around the $10^{th}$ LRR.

Example 3. Phenotypic Assessment of Trait Activity

Seeds for E1 and E2 material were sown in flats and later transferred to pots after seedlings were established. All materials were cultivated under standard greenhouse conditions and grown to reproductive maturity. Following standard practices, emerging ears were covered with small paper bags prior to the emergence of silk and tassels were covered during anthesis for the capture of pollen on a plant-by-plant basis. In some cases, anthesis and silking were not synchronized, and ears were not pollinated. We designate these as 'unpollinated' ears and evaluated them separately for kernel row number determination (as described below) once all ears were removed from the corn plants after dry-down.

After ear harvest and dry-down, kernel row number was manually counted for all ears. Data represent the average of three row counts per ear taken from the mid-section of the ear where row lineages were most defined. In order to prevent double counting of rows, a marker (e.g., paper clip) was inserted in between the rows where the counts initiated and to designate where row counting should cease.

All ears were photo-documented with a Canon digital camera and EOS application. Images were subsequently imported into ImageJ and all ears were measured using the line trace function. Ear length was determined in centimeters by a setting scale in the image analysis program to output distance in centimeters after ears were traced with lines along the length of ear from its tip to the base of ear. Un-edited germplasm, and lines transformed with a Gus plasmid were used as wild type controls for phenotyping.

Example 4. Edited Alleles FEA2

Edited alleles of the FEA2 gene Zm00001d051012 were generated as described in Example 1 and Example 2 and are further described in Table 1.

TABLE 1

Edited alleles

| Allele | Edit description | notes |
|---|---|---|
| Allele A (SEQ ID NO: 82) | 24 bp deletion (GGTGGACTTGTCAGGAA ATGAGAT; SEQ ID NO: 100) starting at position 2064 of SEQ ID NO: 72 | In frame deletion of the amino acids "VDLSGNEI" (SEQ ID NO: 101) at position 328-335 of SEQ ID NO: 74 giving rise to the amino acid sequence of SEQ ID NO: 83 |
| Allele B (SEQ ID NO: 84) | 1 bp insertion at position 2073 of SEQ ID NO: 72 | Out of frame mutation leading to an early stop codon (SEQ ID NO: 85) |
| Allele C (SEQ ID NO: 86) | 8 bp deletion (TCAGGAAA) starting at position 2074 of SEQ ID NO: 72 | Out of frame mutation leading to an early stop codon (SEQ ID NO: 87) |
| Allele D (SEQ ID NO: 88) | 12 bp deletion (TTGTCAGGAAAT; SEQ ID NO: 102) starting at position 2071 of SEQ ID NO: 72 | In frame deletion of amino acids "LSGN" (SEQ ID NO: 103) at position 330-333 of SEQ ID NO: 74 giving rise to the amino acid sequence SEQ ID NO: 89 |

TABLE 1-continued

| Edited alleles | | |
|---|---|---|
| Allele | Edit description | notes |
| Allele E (SEQ ID NO: 90) | 39 bp deletion (TCTTTGGAGGTGGTGGAC TTGTCAGGAAATGAGATC TCC; SEQ ID NO: 104) starting at position 2053 of SEQ ID NO: 72 | In frame deletion of amino acids "SLEVVDLSGNEIS" (SEQ ID NO: 105) at position 324-336 of SEQ ID NO: 74 giving rise to the amino acid sequence of SEQ ID NO: 91 |
| Allele F (SEQ ID NO: 92) | 2 bp deletion (CA) starting at position 2075 of SEQ ID NO: 72 | Out of frame mutation leading to an early stop codon (SEQ ID NO: 93) |
| Allele G (SEQ ID NO: 94) | 24 bp deletion (GGTGGTGGACTTGTCAGG AAATGA; SEQ ID NO: 106) starting at position 2061 of SEQ ID NO: 72 | In frame deletion of amino acids "VVDLSGNE" (SEQ ID NO: 107) at position 327-334 of SEQ ID NO: 74 giving rise to the amino acid sequence SEQ ID NO: 95 |
| Allele H (SEQ ID NO: 96) | 9 bp deletion (TGTCAGGAA) starting at position 2072 of SEQ ID NO: 72 | In frame deletion of the amino acids "LSGN" (SEQ ID NO: 103) at position 330-333 of SEQ ID NO: 74 and replace with the amino acid "Y" giving rise to the amino acid sequence SEQ ID NO: 97 CE116316_LOCUS4_A_aa 2072:9D |
| Allele I (SEQ ID NO: 98) | 4 bp deletion (TCAG) starting at position 2074 of SEQ ID NO: 72 | Out of frame mutation leading to an early stop codon (SEQ ID NO: 99) |

Example 5. Phenotype Analysis of Edited Alleles

Plants containing the edited alleles of FEA2 which are described in Example 4 were evaluated for phenotypic changes in ears as described in Example 3. The observations are summarized in Table 2 and demonstrate that the edited alleles of FEA2 have altered the formation of ears and number of kernels and may increase overall plant yield.

The entry "in-frame compound het" represents a mixed group of plants that contained a combination of alleles D, E, G or H without any wild type sequence present.

TABLE 2

| Kernel row number analysis of edited alleles | | | | | | |
|---|---|---|---|---|---|---|
| Genotype | Min | Median | Max | Mean | Standard deviation of mean | number |
| Wild type control | 14 | 16 | 19 | 15.98039 | 1.208142 | 51 |
| Homozygous Allele A | 16 | 19 | 23 | 19.44444 | 2.603417 | 9 |
| Homozygous Allele B | 18 | 23.5 | 26 | 22.50000 | 3.271085 | 6 |
| In-Frame Compound Het | 14 | 21 | 28 | 21.16667 | 3.658559 | 30 |
| Homozygous Allele F | 17 | 21 | 25 | 21.44444 | 2.403701 | 9 |

In some jurisdictions, products obtained exclusively by essentially biological processes are excluded from patent protection. Accordingly, the claimed plants, plant parts and cells and their progeny can be defined as directed only to those plants, plant parts and cells and their progeny which are obtained by technical intervention (regardless of any further propagation through crossing and selection). An embodiment of the invention is directed at plants, or plant parts or progeny produced or obtainable using gene editing technology by introducing through stable or transient transformation an RNA-specific CRISPR/Cas system directed against or targeting a nucleotide sequence encoding the FEA2 protein, or one or more polynucleotide sequence(s) encoding said RNA-specific CRISPR/Cas system into the plant or the plant part. Alternatively, the subject matter excluded from patentability may be disclaimed. An embodiment of the invention is directed at plants, part of plants or progeny thereof comprising the alterations of the FEA2 gene as elsewhere herein described, provided that the plants, parts or plants or progeny are not obtained exclusively through essentially biological processes, wherein essentially biological processes are processes for the production of plants or animals if they consist entirely of natural phenomena such as crossing or selection.

The foregoing is illustrative of the present invention and is not to be construed as limiting thereof. The invention is defined by the following claims, with equivalents of the claims to be included therein.

SEQUENCE LISTING

```
Sequence total quantity: 107
SEQ ID NO: 1           moltype = AA  length = 1228
FEATURE                Location/Qualifiers
```

-continued

```
source                1..1228
                      mol_type = protein
                      note = Lachnospiraceae sp.
                      organism = unidentified
SEQUENCE: 1
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                   1228

SEQ ID NO: 2          moltype = AA  length = 1307
FEATURE               Location/Qualifiers
source                1..1307
                      mol_type = protein
                      organism = Acidaminococcus sp.
SEQUENCE: 2
MTQFEGFTNL YQVSKTLRFE LIPQGKTLKH IQEQGFIEED KARNDHYKEL KPIIDRIYKT  60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DKMYYDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN              1307

SEQ ID NO: 3          moltype = AA  length = 1241
FEATURE               Location/Qualifiers
source                1..1241
                      mol_type = protein
                      organism = Butyrivibrio proteoclasticus
SEQUENCE: 3
MLLYENYTKR NQITKSLRLE LRPQGKTLRN IKELNLLEQD KAIYALLERL KPVIDEGIKD  60
IARDTLKNCE LSFEKLYEHF LSGDKKAYAK ESERLKKEIV KTLIKNLPEG IGKISEINSA  120
KYLNGVLYDF IDKTHKDSEE KQNILSDILE TKGYLALFSK FLTSRITTLE QSMPKRVIEN  180
FEIYAANIPK MQDALERGAV SFAIEYESIC SVDYYNQILS QEDIDSYNRL ISGIMDEDGA  240
KEKGINQTIS EKNIKIKSEH LEEKPFRILK QLHKQILEER EKAFTIDHID SDEEVVQVTK  300
EAFEQTKEQW ENIKKINGFY AKDPGDITLF IVVGPNQTHV LSQLIYGEHD RIRLLLEEYE  360
KNTLEVLPRR TKSEDARYDK FVNAVPKKVA KESHTFDGLQ KMTGDDRLFI LYRDELARNY  420
MRIKEAYGTF ERDILKSRRG IKGNRDVQES LVSFYDELTK FRSALRIINS GNDEKADPIF  480
YNTFDGIFEK ANRTYKAENL CRNYVTKSPA DDARIMASCL GTPARLRTHW WNGEENFAIN  540
DVAMIRRGDE YYYFVLTPDV KPVDLKTKDE TDAQIFVQRK GAKSFLGLPK ALFKCILEPY  600
FESPEHKNDK NCVIEEYVSK PLTIDRRAYD IFKNGTFKKT NIGIDGLTEE KFKDDCRYLI  660
DVYKEFIAVY TRYSCFNMSG LKRADEYNDI GEFFSDVDTR LCTMEWIPVS FERINDMVDK  720
KEGLLFLVRS MFLYNRPRKP YERTFIQLFS DSNMEHTSML LNSRAMIQYR AASLPRRVTH  780
KKGSILVALR DSNGEHIPMH IREAIYKMKN NFDISSEDFI MAKAYLAEHD VAIKKANEDI  840
IRNRRYTEDK FFLSLSYTKN ADISARTLDY INDKVEEDTQ DSRMAVIVTR NLKDLTYVAV  900
VDEKNNVLEE KSLNEIDGVN YRELLKERTK IKYHDKTRLW QYDVSSKGLK EAYVELAVTQ  960
ISKLATKYNA VVVVESMSST FKDKFSFLDE QIFKAFEARL CARMSDLSFN TIKEGEAGSI  1020
```

-continued

```
SNPIQVSNNN GNSYQDGVIY FLNNAYTRTL CPDTGFVDVF DKTRLITMQS KRQFFAKMKD  1080
IRIDDGEMLF TFNLEEYPTK RLLDRKEWTV KIAGDGSYFD KDKGEYVYVN DIVREQIIPA  1140
LLEDKAVFDG NMAEKFLDKT AISGKSVELI YKWFANALYG IITKKDGEKI YRSPITGTEI  1200
DVSKNTTYNF GKKFMFKQEY RGDGDFLDAF LNYMQAQDIA V                      1241

SEQ ID NO: 4            moltype = AA  length = 1238
FEATURE                 Location/Qualifiers
source                  1..1238
                        mol_type = protein
                        organism = Methanoplasma termitum
SEQUENCE: 4
MNNYDEFTKL YPIQKTIRFE LKPQGRTMEH LETFNFFEED RDRAEKYKIL KEAIDEYHKK  60
FIDEHLTNMS LDWNSLKQIS EKYYKSREEK DKKVFLSEQK RMRQEIVSEF KKDDRFKDLF  120
SKKLFSELLK EEIYKKGNHQ EIDALKSFDK FSGYFIGLHE NRKNMYSDGD EITAISNRIV  180
NENFPKFLDN LQKYQEARKK YPEWIIKAES ALVAHNIKMD IVFSLEYFNK VLNQEGIQRY  240
NLALGGYVTK SGEKMMGLND ALNLAHQSEK SSKGRIHMTP LFKQILSEKE SFSYIPDVFT  300
EDSQLLPSIG GFFAQIENDK DGNIFDRALE LISSYAEYDT ERIYIRQADI NRVSNVIFGE  360
WGTLGGLMRE YKADSINDIN LERTCKKVDK WLDSKEFALS DVLEAIDRTG NNDAFNEYIS  420
KMRTAREKID AARKEMKFIS EKISGDEESI HIIKTLLDSV QQFLHFFNLF KARQDIPLDG  480
AFYAEFDEVH SKLFAIVPLY NKVRNYLTKN NLNTKKIKLN FKNPTLANGW DQNKVYDYAS  540
LIFLRDGNYY LGIINPKRKK NIKFEQGSGN GPFYRKMVYK QIPGPNKNLR PVFLTSTKGK  600
KEYKPSKEII EGYEADKHIR GDKFDLDFCH KLIDFFKESI EKHKDWSKFN FYFSPTESYG  660
DISEFYLDVE KQGYRMHFEN ISAETIDEYV EKGDLFLFQI YNKDFVKAAT GKKDMHTIYW  720
NAAFSPENLQ DVVVKLNGEA ELFYRDKSDI KEIVHREGEI LVNRTYNGRT PVPDKIHKKL  780
TDYHNGRTKD LGEAKEYLDK VRYFKAHYDI TKDRRYLNDK IYFHVPLTLN FKANGKKNLN  840
KMVIEKFLSD EKAHIIGIDR GERNLLYYSI IDRSGKIIDQ QSLNVIDGFD YREKLNQREI  900
EMKDARQSWN AIGKIKDLKE GYLSKAVHEI TKMAIQYNAI VVMEELNYGF KRGRFKVEKQ  960
IYQKFENMLI DKMNYLVFKD APDESPGGVL NAYQLTNPLE SFAKLGKQTG ILFYVPAAYT  1020
SKIDPTTGFV NLFNTSSKTN AQERKEFLQK FESISYSAKD GGIFAFAFDY RKFGTSKTDH  1080
KNVWTAYTNG ERMRYIKEKK RNELFDPSKE IKEALTSSGI KYDGGQNILP DILRSNNNGL  1140
IYTMYSSFIA AIQMRVYDGK EDYIISPIKN SKGEFFRTDP KRRELPIDAD ANGAYNIALR  1200
GELTMRAIAE KFDPDSEKMA KLELKHKDWF EFMQTRGD                         1238

SEQ ID NO: 5            moltype = AA  length = 1281
FEATURE                 Location/Qualifiers
source                  1..1281
                        mol_type = protein
                        organism = Eubacterium eligens
SEQUENCE: 5
MNGNRSIVYR EFVGVIPVAK TLRNELRPVG HTQEHIIQNG LIQEDELRQE KSTELKNIMD  60
DYYREYIDKS LSGVTDLDFT LLFELMNLVQ SSPSKDNKKA LEKEQSKMRE QICTHLQSDS  120
NYKNIFNAKL LKEILPDFIK NYNQYDVKDK AGKLETLALF NGFSTYFTDF FEKRKNVFTK  180
EAVSTSIAYR IVHENSLIFL ANMTSYKKIS EKALDEIEVI EKNNQDKMGD WELNQIFNPD  240
FYNMVLIQSG IDFYNEICGV VNAHMNLYCQ QTKNNYNLFK MRKLHKQILA YTSTSFEVPK  300
MFEDDMSVYN AVNAFIDETE KGNIIGKLKD IVNKYDELDE KRIYISKDFY ETLSCFMSGN  360
WNLITGCVEN FYDENIHAKG KSKEEKVKKA VKEDKYKSIN DVNDLVEKYI DEKERNEFKN  420
SNAKQYIREI SNIITDTETA HLEYDDHISL IESEEKADEM KKRLDMYMNM YHWAKAFIVD  480
EVLDRDEMFY SDIDDIYNIL ENIVPLYNRV RNYVTQKPYN SKKIKLNFQS PTLANGWSQS  540
KEFDNNAIIL IRDNKYYLAI FNAKNKPDKK IIQGNSDKKN DNDYKKMVYN LLPGANKMLP  600
KVFLSKKGIE TFKPSDYIIS GYNAHKHIKT SENFDISFCR DLIDYFKNSI EKHAEWRKYE  660
FKFSATDSYS DISEFYREVE MQGYRIDWTY ISEADINKLD EEGKIYLFQI YNKDFAENST  720
GKENLHTMYF KNIFSEENLD KIIKLNGQAE LFYRRASVKN PVKHKKDSVL VNKTYKNQLD  780
NGDVVRIPIP DDIYNEIYKM YNGYIKESDL SEAAKEYLDK VEVRTAQKDI VKDYRYTVDK  840
YFIHTPITIN YKVTARNNVN DMVVKYIAQN DDIHVIGIDR GERNLIYISV IDSHGNIVKQ  900
KSYNILNNYD YKKKLVEKEK TREYARKNWK SIGNIKELKE GYISGVVHEI AMLIVEYNAI  960
IAMEDLNYGF KRGRFKVERQ VYQKFESMLI NKLNYFASKE KSVDEPGGLL KGYQLTYVPD  1020
NIKNLGKQCG VIFYVPAAFT SKIDPSTGFI SAFNFKSIST NASRKQFFMQ FDEIRYCAEK  1080
DMFSFGFDYN NFDTYNITMG KTQWTVYTNG ERLQSEFNNA RRTGKTKSIN LTETIKLLLE  1140
DNEINYADGH DIRIDMEKMD EDKKSEFFAQ LLSLYKLTVQ MRNSYTEAEE QENGISYDKI  1200
ISPVINDEGE FFDSDNYKES DDKECKMPKD ADANGAYCIA LKGLYEVLKI KSEWTEDGFD  1260
RNCLKLPHAE WLDFIQNKRY E                                           1281

SEQ ID NO: 6            moltype = AA  length = 1300
FEATURE                 Location/Qualifiers
source                  1..1300
                        mol_type = protein
                        organism = Francisella novicida
SEQUENCE: 6
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKNVY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
```

-continued

```
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                        1300

SEQ ID NO: 7            moltype = AA  length = 1206
FEATURE                 Location/Qualifiers
REGION                  1..1206
                        note = Lachnospiraceae sp.
source                  1..1206
                        mol_type = protein
                        organism = unidentified
SEQUENCE: 7
MYYESLTKQY PVSKTIRNEL IPIGKTLDNI RQNNILESDV KRKQNYEHVK GILDEYHKQL  60
INEALDNCTL PSLKIAAEIY LKNQKEVSDR EDFNKTQDLL RKEVVEKLKA HENFTKIGKK  120
DILDLLEKLP SISEDDYNAL ESFRNFYTYF TSYNKVRENL YSDKEKSSTV AYRLINENFP  180
KFLDNVKSYR FVKTAGILAD GLGEEEQDSL FIVETFNKTL TQDGIDTYNS QVGKINSSIN  240
LYNQKNQKAN GFRKIPKMKM LYKQILSDRE ESFIDEFQSD EVLIDNVESY GSVLIESLKS  300
SKVSAFFDAL RESKGKNVYV KNDLAKTAMS VIVFENWRTF DDLLNQEYDL ANENKKKDDK  360
YFEKRQKELK KNKSYSLEHL CNLSEDSCNL IENYIHQISD DIENIIINNE TFLRIVINEH  420
DRSRKLAKNR KAVKAIKDFL DSIKVLEREL KLINSSGQEL EKDLIVYSAH EELLVELKQV  480
DSLYNMTRNY LTKKPFSTEK VKLNFNRSTL LNGWDRNKET DNLGVLLLKD GKYYLGIMNT  540
SANKAFVNPP VAKTEKVFKK VDYKLLPVPN QMLPKVFFAK SNIDFYNPSS EIYSNYKKGT  600
HKKGNMFSLE DCHNLIDFFK ESISKHEDWS KFGFKFDTQA SYNDISEFYR EVEKQGYKLT  660
YTDIDETYIN DLIERNELYL FQIYNKDFSM YSKGKLNLHT LYFMMLFDQR NIDDVVYKLN  720
GEAEVFYRPA SISEDELIIH KAGEEIKNKN PNRARTKETS TFSYDIVKDK RYSKDKFTLH  780
IPITMNFGVD EVKRFNDAVN SAIRIDENVN VIGIDRGERN LLYVVVIDSK GNILEQISLN  840
SIINKEYDIE TDYHALLDER EGGRDKARKD WNTVENIRDL KAGLYLQVVN VVAKLVLKYN  900
AIICLEDLNF GFKRGRQKVE KQVYQKFEKM LIDKLNYLVI DKSREQTSPK ELGGALNALQ  960
LTSKFKSFKE LGKQSGVIYY VPAYLTSKID PTTGFANLFY MKCENVEKSK RFFDGFDFIR  1020
FNALENVFEF GFDYRSFTQR ACGINSKWTV CTNGERIIKY RNPDKNNMFD EKVVVVTDEM  1080
KNLFEQYKIP YEDGRNVKDM IISNEEAEFY RRLYRLLQQT LQMRNSTSDG TRDYIISPVK  1140
NKREAYFNSE LSDGSVPKDA DANGAYNIAR KGLWVLEQIR QKSEGEKINL AMTNAEWLEY  1200
AQTHLL                                                             1206

SEQ ID NO: 8            moltype = AA  length = 1233
FEATURE                 Location/Qualifiers
source                  1..1233
                        mol_type = protein
                        note = Lachnospiraceae sp.
                        organism = unidentified
SEQUENCE: 8
MDYGNGQFER RAPLTKTITL RLKPIGETRE TIREQKLLEQ DAAFRKLVET VTPIVDDCIR  60
KIADNALCHF GTEYDFSCLG NAISKNDSKA IKKETEKVEK LLAKVLTENL PDGLRKVNDI  120
NSAAFIQDTL TSFVQDDADK RVLIQELKGK TVLMQRFLTT RITALTVWLP DRVFENFNIF  180
IENAEKMRIL LDSPLNEKIM KFDPDAEQYA SLEFYGQCLS QKDIDSYNLI ISGIYADDEV  240
KNPGINEIVK EYNQQIRGDK DESPLPKLKK LHKQILMPVE KAFFVRVLSN DSDARSILEK  300
ILKDTEMLPS KIIEAMKEAD AGDIAVYGSR LHELSHVIYG DHGKLSQIIY DKESKRISEL  360
METLSPKERK ESKKRLEGLE EHIRKSTYTF DELNRYAEKN VMAAYIAAVE ESCAEIMRKE  420
KDLRTLLSKE DVKIRGNRHN TLIVKNYFNA WTVFRNLIRI LRRKSEAEID SDFYDVLDDS  480
VEVLSLTYKG ENLCRSYITK KIGSDLKPEI ATYGSALRPN SRWWSPGEKF NVKFHTIVRR  540
DGRLYYFILP KGAKPVELED MDGDIECLQM RKIPNPTIFL PKLVFKDPEA FFRDNPEADE  600
FVFLSGMKAP VTITRETYEA YRYKLYTVGK LRDGEVSEEE YKRALLQVLT AYKEFLENRM  660
IYADLNFGFK DLEEYKDSSE FIKQVETHNT FMCWAKVSSS QLDDLVKSGN GLLFEIWSER  720
LESYYKYGNE KVLRGYEGVL LSILKDENLV SMRTLLNSRP MLVYRPKESS KPMVVHRDGS  780
RVVDRFDKDG KYIPPEVHDE LYRFFNNLLI KEKLGEKARK ILDNKKVKVK VLESERVKWS  840
KFYDEQFAVT FSVKKNADCL DTTKDLNAEV MEQYSESNRL ILIRNTTDIL YYLVLDKNGK  900
VLKQRSLNII NDGARDVDWK ERFRQVTKDR NEGYNEWDYS RTSNDLKEVY LNYALKEIAE  960
AVIEYNAILI IEKMSNAFKD KYSFLDDVTF KGFETKKLAK LSDLHFRGIK DGEPCSFTNP  1020
LQLCQNDSNK ILQDGVIFMV PNSMTRSLDP DTGFIFAIND HNIRTKKAKL NFLSKFDQLK  1080
VSSEGCLIMK YSGDSLPTHN TDNRVWNCCC NHPITNYDRE TKKVEFIEEP VEELSRVLEE  1140
NGIETDTELN KLNERENVPG KVVDAIYSLV LNYLRGTVSG VAGQRAVYYS PVTGKKYDIS  1200
FIQAMNLNRK CDYYRIGSKE RGEWTDFVAQ LIN                               1233

SEQ ID NO: 9            moltype = AA  length = 1227
FEATURE                 Location/Qualifiers
source                  1..1227
                        mol_type = protein
                        note = Lachnospiraceae sp.
                        organism = unidentified
SEQUENCE: 9
MSKLEKFTNC YSLSKTLRFK AIPVGKTQEN IDNKRLLVED EKRAEDYKGV KKLLDRYYLS  60
```

-continued

```
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI ANINKCPKNI FKINTEVRVL LKHDDNPYVI GIDRGERNLL  840
YIVVVDGKGN IVEQYSLNEI INNFNGIRIK TDYHSLLDKK EKERFEARQN WTSIENIKEL  900
KAGYISQVVH KICELVEKYD AVIALEDLNS GFKNSRVKVE KQVYQKFEKM LIDKLNYMVD  960
KKSNPCATGG ALKGYQITNK FESFKSMSTQ NGFIFYIPAW LTSKIDPSTG FVNLLKTKYT  1020
SIADKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IASNKEWLEY AQTSVKH                                     1227

SEQ ID NO: 10          moltype = AA  length = 1264
FEATURE                Location/Qualifiers
source                 1..1264
                       mol_type = protein
                       organism = Leptospira inadai
SEQUENCE: 10
MEDYSGFVNI YSIQKTLRFE LKPVGKTLEH IEKKGFLKKD KIRAEDYKAV KKIIDKYHRA  60
YIEEVFDSVL HQKKKKDKTR FSTQFIKEIK EFSELYYKTE KNIPDKERLE ALSEKLRKML  120
VGAFKGEFSE EVAEKYNKNL FSKELIRNEI EKFCETDEER KQVSNFKKSFT TYFTGFHSNR  180
QNIYSDEKKS TAIGYRIIHQ NLPKFLDNLK IIESIQRRFK DFPWSDLKKN LKKIDKNIKL  240
TEYFSIDGFV NVLNQKGIDA YNTILGGKSE ESGEKIQGLN EYINLYRQKN NIDRKNPLNV  300
KILFKQILGD RETKSFIPEA FPDDQSVLNS ITEFAKYLKL DKKKSIIAE LKKFLSSFNR  360
YELDGIYLAN DNSLASISTF LFDDWSFIKK SVSFKYDESV GDPKKKIKSP LKYEKEKEKW  420
LKQKYYTISF LNDAIESYSK SQDEKRVKIR LEAYFAEFKS KDDAKKQFDL LERIEEAYAI  480
VEPLLGAEYP RDRNLKADKK EVGKIKDFLD SIKSLQFFLK PLLSAEIFDE KDLGFYNQLE  540
GYYEEIDISG HLYNKVRNYL TGKIYSKEKF KLNFENSTLL KGWDENREVA NLCVIFREDQ  600
KYYLGVMDKE NNTILSDIPK VKPNELFYEK MVYKLIPTPH MQLPRIIFSS DNLSIYNPSK  660
SILKIREAKS FKEGKNFKLK DCHKFIDFYK ESISKNEDWS RFDFKFSKTS SYENISEFYR  720
EVERQGYNLD FKKVSKFYID SLVEDGKLYL FQIYNKDFSI FSKGKPNLHT IYFRSLFSKE  780
NLKDVCLKLN GEAEMFFRKK SINYDEKKKR EGHHPELFEK LKYPILKDKR YSEDKFQFHL  840
PISLNFKSKE RLNFNLKVNE FLKRNKDINI IGIDRGERNL LYLVMINQKG EILKQTLLDS  900
MQSGKGRPEI NYKEKLQEKE IERDKARKSW GTVENIKELK EGYLSIVIHQ ISKLMVENNA  960
IVVLEDLNIG FKRGRQKVER QVYQKFEKML IDKLNFLVFK ENKPTEPGGV LKAYQLTDEF  1020
QSFEKLSKQT GFLFYVPSWN TSKIDPRTGF IDFLHPAYEN IEKAKQWINK FDSIRFNSKM  1080
DWFEFTADTR KFSENLMLGK NRVWVICTTN VERYFTSKTA NSSIQYNSIQ ITEKLKELFV  1140
DIPFSNGQDL KPEILRKNDA VFFKSLLFYI KTTLSLRQNN GKKGEEEKDF ILSPVVDSKG  1200
RFFNSLEASD DEPKDADANG AYHIALKGLM NLLVLNETKE ENLSRPKWKI KNKDWLEFVW  1260
ERNR                                                              1264

SEQ ID NO: 11          moltype = AA  length = 1373
FEATURE                Location/Qualifiers
source                 1..1373
                       mol_type = protein
                       organism = Moraxella bovoculi
SEQUENCE: 11
MLFQDFTHLY PLSKTVRFEL FIDRTLEHIH AKNFLSQDET MADMHQKVKV ILDDYHRDFI  60
ADMMGEVKLT KLAEFYDVYL KFRKNPKDDE LQKAQLKDLQ AVLRKEIVKP IGNGGKYKAG  120
YDRLFGAKLF KDGKELGDLA KFVIAQEGES SPKLAHLAHF EKFSTYFTGF HDNRKNMYSD  180
EDKHTAIAYR LIHENLPRFI DNLQILTTIK QKHSALYDQI INELTASGLD VSLASHLDGY  240
HKLLTQEGIT AYNTLLGGIS GEAGSPKIQG INELINSHHN QHCHKSERIA KLRPLHKQIL  300
SDGMSVSFLP SKFADDSEMC QAVNEFYRHY ADVFAKVQSL FDGFDDHQKD GIYVEHKNLN  360
ELSKQAFGDF ALLGRVLDGY YVDVVNPEFN ERFAKAKTDN AKAKLTKEKD KFIKGVHSLA  420
SLEQAIEHYT ARHDDESVQA GKLGQYFKHG LAGVDNPIQK IHNNHSTIKG FLERERPAGE  480
RALPKIKSGK NPEMTQLRQL KELLDNALNV AHFAKLLTTK TTLDNQDGNF YGEFGVLYDE  540
LAKIPTLYNK VRDYLSQKPF STEKYKLNFG NPTLLNGWDL NKEKDNFGVI LQKDGCYYLA  600
LLDKAHKKVF DNAPNTGKSI YQKMIYKYLE VRKQFPKVFF SKEAIAINYH PSKELVEIKD  660
KGRQRSDDER LKLYRFILEC LKIHPKYDKK FEGAIGDIQL FKKDKKGREV PISEKDLFKD  720
INGIFSSKPK LEMEDFFIGE FKRYNPSQDL VDQYNIYKKI DSNDNRKKEN FYNNHPKFKK  780
DLVRYYYESM CKHEEWEESF EFSKKLQDIG CYVDVNELFT EIETRRLNYK ISFCNINADY  840
IDELVEQGQL YLFQIYNKDF SPKAHGKPNL HTLYFKALFS EDNLADPIYK LNGEAQIFYR  900
KASLDMNETT IHRAGEVLEN KNPDNPKKRQ FVYDIIKDKR YTQKDFMLHV PITMNFGVQG  960
MTIKEFNKKV NQSIQQYDEV NVIGIDRGER HLLYLTVINS KGEILEQCSL NDITTASANG  1020
TQMTTPYHKI LDKREIERLN ARVGWGEIET IKELKSGYLS HVVHQISQLM LKYNAIVVLE  1080
DLNFGFKRGR FKVEKQIYQN FENALIKKLN HLVLKDKADD EIGSYKNALQ LTNNFTDLKS  1140
IGKQTGFLFY VPAWNTSKID PETGFVDLLK PRYENIQASQ AFFGKFDKIC YNADKDYFEF  1200
HIDYAKFTDK AKNSRQIWTI CSHGDKRYVY DKTANQNKGA AKGINVNDIL KSLFARHHIN  1260
EKQPNLVMDI CQNNDKEFHK SLMYLLKTLL ALRYSNASSD EDFILSPVAN DEGVFFNSAL  1320
ADDTQPQNAD ANGAYHIALK GLWLLNELKN SDDLNKVKLA IDNQTWLNFA QNR         1373
```

-continued

```
SEQ ID NO: 12          moltype = AA  length = 1352
FEATURE                Location/Qualifiers
source                 1..1352
                       mol_type = protein
                       note = Parcubacteria bacterium
                       organism = unidentified
SEQUENCE: 12
MENIFDQFIG KYSLSKTLRF ELKPVGKTED FLKINKVFEK DQTIDDSYNQ AKFYFDSLHQ  60
KFIDAALASD KTSELSFQNF ADVLEKQNKI ILDKKREMGA LRKRDKNAVG IDRLQKEIND  120
AEDIIQKEKE KIYKDVRTLF DNEAESWKTY YQEREVDGKK ITESKADLKQ KGADFLTAAG  180
ILKVLKYEFP EEKEKEFQAK NQPSLFVEEK ENPGQKRYIF DSFDKFAGYL TKFQQTKKNL  240
YAADGTSTAV ATRIADNFII FHQNTKVFRD KYKNNHTDLG FDEENIFEIE RYKNCLLQRE  300
IEHIKNENSY NKIIGRINKK IKEYRDQKAK DTKLTKSDFP FFKNLDKQIL GEVEKEKQLI  360
EKTREKTEED VLIERFKEFI ENNEERFTAA KKLMNAFCNG EFESEYEGIY LKNKAINTIS  420
RRWFVSDRDF ELKLPQQKSK NKSEKNEPKV KKFISIAEIK NAVEELDGDI FKAVFYDKKI  480
IAQGGSKLEQ FLVIWKYEFE YLFRDIEREN GEKLLGYDSC LKIAKQLGIF PQEKEAREKA  540
TAVIKNYADA GLGIFQMMKY FSLDDKDRKN TPGQLSTNFY AEYDGYYKDF EFIKYYNEFR  600
NFITKKPFDE DKIKLNFENG ALLKGWDENK EYDFMGVILK KEGRLYLGIM HKNHRKLFQS  660
MGNAKGDNAN RYQKMIYKQI ADASKDVPRL LLTSKKAMEK FKPSQEILRI KKEKTFKRES  720
KNFSLRDLHA LIEYYRNCIP QYSNWSFYDF QFQDTGKYQN IKEFTDDVQK YGYKISFRDI  780
DDEYINQALN EGKMYLFEVV NKDIYNTKNG SKNLHTLYFE HILSAENLND PVFKLSGMAE  840
IFQRQPSVNE REKITTQKNQ CILDKGDRAY KYRRYTEKKI MFHMSLVLNT GKGEIKQVQF  900
NKIINQRISS SDNEMRVNVI GIDRGEKNLL YYSVVKQNGE IIEQASLNEI NGVNYRDKLI  960
EREKERLKNR QSWKPVVKIK DLKKGYISHV IHKICQLIEK YSAIVVLEDL NMRFKQIRGG  1020
IERSVYQQFE KALIDKLGYL VFKDNRDLRA PGGVLNGYQL SAPFVSFEKM RKQTGILFYT  1080
QAEYTSKTDP ITGFRKNVYI SNSASLDKIK EAVKKFDAIG WDGKEQSYFF KYNPYNLADE  1140
KYKNSTVSKE WAIFASAPRI RRQKGEDGYW KYDRVKVNEE FEKLLKVWNF VNPKATDIKQ  1200
EIIKKIKAGD LQGEKELDGR LRNFWHSFIY LFNLVLELRN SFSLQIKIKA GEVIAVDEGV  1260
DFIASPVKPF FTTPNPYIPS NLCWLAVENA DANGAYNIAR KGVMILKKIR EHAKKDPEFK  1320
KLPNLFISNA EWDEAARDWG KYAGTTALNL DH                               1352

SEQ ID NO: 13          moltype = AA  length = 1260
FEATURE                Location/Qualifiers
source                 1..1260
                       mol_type = protein
                       organism = Porphyromonas crevioricanis
SEQUENCE: 13
MDSLKDFTNL YPVSKTLRFE LKPVGKTLEN IEKAGILKED EHRAESYRRV KKIIDTYHKV  60
FIDSSLENMA KMGIENEIKA MLQSFCELYK KDHRTEGEDK ALDKIRAVLR GLIVGAFTGV  120
CGRRENTVQN EKYESLFKEK LIKEILPDFV LSTEAESLPF SVEEATRSLK EFDSFTSYFA  180
GFYENRKNIY STKPQSTAIA YRLIHENLPK FIDNILVFQK IKEPIAKELE HIRADFSAGG  240
YIKKDERLED IFSLNYYIHV LSQAGIEKYN ALIGKIVTEG DGEMKGLNEH INLYNQQRGR  300
EDRLPLFRPL YKQILSDREQ LSYLPESFEK DEELLRALKE FYDHIAEDIL GRTQQLMTSI  360
SEYDLSRIYV RNDSQLTDIS KKMLGDWNAI YMARERAYDH EQAPKRITAK YERDRIKALK  420
GEESISLANL NSCIAFLDNV RDCRVDTYLS TLGQKEGPHG LSNLVENVFA SYHEAEQLLS  480
FPYPEENNLI QDKDNVVLIK NLLDNISDLQ RFLKPLWGMG DEPDKDERFY GEYNYIRGAL  540
DQVIPLYNKV RNYLTRKPYS TRKVKLNFGN SQLLSGWDRN KEKDNSCVIL RKGQNFYLAI  600
MNNRHKRSFE NKMLPEYKEG EPYFEKMDYK FLPDPNKMLP KVFLSKKGIE IYKPSPKLLE  660
QYGHGTHKKG DTFSMDDLHE LIDFFKHSIE AHEDWKQFGF KFSDTATYEN VSSFYREVED  720
QGYKLSFRKV SESYVYSLID QGKLYLFQIY NKDFSPCSKG TPNLHTLYWR MLFDERNLAD  780
VIYKLDGKAE IFFREKSLKN DHPTHPAGKP IKKKSRQKKG EESLFEYDLV KDRRYTMDKF  840
QFHVPITMNF KCSAGSKVND MVNAHIREAK DMHVIGIDRG ERNLLYICVI DSRGTILDQI  900
SLNTINDIDY HDLLESRDKD RQQEHRNWQT IEGIKELKQG YLSQAVHRIA ELMVAYKAVV  960
ALEDLNMGFK RGRQKVESSV YQQFEKQLID KLNYLVDKKK RPEDIGGLLR AYQFTAPFKS  1020
FKEMGKQNGF LFYIPAWNTS NIDPTTGFVN LFHVQYENVD KAKSFFQKFD SISYNPKKDW  1080
FEFAFDYKNF TKKAEGSRSM WILCTHGSRI KNFRNSQKNG QWDSEEFALT EAFKSLFVRY  1140
EIDYTADLKT AIVDEKQKDF FVDLLKLFKL TVQMRNSWKE KDLDYLISPV AGADGRFFDT  1200
REGNKSLPKD ADANGAYNIA LKGLWALRQI RQTSEGGKLK LAISNKEWLQ FVQERSYEKD  1260

SEQ ID NO: 14          moltype = AA  length = 1324
FEATURE                Location/Qualifiers
source                 1..1324
                       mol_type = protein
                       organism = Prevotella disiens
SEQUENCE: 14
MENYQEFTNL FQLNKTLRFE LKPIGKTCEL LEEGKIFASG SFLEKDKVRA DNVSYVKKEI  60
DKKHKIFIEE TLSSFSISND LLKQYFDCYN ELKAFKKDCK SDEEEVKKTA LRNKCTSIQR  120
AMREAISQAF LKSPQKKLLA IKNLIENVFK ADENVQHFSE FTSYFSGFET NRENFYSDEE  180
KSTSIAYRLV HDNLPIFIKN IYIFEKLKEQ FDAKTLSEIF ENYKLYVAGS SLDEVFSLEY  240
FNNTLTQKGI DNYNAVIGKI VKEDKQEIQG LNEHINLYNQ KHKDRRLPFF ISLKKQILSD  300
REALSWLPDM FKNDSEVIDA LKGFYIEDGF ENNVLTPLAT LLSSLDKYNL NGIFIRNNEA  360
LSSLSQNVYR NFSIDEAIDA QNAELQTFNN YELIANALRA KIKKETKQGR KSFEKYEEYI  420
DKKVKAIDSL SIQEINELVE NYVSEFNSNS GNMPRKVEDY FSLMRKGDFG SNDLIENIKT  480
KLSAAEKLLG TKYQETAKDI FKKDENSKLI KELLDATKQF QHFIKPLLGT GEEADRDLVF  540
YGDFLPLYEK FEELTLLYNK VRNRLTQKPY SKDKIRLCFN KPKLMTGWVD SKTEKSDNGT  600
QYGGYLFRKK NEIGEYDYFL GISSKAQLFR KNEAVIGDYE RLDYYQPKAN TIYGSAYEGE  660
NSYKEDKKRL NKVIIAYIEQ IKQTNIKKSI IESISKYPNI SDDDKVTPSS LLEKIKKVSI  720
DSYNGILSFK SFQSVNKEVI DNLLKTISPL KNKAEFLDLI NKDYQIFTEV QAVIDEICKQ  780
```

-continued

```
KTFIYFPISN VELEKEMGDK DKPLCLFQIS NKDLSFAKTF SANLRKKRGA ENLHTMLFKA  840
LMEGNQDNLD LGSGAIFYRA KSLDGNKPTH PANEAIKCRN VANKDKVSLF TYDIYKNRRY  900
MENKFLFHLS IVQNYKAAND SAQLNSSATE YIRKADDLHI IGIDRGERNL LYYSVIDMKG  960
NIVEQDSLNI IRNNDLETDY HDLLDKREKE RKANRQNWEA VEGIKDLKKG YLSQAVHQIA  1020
QLMLKYNAII ALEDLGQMFV TRGQKIEKAV YQQFEKSLVD KLSYLVDKKR PYNELGGILK  1080
AYQLASSITK NNSDKQNGFL FYVPAWNTSK IDPVTGFTDL LRPKAMTIKE AQDFFGAFDN  1140
ISYNDKGYFE FETNYDKFKI RMKSAQTRWT ICTFGNRIKR KKDKNYWNYE EVELTEEFKK  1200
LFKDSNIDYE NCNLKEEIQN KDNRKFFDDL IKLLQLTLQM RNSDDKGNDY IISPVANAEG  1260
QFFDSRNGDK KLPLDADANG AYNIARKGLW NIRQIKQTKN KDDLNLSISS TEWLDFVREK  1320
PYLK                                                              1324

SEQ ID NO: 15          moltype = AA  length = 1484
FEATURE                Location/Qualifiers
VARIANT                1073
                       note = Xaa can be any naturally occurring amino acid
source                 1..1484
                       mol_type = protein
                       note = Peregrinibacteria bacterium
                       organism = unidentified
SEQUENCE: 15
MSNFFKNFTN LYELSKTLRF ELKPVGDTLT NMKDHLEYDE KLQTFLKDQN IDDAYQALKP  60
QFDEIHEEFI TDSLESKKAK EIDFSEYLDL FQEKKELNDS EKKLRNKIGE TFNKAGEKWK  120
KEKYPQYEWK KGSKIANGAD ILSCQDMLQF IKYKNPEDEK IKNYIDDTLK GFFTYFGGFN  180
QNRANYYETK KEASTAVATR IVHENLPKFC DNVIQFKHII KRKKDGTVEK TERKTEYLNA  240
YQYLKNNNKI TQIKDAETEK MIESTPIAEK IFDVYYFSSC LSQKQIEEYN RIIGHYNLLI  300
NLYNQAKRSE GKHLSANEKK YKDLPKFKTL YKQIGCGKKK DLFYTIKCDT EEEANKSRNE  360
GKESHSVEEI INKAQEAINK YFKSNNDCEN INTVPDFINY ILTKENYEGV YWSKAAMNTI  420
SDKYFANYHD LQDRLKEAKV FQKADKKSED DIKIPEAIEL SGLFGVLDSL ADWQTTLFKS  480
SILSNEKLKI ITDSQTPSEA LLKMIFNDIE KNMESFLKET NDIITLKKYK GNKEGTEKIK  540
QWFDYTLAIN RMLKYFLVKE NKIKGNSLDT NISEALKTLI YSDDAEWFKW YDALRNYLTQ  600
KPQDEAKENK LKLNFDNPSL AGGWDVNKEC SNFCVILKDK NEKKYLAMIK KGENTLFQKE  660
WTEGRGKNLT KKSNPLFEIN NCEILSKMEY DFWADVSKMI PKCSTQLKAV VNHFKQSDNE  720
FIFPIGYKVT SGEKFREECK ISKQDFELNN KVFNKNELSV TAMRYDLSST QEKQYIKAFQ  780
KEYWELLFKQ EKRDTKLTNN EIFNEWINFC NKKYSELLSW ERKYKDALTN WINFCKYFLS  840
KYPKTTLFNY SFKESENYNS LDEFYRDVDI CSYKLNINTT INKSILDRLV EEGKLYLFEI  900
KNQDSNDGKS IGHKNNLHTI YWNAIFENFD NRPKLNGEAE IFYRKAISKD KLGIVKGKKT  960
KNGTWIIKNY RFSKEKFILH VPITLNFCSN NEYVNDIVNT KFYNFSNLHF LGIDRGEKHL  1020
AYYSLVNKNG EIVDQGTLNL PFTDKDGNQR SIKKEKYFYN KQEDKWEAKE VDXWNYNDLL  1080
DAMASNRDMA RKNWQRIGTI KEAKNGYVSL VIRKIADLAV NNERPAFIVL EDLNTGFKRS  1140
RQKIDKSVYQ KFELALAKKL NFLVDKNAKR DEIGSPTKAL QLTPPVNNYG DIENKKQAGI  1200
MLYTRANYTS QTDPATGWRK TIYLKAGPEE TTYKKDGKIK NKSVKDQIIE TFTDIGFDGK  1260
DYYFEYDKGE FVDEKTGEIK PKKWRLYSGE NGKSLDRFRG EREKDKYEWK IDKIDIVKIL  1320
DDLFVNFDKN ISLLKQLKEG VELTRNNEHG TGESLRFAIN LIQQIRNTGN NERDNDFILS  1380
PVRDENGKHF DSREYWDKET KGEKISMPSS GDANGAFNIA RKGIIMNAHI LANSDSKDLS  1440
LFVSDEEWDL HLNNKTEWKK QLNIFSSRKA MAKRKKKRPA ATKK                  1484

SEQ ID NO: 16          moltype = AA  length = 1245
FEATURE                Location/Qualifiers
source                 1..1245
                       mol_type = protein
                       organism = Porphyromonas macacae
SEQUENCE: 16
MKTQHFFEDF TSLYSLSKTI RFELKPIGKT LENIKKNGLI RRDEQRLDDY EKLKKVIDEY  60
HEDFIANILS SFSFSEEILQ SYIQNLSISE ARAKIEKTMR DTLAKAFSED ERYKSIFKKE  120
LVKKDIPVWC PAYKSLCKKF DNFTTSLVPF HENRKNLYTS NEITASIPYR IVHVNLPKFI  180
QNIEALCELQ KKMGADLYLE MMENLRNVWP SFVKTPDDLC NLKTYNHLMV QSSISEYNRF  240
VGGYSTEDGT KHQGINEWIN IYRQRNKEMR LPGLVFLHKQ ILAKVDSSSF ISDTLENDDQ  300
VFCVLRQFRK LFWNTVSSKE DDAASLKDLF CGLSGYDPEA IYVSDAHLAT ISKNIFDRWN  360
YISDAIRRKT EVLMPRKKES VERYAEKISK QIKKRQSYSL AELDDLLAHY SEESLPAGFS  420
LLSYFTSLGG QKYLVSDGEV ILYEEGSNIW DEVLIAFRDL QVILDKDFTE KKLGKDEEAV  480
SVIKKALDSA LRLRKFFDLL SGTGAEIRRD SSFYALYTDR MDKLKGLLKM YDKVRNYLTK  540
KPYSIEKFKL HFDNPSLLSG WDKNKELNNL SVIFRQNGYY YLGIMTPKGK NLFKTLPKLG  600
AEEMFYEKME YKQIAEPMLM LPKVFFPKKT KPAFAPDQSV VDIYNKKTFK TGQKGFNKKD  660
LYRLIDFYKE ALTVHEWKLF NFSFSPTEQY RNIGEFFDEV REQAYKVSMV NVPASYIDEA  720
VENGKLYLFQ IYNKDFSPYS KGIPNLHTLY WKALFSEQNQ SRVYKLCGGG ELFYRKASLH  780
MQDTTVHPKG ISIHKKNLNK KGETSLFNYD LVKDKRFTED KFFFHVPISI NYKNKKITNV  840
NQMVRDYIAQ NDDLQHGIDR GERNLLYISR IDTRGNLLEQ FSLNVIESDK GDLRTDYQKI  900
LGDREQERLR RRQEWKSIES IKDLKDGYMS QVVHKICNMV VEHKAIVVLE NLNLSFMKGR  960
KKVEKSVYEK FERMLVDKLN YLVVDKKNLS NEPGGLYAAY QLTNPLFSFE ELHRYPQSGI  1020
LFFVDPWNTS LTDPSTGFVN LLGRINYTNV GDARKFFDRF NAIRYDGKGN ILFDLDLSRF  1080
DVRVETQRKL WTLTTFGSRI AKSKKSGKWM VERIENLSLC FLELFEQFNI GYRVEKDLKK  1140
AILSQDRKEF YVRLIYLFNL MMQIRNSDGE EDYILSPALN EKNLQFDSRL IEAKDLPVDA  1200
DANGAYNVAR KGLMVVQRIK RGDHESIHRI GRAQWLRYVQ EGIVE                 1245

SEQ ID NO: 17          moltype = AA  length = 1250
FEATURE                Location/Qualifiers
source                 1..1250
                       mol_type = protein
                       organism = Smithella sp.
```

-continued

```
SEQUENCE: 17
MQTLFENFTN QYPVSKTLRF ELIPQGKTKD FIEQKGLLKK DEDRAEKYKK VKNIIDEYHK  60
DFIEKSLNGL KLDGLEKYKT LYLKQEKDDK DKKAFDKEKE NLRKQIANAF RNNEKFKTLF  120
AKELIKNDLM SFACEEDKKN VKEFEAFTTY FTGFHQNRAN MYVADEKRTA IASRLIHENL  180
PKFIDNIKIF EKMKKEAPEL LSPFNQTLKD MKDVIKGTTL EEIFSLDYFN KTLTQSGIDI  240
YNSVIGGRTP EEGKTKIKGL NEYINTDFNQ KQTDKKKRQP KFKQLYKQIL SDRQSLSFIA  300
EAFKNDTEIL EAIEKFYVNE LLHFSNEGKS TNVLDAIKNA VSNLESFNLT KMYFRSGASL  360
TDVSRKVFGE WSIINRALDN YYATTYPIKP REKSEKYEER KEKWLKQDFN VSLIQTAIDE  420
YDNETVKGKN SGKVIADYFA KFCDDKETDL IQKVNEGYIA VKDLLNTPCP ENEKLGSNKD  480
QVKQIKAFMD SIMDIMHFVR PLSLKDTDKE KDETFYSLFT PLYDHLTQTI ALYNKVRNYL  540
TQKPYSTEKI KLNFENSTLL GGWDLNKETD NTAIILRKDN LYYLGIMDKR HNRIFRNVPK  600
ADKKDFCYEK MVYKLLPGAN KMLPKVFFSQ SRIQEFTPSA KLLENYANET HKKGDNFNLN  660
HCHKLIDFFK DSINKHEDWK NFDFRFSATS TYADLSGFYH EVEHQGYKIS FQSVADSFID  720
DLVNEGKLYL FQIYNKDFSP FSKGKPNLHT LYWKMLFDEN NLKDVVYKLN GEAEVFYRKK  780
SIAEKNTTIH KANESIINKN PDNPKATSTF NYDIVKDKRY TIDKFQFHIP ITMNFKAEGI  840
FNMNQRVNQF LKANPDINII GIDRGERHLL YYALINQKGK ILKQDTLNVI ANEKQKVDYH  900
NLLDKKEGDR ATARQEWGVI ETIKELKEGY LSQVIHKLTD LMIENNAIIV MEDLNFGFKR  960
GRQKVEKQVY QKFEKMLIDK LNYLVDKNKK ANELGGLLNA FQLANKFESF QKMGKQNGFI  1020
FYVPAWNTSK TDPATGFIDF LKPRYENLNQ AKDFFEKFDS IRLNSKADYF EFAFDFKNFT  1080
EKADGGRTKW TVCTTNEDRY QWNRALNNNR GSQEKYDITA ELKSLFDGKV DYKSGKDLKQ  1140
QIASQESADF FKALMKNLSI TLSLRHNNGE KGDNEQDYIL SPVADSKGRF FDSRKADDDM  1200
PKNADANGAY HIALKGLWCL EQISKTDDLK KVKLAISNKE WLEFVQTLKG             1250

SEQ ID NO: 18           moltype = DNA  length = 3987
FEATURE                 Location/Qualifiers
source                  1..3987
                        mol_type = other DNA
                        organism = synthetic construct
SEQUENCE: 18
atggccggga gcaagaagcg ccggataaag caggacacgc agttcgaggg cttcaccaac  60
ctgtaccaag tctccaagac gctccggttc gagcttatcc cgcaagggaa gaccctgaaa  120
cacatccagg aacaaggttt catcgaggag gacaaggccc gcaacgacca ctacaaggag  180
ctcaagccca taatcgatcg gatctacaag acgtacgccg accagtgcct ccaactggtg  240
cagctcgact gggagaacct gagcgccgcc attgacagct accgcaagga aaagacggag  300
gagacgcgca acgcccttat tgaggagcaa gccacctacc gcaacgccat ccacgactac  360
ttcatcgggc gcaccgacaa cctgacggac gcgatcaaca agcgccacgc ggaaatctac  420
aagggccttt tcaaggccga gctcttcaac gggaaggtcc taaaacagct cgggactgtc  480
acgacaaccg agcatgagaa cgccctcctt cgcagcttcg acaagttcac cacatacttc  540
tcgggcttct accggaaccg caagaacgtt ttcagcgccg aggacatctc caccgccatc  600
ccgcacagga tcgtccagga caacttcccc aagttcaagg agaactgcca catcttcacg  660
cgcctgatta cagccgtacc ttcacttcgt gagcacttcg agaacgtcaa aaaggccatc  720
gggatcttcg tctccacgtc catcgaggag gtattctctt tcccgttcta taaccagctc  780
ctgacccaga cgcagatcga cctctacaac cagctactgg gcggcatcag ccgggaggcc  840
gggaccgaga aaataaaggg cctcaacgaa gttctcaacc tggccatcca gaagaacgac  900
gagaccgcgc atatcatcgc atccctgccg catcgcttca ttcctttgtt caagcagata  960
ttgagcgacc ggaacaccct ctcgttcatc ctcgaagaat tcaagagcga cgaggaggtc  1020
attcagtctt tctgcaagta caagacgctc ctacggaatg agaatgtgct ggagaccgcg  1080
gaggcactct tcaatgagct gaactccatt gacctgaccc acatcttcat tagccacaag  1140
aaactggaga cgatctccag cgccctgtgc gaccactggg acactctccg caacgccctc  1200
tacgaacgcc ggatctccga acttaccggc aagataacta agtcggctaa ggagaaggtg  1260
caacggagcc tcaagcacga ggacatcaac cttcaggaaa tcatctcagc cgcgggcaag  1320
gagctgagcg aggcgtttaa gcagaaaaca tcggagatac tgagccacgc gcacgcggcc  1380
ctggatcaac cgctgccgac gactctcaag aagcaagagg agaaggaaat ccttaagtcc  1440
cagctcgact cgctgctcgg cctctatcac ttgctcgact ggttcgcggt tgatgagtcc  1500
aacgaggtgg acccggagtt ctccgcgcgc ctcacgggta ttaagctgga gatggagcca  1560
agcttaagct tctacaacaa ggcccgcaac tacgcgacca aaaaaccgta ctcagtcgag  1620
aaattcaagc tgaatttcca gatgcctaca ttggcgaggg ggtgggacgt gaaccgcgag  1680
aagaacaatg gagccatcct gttcgtcaaa aatgggttgt actacctggg catcatgccc  1740
aagcagaagg gccgttacaa ggccctgtca ttcgagccta ccgagaagac ctcggagggc  1800
ttcgacaaga tgtactacga ctatttcccg gacgccgcca agatgatccc gaagtgctcc  1860
acgcagctca aagccgtcac ggcccacttc cagacgcata ccacgccgat acttctgagc  1920
aacaacttca ttgagccgct agagatcacg aaggagatat acgacctaaa caaccccgaa  1980
aaggagccca agaagttcca gacagcctac gctaagaaga caggtgatca gaagggatat  2040
agggaggcac tctgcaagtg gatcgacttc acgcgcgact tcctgtcgaa atatacaaag  2100
acgaccagca ttgacctaag ttctctccgc ccatcctccc agtacaagga tctgggcgag  2160
tattatgcgg agctgaaccc attgctgtac cacatcagct tccagaggat cgccgagaag  2220
gagattatgg acgcggtgga gacggggaaa ctatacctgt tccaaatata taacaaggac  2280
ttcgctaaag ggcaccacgg gaagcccaac ctgcacacac tctactggac gggcttgttt  2340
tcgccagaaa atttggccaa gacttcgatc aagctcaacg gccaggcgga gttgttttac  2400
cgtcccaagt ctcgcatgaa gcgcatggcg catcgcctcg gagagaaaat gcttaacaag  2460
aagctcaagg atcagaagac gcccataccc gatacgttgt accaggaatt gtacgactac  2520
gtgaaccacc gcctatcgca cgacctctca gacgaggccc gcgccctcct cccaaacgtg  2580
attactaagg aggtttccca tgaaataatc aaggaccgac ggttcaccag cgacaaattt  2640
tttttccacg tgcctatcac gctcaattac caggcggcca actccccatc gaagttcaac  2700
cagcgcgtga acgcctacct taaggagcac ccggagaccc caatcatcgg gatcgaccgt  2760
ggcgagcgga acctgatcta tattacggtg atcgatagca ccgggaagat cctggagcag  2820
cgctccctga acacaatcca gcagtttgac taccagaaga aactcgacaa ccgggagaag  2880
gagcgcgtcg cagcccggca agcatggagt gtggtcggca ccataaagga cctgaaacag  2940
ggttacctaa gtcaagttat ccacgagatc gttgacctga tgatacacta tcaagccgta  3000
```

-continued

```
gtcgtgctgg agaacctcaa cttcgggttt aagtccaagc gcaccggcat cgcggagaag  3060
gcggtgtacc agcagttcga gaagatgctg atcgacaagc tgaactgcct ggtgctcaag  3120
gactaccctg cggagaaggt cggcggggtc ttgaacccgt accagctaac cgaccagttc  3180
acgagcttcg ccaaaatggg cacgcagtcc ggattcttgt tttatgtccc ggctccatat  3240
acaagtaaga tcgacccgct gacagggttt gttgacccat tcgtgtggaa gaccatcaag  3300
aaccacgaga gcaggaaaca cttcttagag ggcttcgact tcctgcatta cgacgttaag  3360
acaggcgact tcatcctgca cttcaagatg aaccgcaacc tgtcgttcca gaggggcctg  3420
cccggcttca tgcccgcctg ggatatcgtc tttgagaaga atgagacgca gttcgacgcg  3480
aaggggacgc cgttcatcgc tggaaagcgg atcgtgccgg tcatcgagaa ccaccgcttc  3540
acgggtcgct accgagattt ataccccgcc aacgaactaa ttgcgctgct ggaggagaag  3600
gggatcgtgt tccgagatgg cagcaacatt ctcccgaagc tgctggagaa cgacgactcg  3660
cacgctattg acacgatggt cgccctcata cggagcgtgc ttcagatgcg gaacagtaac  3720
gctgccacgg gcgaggacta cattaactcc cccgtccgcg acctcaacgg ggtctgcttc  3780
gatagccgct tccagaaccc ggagtggcct atggatgcgg acgcgaacgg ggcctaccac  3840
atcgccctca agggccaact cctgctcaac cacttgaagg aaagcaaaga cctcaaattg  3900
cagaatggca tcagtaacca ggactggctc gcgtacatcc aggaactgag aaacgggtcc  3960
aagaagcggc gtatcaagca agattga                                     3987

SEQ ID NO: 19          moltype = DNA  length = 3987
FEATURE                Location/Qualifiers
source                 1..3987
                       mol_type = other DNA
                       organism = synthetic construct
SEQUENCE: 19
atggcgggaa gcaaaaagcg ccggattaag caagacacgc agttcgaggg cttcacgaac  60
ctctaccaag tcagcaagac cctccggttc gagctgatac cacagggaaa gacgctcaag  120
cacatccagg aacagggctt catcgaggag gacaaggcgc gcaacgacca ctacaaggag  180
ttgaaaccga tcatcgaccg catctacaag acgtacgccg accagtgcct ccagctcgtg  240
cagctcgact gggagaacct ctccgccgcc attgactcgt accggaagga gaagactgag  300
gagacccgca acgccctgat cgaggagcaa gcaacctacc ggaacgccat ccacgactac  360
ttcatcggcc gcaccgacaa cctcaccgac gcgatcaaca agcggcacgc ggagatatac  420
aaagggctgt tcaaggcgga gctgttcaac ggcaaggtgc tcaagcagct agggacggtg  480
accacgaccg agcacgagaa cgcgctcctc cgcagcttcg acaagttcac cacctacttc  540
agcggcttct accggaaccg caagaatgtg ttcagcgcgg aggacatcag cacggccatc  600
ccgcaccgca tcgtccagga caacttcccg aagttcaagg agaactgcca catcttcacc  660
cgcctgataa ccgccgtccc ctccctgcgg gagcacttcg agaacgtcaa aaaggcaatt  720
gggatcttcg tctcgaccag cattgaggag gtgttcagct tccccttcta caaccagctc  780
ctcacccaga cgcagatcga cctgtacaat cagttgctcg gcgggataag ccgcgaggcg  840
ggaaccgaaa aaatcaaggg gctgaacgaa gtgttgaacc tcgccatcca gaagaacgac  900
gagaccgcgc acatcatcgc ctccctgccc caccggttca tcccgctgtt caagcagatc  960
ctctctgacc ggaacaccct gtccttcatt cttgaggagt tcaagtcgga cgaggaggtc  1020
atccagagct tctgcaagta caagacgctg ctacggaacg agaacgtgct ggagacggcg  1080
gaggcactgt tcaacgagct aaacagcatc gacctcacgc acatcttcat cagtcacaag  1140
aaactggaga ccatctcctc cgcgctgtgc gaccactggg acacgctcag gaacgcgctc  1200
tacgagcgcc gaatcagtga gctgacgggc aagatcacga agtccgcgaa ggagaaggtg  1260
cagcggtccc tcaagcacga ggacatcaac ctccaggaga tcatctcagc ggctgggaaa  1320
gagctgtccg aggcgttcaa gcagaaaacg agcgaaatcc tgtcccacgc gcacgcggcc  1380
ctggatcagc ctctgccgac gaccctcaag aaacaagaag aaaaggaaat cctcaagtcg  1440
cagctcgact cgctgctggg cctgtaccat ctcctcgact ggttcgccgt ggacgagagc  1500
aacgaggtgg accccgagtt ctccgcgcgg cttacgggga tcaagctgga gatggagccc  1560
agcctgtcct tctacaacaa ggcgcgcaac tacgccacca agaagcccta cagcgtggag  1620
aagttcaagc tcaacttcca gatgcccact ctcgcacgtg ggtgggacgt caaccgcgaa  1680
aaaaataatg gggcgatcct gttcgtcaag aacggcctgt actacttggg catcatgccg  1740
aaacagaagg gccgctacaa ggccctgagc ttcgaaccga ccgagaaaac gagcgagggg  1800
ttcgacaaga tgtactacga ctacttcccc gacgccgcga agatgattcc aaagtgctcc  1860
acgcagctta aggccgtgac ggcccacttc cagacgcaca cgaccccgat cctcctcagc  1920
aacaacttca tcgagcccct ggagatcacg aaggagatat acgacctgaa caacccggag  1980
aaggagccca agaaattcca gaccgcctac gccaagaaga caggcgacca aaagggttac  2040
agggaggccc tctgcaagtg gatcgacttc actagggact tcctgtccaa gtacaccaag  2100
actacctcta tcgacctgtc cagcctccgc ccgtcgtccc agtacaaaga tttgggcgag  2160
tattacgcgg agctgaaccc actgctctac cacatcagct tccagcgcat cgcggagaag  2220
gagatcatgg acgcagtgga gacgggcaag ctatacctat ttcagatata caacaaagac  2280
ttcgctaagg gacaccacgg caagcctaac ctgcacaccc tctactggac ggggctcttc  2340
agcccggaga acctcgccaa gacctcgatc aagctcaacg gccaggccga gctgttctac  2400
cggcccaagt cccgcatgaa gcggatggcc caccggctcg ggagaaaat gctcaacaag  2460
aaattgaagg accaaaaaac gccgataccc gacaccctat accaggagct gtacgactat  2520
gtgaaccacc gcctgagcca cgacctcagc gacgaggcgc gggccctcct gccgaacgtc  2580
atcacaaagg aggtcagcca cgagatcatc aaggaccggc gcttcacctc cgacaagttt  2640
ttctttcacg tgcccatcac gctcaactac caggccgcca actcgccgtc caagttcaac  2700
cagcgcgtga acgcctacct caaggagcac cccgagaccc cgatcatcgg gattgaccga  2760
ggggagcgga acctcatcta catcaccgtc atcgacagca ccgggaagat ccttgaacag  2820
cggtcgctca acaccatcca gcagttcgac taccagaaga aactcgacaa ccgggagaag  2880
gagagagtgg cggcccgcca ggcttggtcc gtcgtcggga cgattaagga cttgaaacaa  2940
ggttacctgt cgcaagtgat ccacgagatc gttgacctga tgatccacta ccaagccgtc  3000
gtggtcctgg agaacctcaa cttcggcttc aagagcaaac gaaccggcat cgcggagaag  3060
gccgtgtacc agcagttcga aaaaatgctg atcgacaagc tgaactgcct cgtgctcaag  3120
gactaccccg ctgagaaggt cggcggggtg ctgaacccgt accagctcac tgaccagttc  3180
accagcttcg caaagatggg cacccagtcc ggcttcctgt tctacgtgcc tgcgccatac  3240
acctcgaaga tcgacccgct caccgggttc gtggacccct tcgtctggaa gaccatcaag  3300
```

-continued

```
aaccacgaga gccgcaagca cttcctggag ggcttcgact tcctccacta cgacgtcaag  3360
accggggact tcatcctgca cttcaagatg aaccgcaacc tcagtttcca gcgcggcctg  3420
ccggggttca tgcccgcttg ggatatagtc ttcgagaaga atgagacgca gttcgacgcg  3480
aagggcaccc cgttcatcgc cgggaagcgc atcgtgccgg tcatcgagaa ccaccggttc  3540
accgggcgct accgcgacct atacccggcg aacgagttga tcgccctcct ggaggagaag  3600
ggcatcgtgt tccgcgacgg ctccaacatc ctcccgaagc tgctcgaaaa cgacgactcc  3660
cacgccatcg acacgatggt cgcgctgatc cggtcggtgc tccagatgcg gaactccaac  3720
gccgcgacgg gcgaggacta catcaacagt ccggtccgcg atctgaacgg cgtctgcttc  3780
gactcccggt tccagaaccc cgagtggccg atggacgcgg acgcgaacgg cgcataccac  3840
atcgccctaa aagggcaatt gctgctcaac cacctcaagg aatccaaaga cctaaagctc  3900
cagaacggca tctccaacca ggactggctg gcgtacatcc aggaactgcg gaacgggagc  3960
aaaaaacgtc ggatcaagca agattga                                    3987

SEQ ID NO: 20          moltype = DNA  length = 3987
FEATURE                Location/Qualifiers
source                 1..3987
                       mol_type = other DNA
                       organism = synthetic construct
SEQUENCE: 20
atggcgggct ccaagaaacg ccggattaag caagataccc agttcgaggg gttcacgaac  60
ctctaccaag tgagcaagac cctccgattc gaactgattc ctcaggggaa gaccctcaag  120
cacatccagg agcaagggtt catcgaggag gacaaggcgc ggaacgacca ctacaaggaa  180
ctcaaaccca tcatcgaccg catctacaag acctacgccg atcagtgcct ccagctcgtg  240
cagttggact gggagaacct cagcgcggcc attgactcct accggaagga gaaaacggag  300
gagacgcgca acgcgctcat cgaggaacag gcaacctatc gcaacgccat ccacgactac  360
ttcatcggga ggactgacaa cctcactgac gcgattaaca agcgccacgc ggagatatac  420
aagggactct tcaaagcgga gctgtttaac ggcaaggttc tcaagcaact cggcactgtg  480
accacgaccg agcatgagaa cgccctgctc cgctccttcg acaagttcac cacctacttc  540
tccgggttct accgcaaccg caagaatgtc ttcagcgcgg aggacatcag cacggccatt  600
ccacatcgaa tcgtccaaga taacttcccg aagttcaagg agaactgcca catcttcacc  660
cgactcatta ctgctgtacc gtcgttacgc gaacacttcg agaacgtcaa gaaggcaatt  720
ggaatcttcg tctctacgtc aatagaggag gtgttcagct tccctttcta caaccagctc  780
cttacgcaga cccagataga cctgtacaat cagctcctcg gtgggatcag ccgggaggcg  840
gggactgaga agattaaagg gctcaacgag gtcttgaacc tggccatcca aaaaaacgat  900
gagacggcgc acatcatcgc ctcgctgccc caccggttca tcccgctgtt caagcagatc  960
ctcagtgaca ggaacacctt gagctttatc ctagaggagt tcaagagcga cgaggaggtg  1020
atccagagct tctgcaagta caaaaccctg ctgaggaacg agaacgtcct ggagacggcg  1080
gaggcgctgt tcaacgagct gaactctatc gacttaactc acatattcat ctcgcacaag  1140
aagctggaga ctattagctc tgcactctgc gaccactggg acaccctccg caacgcgctc  1200
tacgagcgcc gcatctcgga gctgaccggg aagatcacca aatccgcgaa ggaaaaggtc  1260
cagcgttccc tcaaacacga ggatattaac ttacaggaga ttatctcagc ggctgggaag  1320
gagttgtcag aggcgttcaa gcagaaaact tccgagatcc tgagccacgc gcacgcagcg  1380
ctcgaccagc ctctgcccac caccctcaaa aagcaggaag aaaaagagat cctcaagagc  1440
cagttggact ccctgctggg gctctatcac cttctcgact ggttcgccgt cgatgagtcg  1500
aacgaggtgg accccgagtt ctccgcccgg ctgaccggca tcaagctaga gatggagccg  1560
tccctcagct tctacaataa ggcccgcaac tacgcgacca aaaaaccta cagcgtggag  1620
aagttcaagc tgaacttcca gatgccgacc ttagcacgcg gttgggacgt aaacagggag  1680
aagaacaatg gagccatcct gttcgtcaag aacgggcttt actacctcgg gataatgccc  1740
aagcagaagg gccgctacaa ggccctttcc ttcgagccga cggagaaaac ctccgagggg  1800
ttcgacaaga tgtactacga ctacttcccc gacgccgcca agatgatccc gaagtgctca  1860
acgcagctaa aagccgtgac cgcccacttc cagacccaca cgacgccgat cctgctgagc  1920
aacaacttca tcgagcccct tgagatcact aaggagatat acgacctgaa caaccccgag  1980
aaggagccca agaagtttca aaccgcctac gccaaaaaaa ctggcgacca aaagggctac  2040
agggaggcgc tgtgtaagtg gatcgacttc acacgcgact tcctttcgaa gtatacgaag  2100
acaacctcta ttgacctgag cagcctgcgt cctagctccc agtacaaaga tttgggcgag  2160
tactacgcgg agcttaatcc actactctac cacatctcat tccagcgcat cgctgagaag  2220
gaaatcatgg acgcggtgga gacaggcaaa ctgtacctct tccagatata caacaaagac  2280
ttcgctaagg ggcaccacgg gaagcccaac cttcatacgc tctactggac gggcctattc  2340
agccccgaaa atctggccaa gacctccatc aagctgaacg gccaagcgga gctgttctac  2400
agacccaaga gccggatgaa gcggatggcc cacaggctcg gcgagaaaat gcttaacaaa  2460
aagttgaagg accagaaaac ccctatcccc gacaccctct accaggaact gtacgactac  2520
gtgaaccaca ggctctcgca cgacctttcc gacgaggccc gtgccctact cccgaacgtc  2580
attaccaaag aggtttcgca cgagatcatc aaggaccggc ggttcacgag cgacaagttt  2640
ttctttcacg tccccatcac ccttaactac caggcggcca actccccatc caagttcaac  2700
cagcgtgtga atgcctacct caaggagcac ccagagaccc cgatcattgg gatcgaccgg  2760
ggcgagcgga acctgatcta catcaccgtc atcgactcga cgggcaagat tcttgagcag  2820
agatcgttga ataccataca gcagttcgac taccagaaga aactcgacaa ccgcgagaag  2880
gagcgcgtgg cggcccgcca ggcgtggtcc gtcgttggga cgattaagga cttgaaacaa  2940
ggttatctgt cccaagtcat ccacgagatc gttgatctga tgatccacta tcaggcagtg  3000
gtggtgctgg agaatctcaa cttcggcttc aagagtaagc ggacgggaat cgccgagaag  3060
gccgtgtacc agcagttcga gaagatgctg atcgacaagc tcaactgcct tgtgctgaaa  3120
gactacccgg ccgagaaggt cggcggcgtc ctcaacccgt accaacttac cgaccagttc  3180
acctccttcg ccaagatggg cactcagtcc gggttcttgt tctacgtccc cgcaccttac  3240
acctctaaga tcgaccctct gactggcttc gtagatccat tcgtgtggaa gaccattaag  3300
aaccacgaga gccgcaagca cttcctggag ggcttcgact tcctgcacta cgacgtgaag  3360
accggggact tcatccttca cttcaagatg aaccggaacc tcagcttcca gcggggcctg  3420
ccggggttca tgcccgcctg ggacatcgtg ttcgagaaga acgagaccca gttcgacgcg  3480
aagggcacgc ccttcatcgc cgggaagcgt atcgtgccgg tgatcgagaa ccatcgtttc  3540
acgggtcgct accgtgacct ctacccggcg aacgagctta tcgcactcct ggaggagaag  3600
```

-continued

```
ggcatcgtct tccgggacgg ctccaacatc ctcccgaaac tgctggaaaa cgacgactct  3660
cacgccatcg acacgatggt ggccctcatc cggtccgtgc tccaaatgcg gaacagcaac  3720
gccgccaccg gtgaggacta catcaacagc ccggtccggg atctgaacgg ggtgtgcttc  3780
gattcgcggt tccagaatcc tgagtggccg atggacgcgg atgcaaacgg ggcgtaccac  3840
atcgcgctca agggccagtt acttctgaac caccttaagg agtctaaaga tttgaaactc  3900
cagaacggga tctcgaacca ggactggctg gcctacatcc aagagttgcg gaacggcagc  3960
aagaagcggc ggattaagca agattag                                      3987

SEQ ID NO: 21          moltype = DNA  length = 1592
FEATURE                Location/Qualifiers
source                 1..1592
                       mol_type = other DNA
                       organism = Medicago truncatula
SEQUENCE: 21
actgttaata atttttaaac gtcagcgcac taaaaaaacg aaaagacgga cacgtgaaaa  60
taaaaaacac acactagttt atgacgcaat actattttac ttatgatttg ggtacattag  120
acaaaaccgt gaaagagatg tatcagctat gaaacctgta tacttcaata cagagactta  180
ctcatatcgg atacgtacgc acgaagtatc atattaatta ttttaatttt taataaatat  240
tttatcggat acttatgtga tactctacat atacacaagg atatttctaa gatactttat  300
agatacgtat cctagaaaaa catgaagagt aaaaaaagtga gacaatgttg taaaaattca  360
ttataaatgt atatgattca attttagata tgcatcagta taattgattc tcgatgaaac  420
acttaaaatt atatttcttg tggaagaacg tagcgagaga ggtgattcag ttagacaaca  480
ttaaataaaa ttaatgttaa gttcttttaa tgatgtttct ctcaatatca catcatatga  540
aaatgtaata tgatttataa gaaaattttt aaaaaaattta ttttaataat cacatgtact  600
attttttaaa aattgtatct tttataataa tacaataata aagagtaatc agtgttaatt  660
tttcttcaaa tataagtttt attataaatc attgttaacg tatcataagt cattaccgta  720
tcgtatctta attttttttt aaaaaccgct aattcacgta cccgtattgt attgtacccg  780
cacctgtatc acaatcgatc ttagttagaa gaattgtctc gaggcggtgc aagacagcat  840
ataatagacg tggactctct tataccaaac gttgtcgtat cacaaagggt taggtaacaa  900
gtcacagttt gtccacgtgt cacgttttaa ttggaagagg tgccgttggc gtaatataac  960
agccaatcga tttttgctat aaaagcaaat caggtaaact aaacttcttc attcttttct  1020
tccccatcgc tacaaaaccg gttcctttgg aaaagagatt cattcaaacc tagcacccaa  1080
ttccgtttca aggtataatc tactttctat tcttcgatta ttttattatt attagctact  1140
atcgtttaat cgatcttttc ttttgatccg tcaaatttaa attcaattag ggtttttgttc  1200
ttttctttca tctgattgaa atccttctga attgaaccgt ttacttgatt ttactgttta  1260
ttgtatgatt taatcctttg tttttcaaag acagtcttta gattgtgatt aggggttcat  1320
ataaattttt agatttggat ttttgtattg tatgattcaa aaaatacgtc ctttaattag  1380
attagtacat ggatattttt tacccgattt attgattgtc agggagaatt tgatgagcaa  1440
gttttttga tgtctgttgt aaattgaatt gattataatt gctgatctgc tgcttccagt  1500
tttcataacc catattcttt taaccttgtt gtacacacaa tgaaaaattg gtgattgatt  1560
catttgtttt tctttgtttt ggattataca gg                                1592

SEQ ID NO: 22          moltype = DNA  length = 2000
FEATURE                Location/Qualifiers
source                 1..2000
                       mol_type = other DNA
                       organism = Zea mays
SEQUENCE: 22
gtcgtgcccc tctctagaga taaagagcat tgcatgtcta aagtataaaa aattaccaca  60
tatttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gtttttttttg caaatagctt gacctatata  300
atacttcatc cattttatta gtacatccat ttaggattta gggttgatgg tttctataga  360
ctaattttta gtacatccat tttattcttt ttagtctcta aattttttaa aactaaaact  420
ctattttagt tttttattta ataatttaga tataaaatga aataaaataa attgactaca  480
aataaaacaa ataccettta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacaccccct ccacaccctc tttccccaac ctcgtgttcg ttcggagcgc  900
acacacacgc aaccagatct cccccaaatc cagccgtcgg cacctccgct tcaaggtacg  960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
```

-continued

```
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc                                                2000

SEQ ID NO: 23           moltype = AA  length = 228
FEATURE                 Location/Qualifiers
source                  1..228
                        mol_type = protein
                        organism = Rattus norvegicus
SEQUENCE: 23
SSETGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLK                228

SEQ ID NO: 24           moltype = AA  length = 199
FEATURE                 Location/Qualifiers
source                  1..199
                        mol_type = protein
                        organism = Homo sapiens
SEQUENCE: 24
MEASPASGPR HLMDPHIFTS NFNNGIGRHK TYLCYEVERL DNGTSVKMDQ HRGFLHNQAK  60
NLLCGFYGRH AELRFLDLVP SLQLDPAQIY RVTWFISWSP CFSWGCAGEV RAFLQENTHV  120
RLRIFAARIY DYDPLYKEAL QMLRDAGAQV SIMTYDEFKH CWDTFVDHQG CPFQPWDGLD  180
EHSQALSGRL RAILQNQGN                                                 199

SEQ ID NO: 25           moltype = DNA  length = 621
FEATURE                 Location/Qualifiers
source                  1..621
                        mol_type = other DNA
                        organism = Petromyzon marinus
SEQUENCE: 25
acagatgcag agtatgtgag aattcacgaa aagctggaca tctatacctt caagaagcag  60
ttctttaaca ataagaagtc tgtgagccat aggtgctacg tgctgttcga gctgaagaga  120
aggggtgaaa gaagggcatg tttttggggg tatgctgtga acaagcccca gtctggaact  180
gagagaggca ttcacgccga aattttcagc atcagaaagg tggaggaata cctgagggat  240
aaccctggac agtttacaat taattggtat tctagctggt ctccatgcgc tgactgtgcc  300
gagaagatcc tggaatggta caaccaggag ctgagaggaa atggccatac cctgaagatt  360
tgggcctgca agctgtacta tgaaaagaac gcaagaaatc agatcggact gtggaacctg  420
agggataatg gtgtggggct gaacgtgatg gtgtccgagc actatcagtg ctgtagaaag  480
attttcattc agtcctcaca taatcagctg aacgagaata gatggctgga aaagactctg  540
aagagggctg agaagagaag gtccgaactg tcaattatga tccaggtgaa gatcctgcac  600
accactaagt cacctgccgt g                                              621

SEQ ID NO: 26           moltype = AA  length = 160
FEATURE                 Location/Qualifiers
source                  1..160
                        mol_type = protein
                        organism = synthetic construct
SEQUENCE: 26
FERNYDPREL RKETYLLYEI KWGKSGKLWR HWCQNNRTQH AEVYFLENIF NARRFNPSTH  60
CSITWYLSWS PCAECSQKIV DFLKEHPNVL EIYVARLYYH EDERNRQGLR DLVNSGVTIR  120
IMDLPDYNYC WKTFVSDQGG DEDYWPGHFA PWIKQYSLKL                          160

SEQ ID NO: 27           moltype = AA  length = 207
FEATURE                 Location/Qualifiers
source                  1..207
                        mol_type = protein
                        organism = synthetic construct
SEQUENCE: 27
TDAEYVRIHE KLDIYTFKKQ FSNNKKSVSH RCYVLFELKR RGERRACFWG YAVNKPQSGT  60
ERGIHAEIFS IRKVEEYLRD NPGQFTINWY SSWSPCADCA EKILEWYNQE LRGNGHTLKI  120
WVCKLYYEKN ARNQIGLWNL RDNGVGLNVM VSEHYQCCRK IFIQSSHNQL NENRWLEKTL  180
KRAEKRRSEL SIMFQVKILH TTKSPAV                                        207

SEQ ID NO: 28           moltype = AA  length = 228
FEATURE                 Location/Qualifiers
source                  1..228
                        mol_type = protein
                        organism = synthetic construct
SEQUENCE: 28
SSKTGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPNVT LFIYIARLYH  120
LANPRNRQGL RDLISSGVTI QIMTEQESGY CWHNFVNYSP SNESHWPRYP HLWVRLYVLE  180
LYCIILGLPP CLNILRRKQS QLTSFTIALQ SCHYQRLPPH ILWATGLK                228

SEQ ID NO: 29           moltype = AA  length = 162
FEATURE                 Location/Qualifiers
source                  1..162
```

```
                         mol_type = protein
                         organism = synthetic construct
SEQUENCE: 29
SFERNYDPRE LRKETYLLYE IKWGKSGKLW RHWCQNNRTQ HAEVYFLENI FNARRFNPST  60
HCSITWYLSW SPCAECSQKI VDFLKEHPNV NLEIYVARLY YPENERNRQG LRDLVNSGVT  120
IRIMDLPDYN YCWKTFVSDQ GGDEDYWPGH FAPWIKQYSL KL                    162

SEQ ID NO: 30            moltype = AA  length = 166
FEATURE                  Location/Qualifiers
source                   1..166
                         mol_type = protein
                         organism = Escherichia coli
SEQUENCE: 30
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTD                166

SEQ ID NO: 31            moltype = AA  length = 166
FEATURE                  Location/Qualifiers
source                   1..166
                         mol_type = protein
                         organism = synthetic construct
SEQUENCE: 31
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC AALLCYFFRM PRQVFNAQKK AQSSTD                166

SEQ ID NO: 32            moltype = AA  length = 166
FEATURE                  Location/Qualifiers
source                   1..166
                         mol_type = protein
                         organism = synthetic construct
SEQUENCE: 32
SEVEFSHEYW MRHALTLAKR AWDEREVPVG AVLVLNNRVI GEGWNRSIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC AALLCYFFRM RRQVFNAQKK AQSSTD                166

SEQ ID NO: 33            moltype = AA  length = 166
FEATURE                  Location/Qualifiers
source                   1..166
                         mol_type = protein
                         organism = synthetic construct
SEQUENCE: 33
SEVEFSHEYW MRHALTLAKR ALDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC NALLCYFFRM RRQVFNAQKK AQSSTD                166

SEQ ID NO: 34            moltype = AA  length = 166
FEATURE                  Location/Qualifiers
source                   1..166
                         mol_type = protein
                         organism = synthetic construct
SEQUENCE: 34
SEVEFSHEYW MRHALTLAKR ALDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC NALLCYFFRM PRQVFNAQKK AQSSTD                166

SEQ ID NO: 35            moltype = AA  length = 1763
FEATURE                  Location/Qualifiers
source                   1..1763
                         mol_type = protein
                         organism = synthetic construct
SEQUENCE: 35
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECAA LLCYFFRMPR QVFNAQKKAQ  360
SSTDSGGSSG GSSGSETPGT SESATPESSG GSSGGSDKKY SIGLAIGTNS VGWAVITDEY  420
KVPSKKFKVL GNTDRHSIKK NLIGALLFDS GETAEATRLK RTARRRYTRR KNRICYLQEI  480
FSNEMAKVDD SFFHRLEESF LVEEDKKHER HPIFGNIVDE VAYHEKYPTI YHLRKKLVDS  540
TDKADLRLIY LALAHMIKFR GHFLIEGDLN PDNSDVDKLF IQLVQTYNQL FEENPINASG  600
VDAKAILSAR LSKSRRLENL IAQLPGEKKN GLFGNLIALS LGLTPNFKSN FDLAEDAKLQ  660
LSKDTYDDDL DNLLAQIGDQ YADLFLAAKN LSDAILLSDI LRVNTEITKA PLSASMIKRY  720
DEHHQDLTLL KALVRQQLPE KYKEIFFDQS KNGYAGYIDG GASQEEFYKF IKPILEKMDG  780
TEELLVKLNR EDLLRKQRTF DNGSIPHQIH LGELHAILRR QEDFYPFLKD NREKIEKILT  840
FRIPYYVGPL ARGNSRFAWM TRKSEETITP WNFEEVVDKG ASAQSFIERM TNFDKNLPNE  900
KVLPKHSLLY EYFTVYNELT KVKYVTEGMR KPAFLSGEQK KAIVDLLFKT NRKVTVKQLK  960
```

-continued

```
EDYFKKIECF DSVEISGVED RFNASLGTYH DLLKIIKDKD FLDNEENEDI LEDIVLTLTL  1020
FEDREMIEER LKTYAHLFDD KVMKQLKRRR YTGWGRLSRK LINGIRDKQS GKTILDFLKS  1080
DGFANRNFMQ LIHDDSLTFK EDIQKAQVSG QGDSLHEHIA NLAGSPAIKK GILQTVKVVD  1140
ELVKVMGRHK PENIVIEMAR ENQTTQKGQK NSRERMKRIE EGIKELGSQI LKEHPVENTQ  1200
LQNEKLYLYY LQNGRDMYVD QELDINRLSD YDVDHIVPQS FLKDDSIDNK VLTRSDKNRG  1260
KSDNVPSEEV VKKMKNYWRQ LLNAKLITQR KFDNLTKAER GGLSELDKAG FIKRQLVETR  1320
QITKHVAQIL DSRMNTKYDE NDKLIREVKV ITLKSKLVSD FRKDFQFYKV REINNYHHAH  1380
DAYLNAVVGT ALIKKYPKLE SEFVYGDYKV YDVRKMIAKS EQEIGKATAK YFFYSNIMNF  1440
FKTEITLANG EIRKRPLIET NGETGEIVWD KGRDFATVRK VLSMPQVNIV KKTEVQTGGF  1500
SKESILPKRN SDKLIARKKD WDPKKYGGFD SPTVAYSVLV VAKVEKGKSK KLKSVKELLG  1560
ITIMERSSFE KNPIDFLEAK GYKEVKKDLI IKLPKYSLFE LENGRKRMLA SAGELQKGNE  1620
LALPSKYVNF LYLASHYEKL KGSPEDNEQK QLFVEQHKHY LDEIIEQISE FSKRVILADA  1680
NLDKVLSAYN KHRDKPIREQ AENIIHLFTL TNLGAPAAFK YFDTTIDRKR YTSTKEVLDA  1740
TLIHQSITGL YETRIDLSQL GGD                                         1763

SEQ ID NO: 36          moltype = AA  length = 1565
FEATURE                Location/Qualifiers
source                 1..1565
                       mol_type = protein
                       organism = synthetic construct
SEQUENCE: 36
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNSKR GAAGSLMNVL  120
NYPGMNHRVE ITEGILADEC AALLCDFYRM PRQVFNAQKK AQSSINSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                             1565

SEQ ID NO: 37          moltype = AA  length = 1565
FEATURE                Location/Qualifiers
source                 1..1565
                       mol_type = protein
                       organism = synthetic construct
SEQUENCE: 37
SEVEFSHEYW MRHALTLAKR ARDEREVPVG AVLVLNNRVI GEGWNRAIGL HDPTAHAEIM  60
ALRQGGLVMQ NYRLYDATLY STFEPCVMCA GAMIHSRIGR VVFGVRNAKT GAAGSLMDVL  120
HHPGMNHRVE ITEGILADEC AALLCRFFRM PRRVFNAQKK AQSSTDSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
```

-continued

```
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                              1565

SEQ ID NO: 38          moltype = AA  length = 364
FEATURE                Location/Qualifiers
source                 1..364
                       mol_type = protein
                       organism = synthetic construct
SEQUENCE: 38
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECAA LLCYFFRMPR QVFNAQKKAQ  360
SSTD                                                               364

SEQ ID NO: 39          moltype = AA  length = 167
FEATURE                Location/Qualifiers
source                 1..167
                       mol_type = protein
                       organism = synthetic construct
SEQUENCE: 39
MSEVEFSHEY WMRHALTLAK RARDEREVPV GAVLVLNNRV IGEGWNRAIG LHDPTAHAEI  60
MALRQGGLVM QNYRLYDATL YSTFEPCVMC AGAMIHSRIG RVVFGVRNAK TGAAGSLMDV  120
LHHPGMNHRV EITEGILADE CAALLCRFFR MPRRVFNAQK KAQSSTD                167

SEQ ID NO: 40          moltype = AA  length = 167
FEATURE                Location/Qualifiers
source                 1..167
                       mol_type = protein
                       organism = synthetic construct
SEQUENCE: 40
MSEVEFSHEY WMRHALTLAK RARDEREVPV GAVLVLNNRV IGEGWNRAIG LHDPTAHAEI  60
MALRQGGLVM QNYRLIDATL YVTFEPCVMC AGAMIHSRIG RVVFGVRNSK RGAAGSLMNV  120
LNYPGMNHRV EITEGILADE CAALLCDFYR MPRQVFNAQK KAQSSIN                167

SEQ ID NO: 41          moltype = AA  length = 83
FEATURE                Location/Qualifiers
source                 1..83
                       mol_type = protein
                       note = Bacillus phage AR9
                       organism = unidentified
SEQUENCE: 41
TNLSDIIEKE TGKQLVIQES ILMLPEEVEE VIGNKPESDI LVHTAYDEST DENVMLLTSD  60
APEYKPWALV IQDSNGENKI KML                                          83

SEQ ID NO: 42          moltype =   length =
SEQUENCE: 42
000

SEQ ID NO: 43          moltype =   length =
SEQUENCE: 43
000

SEQ ID NO: 44          moltype =   length =
SEQUENCE: 44
000

SEQ ID NO: 45          moltype = AA  length = 24
FEATURE                Location/Qualifiers
source                 1..24
                       mol_type = protein
                       organism = synthetic construct
SEQUENCE: 45
EELLSKNYHL ENEVARLKKG SGSG                                         24

SEQ ID NO: 46          moltype = AA  length = 241
FEATURE                Location/Qualifiers
source                 1..241
                       mol_type = protein
                       organism = synthetic construct
SEQUENCE: 46
EEELLSKNYH LENEVARLKK GSGSGEELLS KNYHLENEVA RLKKGSGSGE ELLSKNYHLE  60
NEVARLKKGS GSGEELLSKN YHLENEVARL KKGSGSGEEL LSKNYHLENE VARLKKGSGS  120
GEELLSKNYH LENEVARLKK GSGSGEELLS KNYHLENEVA RLKKGSGSGE ELLSKNYHLE  180
NEVARLKKGS GSGEELLSKN YHLENEVARL KKGSGSGEEL LSKNYHLENE VARLKKGSGS  240
G                                                                  241
```

```
SEQ ID NO: 47          moltype = AA  length = 277
FEATURE                Location/Qualifiers
source                 1..277
                       mol_type = protein
                       organism = synthetic construct
SEQUENCE: 47
MGPDIVMTQS PSSLSASVGD RVTITCRSST GAVTTSNYAS WVQEKPGKLF KGLIGGTNNR  60
APGVPSRFSG SLIGDKATLT ISSLQPEDFA TYFCALWYSN HWVFGQGTKV ELKRGGGGSG  120
GGGSGGGGSS GGGSEVKLLE SGGGLVQPGG SLKLSCAVSG FSLTDYGVNW VRQAPGRGLE  180
WIGVIWGDGI TDYNSALKDR FIISKDNGKN TVYLQMSKVR SDDTALYYCV TGLFDYWGQG  240
TLVTVSSYPY DVPDYAGGGG GSGGGGSGGG GSGGGGS                          277

SEQ ID NO: 48          moltype = DNA  length = 66
FEATURE                Location/Qualifiers
source                 1..66
                       mol_type = other DNA
                       organism = Saccharomyces bayanus
SEQUENCE: 48
ttcttgtcgt acttatagat cgctacgtta tttcaatttt gaaaatctga gtcctgggag  60
tgcgga                                                            66

SEQ ID NO: 49          moltype = AA  length = 605
FEATURE                Location/Qualifiers
source                 1..605
                       mol_type = protein
                       organism = Homo sapiens
SEQUENCE: 49
MSGWESYYKT EGDEEAEEEQ EENLEASGDY KYSGRDSLIF LVDASKAMFE SQSEDELTPF  60
DMSIQCIQSV YISKIISSDR DLLAWFYGTE KDKNSVNFKI YVLQELDNPG AKRILELDQF  120
KGQQGQKRFQ DMMGHGSDYS LSEVLWVCAN LFSDVQFKMS HKRIMLFTNE DNPHGNDSAK  180
ASRARTKAGD LRDTGIFLDL HLKKPGGFDI SLFYRDIISI AEDEDLRVHF EESSKLEDLL  240
RKVRAKETRK RALSRLKLKL NKDIVISVGI YNLVQKALKP PPIKLYRETN EPVKTKTRTF  300
NTSTGGLLLP SDTKRSQIYG SRQIILEKEE TEELKRFDDP GLMLMGFKPL VLLKKHHYLR  360
PSLFVYPEES LVIGSSTLFS ALLIKCLEKE VAALCRYTPR RNIPPYFVAL VPQEEELDDQ  420
KIQVTPPGFQ LVFLPFADDK RKMPFTEKIM ATPEQVGKMK AIVEKLRFTY RSDSFENPVL  480
QQHFRNLEAL ALDLMEPEQA VDLTLPKVEA MNKRLGSLVD EFKELVYPPD YNPEGKVTKR  540
KHDNEGSGSK RPKVEYSEEE LKTHISKGTL GKFTVPLKEA CRAYGLKSGL KKQELLEALT  600
KHFQD                                                             605

SEQ ID NO: 50          moltype = AA  length = 482
FEATURE                Location/Qualifiers
source                 1..482
                       mol_type = protein
                       organism = synthetic construct
SEQUENCE: 50
MVRSGNKAAW LCMDVGFTMS NSIPGIESPF EQAKKVITMF VQRQVFAENK DEIALVLFGT  60
DGTDNPLSGG DQYQNITVHR HLMLPDFDLL EDIESKIQPG SQQADFLDAL IVSMDVIQHE  120
TIGKKFEKRH IEIFTDLSSR FSKSQLDIII HSLKKCDISE RHSIHWPCRL TIGSNLSIRI  180
AAYKSILQER VKKTTWDAKT LKKEDIQKET VYCLNDDDET EVLKEDIIQG FRYGSDIVPF  240
SKVDEEQMKY KSEGKCFSVL GFCKSSQVQR RFFMGNQVLK VFAARDDEAA AVALSSLIHA  300
LDDLDIWAIV RYAYDKRANP QVGVAFPHIK HNYECLVYVQ LPFMEDLRQY MFSSLKNSKK  360
YAPTEAQLNA VDALIDSMSL AKKDEKTDTL EDLFPTTKIP NPRFQRLFQC LLHRALHPRE  420
PLPPIQQHIW NMLNPPAEVT TKSQIPLSKI KTLFPLIEAK KKDQVTAQEI FQDNHEDGPT  480
AK                                                                482

SEQ ID NO: 51          moltype = DNA  length = 10
FEATURE                Location/Qualifiers
source                 1..10
                       mol_type = other DNA
                       organism = Methanobacterium thermoautotrophicum
SEQUENCE: 51
aatttttgga                                                        10

SEQ ID NO: 52          moltype = AA  length = 83
FEATURE                Location/Qualifiers
source                 1..83
                       mol_type = protein
                       organism = Methanobacterium thermoautotrophicum
SEQUENCE: 52
GSVIDVSSQR VNVQRPLDAL GNSLNSPVII KLKGDREFRG VLKSFDLHMN LVLNDAEELE  60
DGEVTRRLGT VLIRGDNIVY ISP                                         83

SEQ ID NO: 53          moltype = DNA  length = 25
FEATURE                Location/Qualifiers
source                 1..25
                       isolate = Bacteriophage MS2
                       mol_type = other DNA
                       organism = Emesvirus zinderi
```

-continued

```
SEQUENCE: 53
gcgcacatga ggatcaccca tgtgc                                        25

SEQ ID NO: 54          moltype = AA  length = 116
FEATURE                Location/Qualifiers
source                 1..116
                       mol_type = protein
                       note = Bacteriophage MS2
                       organism = Emesvirus zinderi
SEQUENCE: 54
MASNFTQFVL VDNGGTGDVT VAPSNFANGI AEISSNSRSQ AYKVTCSVRQ SSAQNRKYTI  60
KVEVPKGAWR SYLNMELTIP IFATNSDCEL IVKAMQGLLK DGNPIPSAIA ANSGIY      116

SEQ ID NO: 55          moltype = DNA  length = 26
FEATURE                Location/Qualifiers
source                 1..26
                       isolate = Bacteriophage PP7
                       mol_type = other DNA
                       organism = Pepevirus rubrum
SEQUENCE: 55
ataaggagtt tatatggaaa ccctta                                       26

SEQ ID NO: 56          moltype = AA  length = 127
FEATURE                Location/Qualifiers
source                 1..127
                       mol_type = protein
                       note = Bacteriophage PP7
                       organism = Pepevirus rubrum
SEQUENCE: 56
MSKTIVLSVG EATRTLTEIQ STADRQIFEE KVGPLVGRLR LTASLRQNGA KTAYRVNLKL  60
DQADWDCSTS VCGELPKVRY TQVWSHDVTI VANSTEASRK SLYDLTKSLV ATSQVEDLVV  120
NLVPLGR                                                            127

SEQ ID NO: 57          moltype = DNA  length = 19
FEATURE                Location/Qualifiers
misc_feature           1..19
                       note = Shigella phage
source                 1..19
                       mol_type = other DNA
                       organism = unidentified
SEQUENCE: 57
ctgaatgcct gcgagcatc                                               19

SEQ ID NO: 58          moltype = AA  length = 62
FEATURE                Location/Qualifiers
REGION                 1..62
                       note = Shigella phage
source                 1..62
                       mol_type = protein
                       organism = unidentified
SEQUENCE: 58
MKSIRCKNCN KLLFKADSFD HIEIRCPRCK RHIIMLNACE HPTEKHCGKR EKITHSDETV  60
RY                                                                 62

SEQ ID NO: 59          moltype = AA  length = 1367
FEATURE                Location/Qualifiers
source                 1..1367
                       mol_type = protein
                       organism = synthetic construct
SEQUENCE: 59
DKKYSIGLAI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM  1020
IAKSEQEIGK ATAKYFFYSN IMNFFKTEIT LANGEIRKRP LIETNGETGE IVWDKGRDFA  1080
TVRKVLSMPQ VNIVKKTEVQ TGGFSKESIL PKRNSDKLIA RKKDWDPKKY GGFDSPTVAY  1140
```

-continued

```
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD                1367

SEQ ID NO: 60          moltype = AA  length = 1367
FEATURE                Location/Qualifiers
source                 1..1367
                       mol_type = protein
                       organism = synthetic construct
SEQUENCE: 60
DKKYSIGLAI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLADDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PALESEFVYG DYKVYDVRKM  1020
IAKSEQEIGK ATAKYFFYSN IMNFFKTEIT LANGEIRKAP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD                1367

SEQ ID NO: 61          moltype = DNA  length = 4101
FEATURE                Location/Qualifiers
source                 1..4101
                       mol_type = other DNA
                       organism = synthetic construct
SEQUENCE: 61
gacaagaagt acagcatcgg gctggcgatc gggaccaact ccgtcggctg ggctgtgatt  60
accgacgagt acaaggtgcc atccaagaag ttcaaggtcc tcggcaacac tgaccggcac  120
agcattaaga agaacctgat tggggcgctg ctgttcgatt cgggggagac tgcggaggcg  180
accaggctga agcggactgc gcgccggagg tacaccagga ggaagaatcg gatctgctac  240
ctccaggaga ttttctcgaa tgagatggcc aaggtggacg attccttctt ccatcgcctg  300
gaggagtcgt tcctcgttga ggaggacaag aagcatgaga ggcatcccat tttcgggaat  360
atcgttgacg aggtggctta ccatgagaag tacccgacca tctaccatct gcggaagaag  420
ctcgtcgatt cgaccgataa ggccgacctg cggctgatct acctggccct cgcgcacatg  480
attaagttcc ggggccattt cctcatcgag ggcgacctca acccggacaa ctcggacgtg  540
gataagctct tcattcagct cgtgcagaca tacaaccagc tcttcgagga gaatcccatt  600
aacgcctcgg gggtcgacgc taaggctatt ctctcggctc ggctgtcgaa gtcgcgccgg  660
ctggagaatc tcattgccca gctcccaggc gagaagaaga acggcctctt cggcaacctg  720
attgccctgt cgctggggct cacaccgaat ttcaagtcga acttcgacct cgccgaggac  780
gctaagctcc agctcagcaa ggatacttac gatgatgacc tcgataacct gctcgcccag  840
attggggatc agtacgcgga tctgttcctc gcggccaaga atctcagcga tgctattctc  900
ctgtcggaca ttctccgcgt caacacagag attactaagg ccccactgtc ggcgagcatg  960
attaagaggt acgatgagca tcatcaggac ctgacactgc tcaaggcgct ggtccggcag  1020
cagctccccg agaagtacaa ggagattttc ttcgatcagt caaagaatgg gtacgcgggc  1080
tacattgatg gcggcgcgtc ccaggaggag ttctacaagt tcattaagcc catcctggag  1140
aagatggacg ggaccgagga gctgctggtg aagctcaatc gggaggacct gctccggaag  1200
cagcgcacat tcgacaatgg ctcgattcct caccagattc acctgggcga gctgcacgcc  1260
attctccgca ggcaggagga cttctacccg ttcctcaagg acaaccgcga gaagatcgag  1320
aagatcctga ccttccggat tccatactac gtggggccgc tcgcgcgggg gaactcccgg  1380
ttcgcgtgga tgactcgcaa gtccgaagaa acgattacac cgtggaattt cgaggaggtc  1440
gtcgacaagg gcgctagtgc gcagtcattc attgagagga tgaccaattt cgataagaac  1500
ctgcctaacg agaaggtgct gccgaagcat tcgctgctct acgagtactt caccgtttac  1560
aatgagctga ccaaggtgaa gtatgtgact gagggcatga ggaagccagc gttcctgagc  1620
ggcgagcaga agaaggctat cgtggacctg ctcttcaaga ctaaccggaa ggtgactgtg  1680
aagcagctca aggaggacta cttcaagaag attgagtgct tcgattccgt tgagattagc  1740
ggggtggagg atcggttcaa tgcttcgctc gggacatacc acgatctcct gaagatcatt  1800
aaggataagg acttcctcga caacgaggag aacgaggaca ttctcgaaga tattgtcctg  1860
accctcaccc tcttcgagga tcgggagatg atcgaggaga ggctcaagac atacgctcat  1920
ctgttcgatg ataaggtcat gaagcagctg aagcgcaggc ggtacacagg gtgggggcgg  1980
ctgagccgga agctgatcaa cgggattcgg gataagcagt ccgggaagac aattctcgac  2040
ttcctcaagt ccgacgggtt cgctaaccgg aacttcatgc agctcattca tgatgactcg  2100
ctgacattca aggaggatat tcagaaggcg caggtttcgg ggcagggcga ctcgctccac  2160
gagcatattg cgaatctggc gggctccccc gcgattaaga agggcattct gcaaaccgtc  2220
aaggtggttg atgagctggt caaggtcatg ggcggcata agccagagaa tattgtcatc  2280
```

-continued

```
gagatggcgc gggagaatca gaccacacag aaggggcaga agaactcacg ggagcggatg  2340
aagcgcatcg aggagggcat caaggagctg gggtcgcaga tcctgaagga gcatcccgtg  2400
gagaacactc agctgcaaaa tgagaagctg tacctctact acctccagaa cgggagggac  2460
atgtatgtgg atcaggagct ggatattaat aggctgagcg attacgatgt cgaccacatt  2520
gtcccacagt cgttcctgaa ggacgacagc attgacaaca aggtgctgac ccgctcggat  2580
aagaacaggg gcaagagcga taatgttcca agcgaggagg ttgtgaagaa gatgaagaac  2640
tactggcggc agctcctgaa cgcgaagctc atcacacagc ggaagttcga caacctcacc  2700
aaggctgagc gcgggggcct gagcgagctg gacaaggcgg ggttcattaa gaggcagctg  2760
gtcgagacac ggcagattac aaagcatgtt gcgcagattc tcgattcccg gatgaacacc  2820
aagtacgatg agaacgataa gctgattcgg gaggtcaagg taattaccct gaagtccaag  2880
ctggtgtccg acttcaggaa ggacttccag ttctacaagg ttcgggagat caacaactac  2940
caccacgcgc atgatgccta cctcaacgcg gtcgtgggga ccgctctcat caagaagtac  3000
ccaaagctgg agtcagagtt cgtctacggg gattacaagg tttacgacgt gcggaagatg  3060
atcgctaaga gcgagcagga gattggcaag gctaccgcta agtacttctt ctactccaac  3120
atcatgaact tcttcaagac agagattacc ctcgcgaatg gcgagatccg gaagaggccc  3180
ctcatcgaga caaatgggga gacaggggag attgtctggg ataaggggcg ggatttcgcg  3240
accgtccgga aggtcctgtc gatgccccag gttaatattg tcaagaagac tgaggtccag  3300
actggcggct tctcaaagga gtcgattctc ccaaagagga actccgataa gctcattgct  3360
cggaagaagg attgggaccc caagaagtac gggggattcg actcccccac tgttgcttac  3420
tctgttctgg ttgttgctaa ggtggagaag gggaagtcga agaagctgaa gagcgtgaag  3480
gagctgctcg ggattacaat tatggagagg tcatccttcg agaagaatcc catcgacttc  3540
ctggaggcca agggctacaa ggaggtgaag aaggacctga ttattaagct gcccaagtac  3600
tcgctcttcg agctggagaa tgggcggaag cggatgctgg cgtccgcggg ggagctgcaa  3660
aaggggaacg agctggcgct cccctccaag tatgtgaact tcctctacct ggcgtcgcac  3720
tacgagaagc tgaaggggtc cccagaggat aatgagcaga agcagctctt cgtcgagcag  3780
cataagcact acctggacga gattatcgag cagattagcg agttctcgaa gcgggtcatc  3840
ctcgcggatg cgaacctgga taaggtgctc agcgcctaca ataagcaccg ggacaagccg  3900
attcgggagc aggcggagaa tattattcac ctcttcacac tcaccaacct cggggcacca  3960
gctgcgttca agtacttcga cactactatc gaccggaagc ggtacacctc gacgaaggag  4020
gtgctcgacg ccaccctcat tcaccagtcg atcacaggcc tgtacgagac acggattgac  4080
ctgtcccagc tcgggggcga c                                           4101

SEQ ID NO: 62          moltype = DNA  length = 4101
FEATURE                Location/Qualifiers
source                 1..4101
                       mol_type = other DNA
                       organism = synthetic construct
SEQUENCE: 62
gacaagaagt actccattgg cctggcgatt gggacaaact cggtggggtg ggccgtgatt  60
acggatgagt acaaggttcc aagcaagaag ttcaaggtcc tcgggaacac agatcggcat  120
tcgattaaga agaatctcat tggggcgctc ctcttcgact cgggggagac agcggaggct  180
accaggctca agcggacagc caggcggcgg tacacaaggc ggaagaatcg catctgctac  240
ctccaggaga ttttctcgaa tgagatggcg aaggtggacg acagcttctt ccatcggctg  300
gaggagtcct tcctggtgga ggaggataag aagcacgaga ggcatccaat tttcgggaac  360
atcgtggacg aggttgcgta ccatgagaag taccctacaa tctaccatct gcggaagaag  420
ctggttgact ccacagacaa ggcggacctg aggctgatct acctcgctct ggcccacatg  480
attaagttcc gcgggcattt cctgatcgag ggggacctga atcccgacaa ttcggatgtg  540
gacaagctct tcatccagct ggtgcagacc tacaaccagc tgttcgagga gaatcccatc  600
aatgcgtcgg gcgttgacgc taaggccatt ctgtccgcta ggctgtcgaa gagcaggagg  660
ctggagaacc tgatcgccca gctgccaggc gagaagaaga atgggctctt cgggaatctg  720
attgcgctct ccctggggct gacaccgaac ttcaagagca atttcgatct ggctgaggac  780
gcgaagctcc agctctcgaa ggacacttac gacgatgacc tcgataacct cctcgcgcag  840
atcggggacc agtacgctga tctcttcctc gccgctaaga acctctcgga tgctatcctg  900
ctctccgaca ttctccgggt taataccgag attacaaagg ccccactgtc ggcgtccatg  960
atcaagcggt acgatgagca tcatcaggat ctcaccctgc tcaaggccct cgtgcggcag  1020
cagctgcccg agaagtacaa ggagattttc ttcgaccaga gcaagaatgg gtacgctggc  1080
tacattgacg gcggggcctc acaggaggag ttctacaagt tcatcaagcc aatcctggag  1140
aagatggatg ggacagagga gctgctggtg aagctcaacc gggaggatct gctcaggaag  1200
cagcggacgt tcgacaacgg gtcgattccc catcagatcc acctgggggga gctgcacgcg  1260
atcctgcgcc ggcaggagga tttctaccct ttcctgaagg ataatcggga gaagatcgag  1320
aagattctca ccttccggat tccctactac gtcgggccac tcgcgcgggg caatagcagg  1380
ttcgcctgga tgacacggaa gagcgaggag acaatcaccc cctggaactt cgaggaggtt  1440
gtcgacaagg gggcgtccgc ccagtcattc attgagcgga tgaccaattt cgacaagaat  1500
ctgccaaatg agaaggttct cccaaagcat agcctcctct acgagtactt cactgtttac  1560
aacgagctga ccaaggtgaa gtatgtgacc gagggcatgc ggaagcccgc gttcctgtcc  1620
ggcgagcaga agaaggccat tgtggacctc ctgttcaaga ccaatcgcaa ggtcacagtc  1680
aagcagctca aggaggatta cttcaagaag atcgagtgct tcgactcggt tgagattagc  1740
ggggtggagg atcggttcaa cgcgagcctc ggcacttacc acgacctcct gaagatcatc  1800
aaggataagg acttcctcga caacgaggag aacgaggata ttctggagga catcgtgctc  1860
accctgacgc tgttcgagga tcgggagatg atcgaggagc gcctgaagac ctacgctcat  1920
ctcttcgatg ataaggtcat gaagcagctg aagaggaggc ggtacaccgg gtggggccgc  1980
ctgagcagga agctcattaa cggggatcagg gacaagcaga gcggcaagac catcctggac  2040
ttcctcaaga gcgatggctt cgccaaccgg aatttcatgc agctcatcca cgacgactcc  2100
ctcaccttca aggaggacat tcagaaggct caggtcagcg gccagggcga ctcgctgcat  2160
gagcacatcg ctaacctggc gggcagccca gccatcaaga agggcatcct ccagacagtg  2220
aaggtcgtgg atgagctggt gaaggtcatg ggccggcata agcccgagaa tattgtgatt  2280
gagatggcgc gggagaatca gaccactcag aagggccaga agaactcgcg ggagcgcatg  2340
aagaggatcg aggaggggat taaggagctg ggcagccaga ttctcaagga gcaccccgtg  2400
gagaataccc agctccagaa cgagaagctg tacctctact acctccagaa tgggcgggac  2460
```

```
atgtatgttg atcaggagct ggacatcaat cgcctctcgg attacgacgt ggaccacatc  2520
gtgccccaga gcttcctgaa ggatgatagc atcgacaata aggtcctgac ccgctccgac  2580
aagaatcgcg gcaagagcga caacgtgccg agcgaggagg tcgtgaagaa gatgaagaac  2640
tactggcggc agctgctgaa cgcgaagctc attacacagc ggaagttcga taacctgacg  2700
aaggcggaga ggggcggcct ctccgagctg gacaaggcgg gcttcattaa gaggcagctc  2760
gtggagactc gccagatcac caagcacgtg gctcagatcc tcgatagccg gatgaatacg  2820
aagtacgatg agaatgacaa gctcatccgg gaggtgaagg taatcaccct gaagtcaaag  2880
ctcgttagcg atttccggaa ggacttccag ttctacaagg tgcgggagat taacaactac  2940
catcatgcgc acgatgcgta cctcaatgcg gtggtgggca cagccctgat taagaagtac  3000
cccaagctgg agagcgagtt cgtctacggg gactacaagg tgtacgatgt tcggaagatg  3060
atcgccaaga gcgagcagga gattgggaag gccaccgcta agtacttctt ctactcgaat  3120
attatgaatt tcttcaagac cgagatcaca ctcgctaatg gggagattcg gaagcggccc  3180
ctcatcgaga ctaacgggga gactggcgag attgtgtggg acaaggggcg cgacttcgct  3240
accgtgcgca aggtcctctc gatgccccag gttaatattg ttaagaagac agaggtgcag  3300
acgggcgggt tctccaagga gtctatcctg ccgaagcgga actcggacaa gctgatcgcc  3360
cgcaagaagg attgggaccc caagaagtac gggggattcg atagcccaac cgtggcttac  3420
agcgtcctgg tggtcgccaa ggttgagaag gggaagtcga agaagctcaa gagcgttaag  3480
gagctgctgg gcatcaccat catggagcgg tccagcttcg agaagaatcc tatcgacttc  3540
ctggaggcta aggggtacaa ggaggtcaag aaggacctga tcattaagct gcccaagtac  3600
tctctgttcg agctggagaa cgggaggaag cggatgctgg cgtctgctgg cgagctacag  3660
aagggcaatg agctggcgct cccctcgaag tatgtcaact tcctctacct ggcttcccat  3720
tacgagaagc tgaagggctc gcccgaggat aatgagcaga agcagctctt cgtggagcag  3780
cacaagcact acctcgacga gatcattgag cagatttcgg agttctcgaa gcgggtcatt  3840
ctcgcggacg cgaacctcga caaggtcctc tcggcgtaca acaagcaccg ggacaagccc  3900
atccgggagc aggccgagaa cattatccac ctcttcacac tgaccaacct cggcgctccc  3960
gccgcgttca agtacttcga caccaccatt gaccgcaaga gatacacatc caccaaggag  4020
gtgctggacg cgaccctcat ccaccagagc atcacaggcc tctacgagac acggatcgac  4080
ctctcgcagc tcgggggcga t                                            4101

SEQ ID NO: 63          moltype = DNA  length = 4092
FEATURE                Location/Qualifiers
source                 1..4092
                       mol_type = other DNA
                       organism = synthetic construct
SEQUENCE: 63
gacaagaagt actcgatcgg cctggcgatt ggcacaaaca gcgtggggtg ggctgtgatc  60
actgatgagt acaaggtgcc atcgaagaag ttcaaggtgc tggggaatac agaccggcat  120
tcgatcaaga agaatctcat tggcgctctc ctcttcgatt ccggcgagac tgctgaggcg  180
acccgcctga agcgcaccgc ccggcggcgc tacactcggc ggaagaatag gatttgctac  240
ctccaggaga ttttctcgaa tgagatggcc aaggtggatg acagcttctt ccaccgcctg  300
gaggagtcgt tcctggtcga ggaggacaag aagcatgagc ggcaccctat cttcgggaat  360
atcgttgatg aggtcgccta ccacgagaag taccccacta tctaccatct ccgcaagaag  420
ctcgtggaca gcacagataa ggccgacctc cgcctgatct acctcgccct cgcgcacatg  480
attaagttcc gggggcactt cctcattgag gggatctga atcccgataa ctccgacgtg  540
gacaagctgt tcatccagct ggtgcagaca tacaaccagc tgttcgagga gaatcccatc  600
aacgcgagcg gcgtggacgc taaggccatt ctgtcggcta ggctctcgaa gtcgaggcgg  660
ctggagaacc tgattgcgca gctccccggc gagaagaaga acgggctgtt cgggaatctc  720
atcgccctct ccctcggcct cacaccaaac ttcaagagca atttcgacct ggctgaggac  780
gctaagctgc aactctcaaa ggatacatac gatgacgacc tggacaatct cctggctcag  840
atcggcgacc agtacgctga cctgttcctc gcggccaaga atctgtcgga cgcgattctc  900
ctcagcgaca tcctgcgcgt caataccgag attacgaagg ctccactgtc tgcgtcaatg  960
attaagcggt acgatgagca tcaccaggat ctgaccctcc tgaaggcgct cgtgcggcag  1020
cagctgcccg agaagtacaa ggagattttc ttcgatcaga gcaagaatgg ctacgccggc  1080
tacatcgacg gggcgcgag ccaggaggag ttctacaagt tcatcaagcc catcctggag  1140
aagatggacg gcaccgagga gctactcgtg aagctcaatc gggaggatct cctccggaag  1200
cagcggacat tcgataacgg gtctatccca caccagatcc acctcggcga gctgcatgcg  1260
attctgcggc ggcaggagga tttctaccct ttcctgaagg acaaccggga gaagatcgag  1320
aagatcctca cattccggat tccatactac gtcggccccc tggcgagggg caatagccgg  1380
ttcgcgtgga tgacaaggaa gtccgaggag actattaccc cgtggaattt cgaggaggtg  1440
gttgacaagg gcgcttccgc gcagagcttc attgagcgga tgacaaactt cgacaagaat  1500
ctccccaacg agaaggtcct gccgaagcat agcctcctgt acgagtactt caccgtctac  1560
aatgagctaa ctaaggtcaa gtatgtgaca gagggcatga ggaagccagc cttcctctca  1620
ggcgagcaga agaaggccat tgtggacctc ctgttcaaga caaaccgcaa ggtgacagtg  1680
aagcagctga aggaggatta cttcaagaag attgagtgct tcgactcagt ggagatttca  1740
ggcgtggagg atcggttcaa cgcgagcctg gggacttacc acgacctgct gaagattatt  1800
aaggacaagg acttcctgga taacgaggag aatgaggaca tcctggagga tattgtgctc  1860
accctcaccc tgttcgagga cagggagatg attgaggaga ggctcaagac ctacgcgcac  1920
ctgttcgatg acaaggtcat gaagcagctg aagaggcggc gctacactgg gtggggccgc  1980
ctgtcgcgga agctgatcaa cggcattcgg gataagcagt ccgggaagac cattctggat  2040
ttcctgaagt cggacggctt cgccaacagg aatttcatgc agctgatcca cgacgactcc  2100
ctcaccttca aggaggacat tcagaaggcc caggttagcg gccaggggga ctcactccac  2160
gagcatattg ccaatctggc cggctctcca gctatcaaga agggcatcct gcaaacagtt  2220
aaggttgttg acgagctggt taaggtcatg gggcggcata agcccgagaa cattgtcatc  2280
gagatggctc gggagaacca gacaactcag aagggccaga agaactccag ggagcgcatg  2340
aagcggattg aggagggcat taaggagctg gggtcccaga tcctcaagga gcaccctgtc  2400
gagaacactc agctgcaaaa cgagaagctc tacctgtact acctccagaa cgggcgggat  2460
atgtatgtgg atcaggagct ggacatcaac aggctctccg actacgacgt ggatcacatt  2520
gtcccacagt ctttcctcaa ggatgattcc atcgacaaca aggtgctgac gcgcagcgac  2580
aagaataggg ggaagtcgga caacgttccg agcgaggagg tcgtgaagaa gatgaagaat  2640
```

```
tactggaggc agctcctgaa tgcgaagctg atcactcaga ggaagttcga caatctgaca  2700
aaggcggaga ggggcgggct ctcggagctg gataaggcgg gcttcatcaa gcggcagctc  2760
gttgaaaccc ggcagatcac caagcatgtc gcccagatcc tcgatagccg catgaacacc  2820
aagtacgatg agaacgacaa gctcattcgg gaggttaagg tcattacgct gaagtccaag  2880
ctcgtcagcg acttcaggaa ggatttccag ttctacaagg ttcgggagat taacaactac  2940
caccacgcgc atgatgcgta cctgaacgct gttgtcggca ctgctctcat caagaagtac  3000
ccaaagctgg agtccgagtt cgtctacggg gactacaagg tctacgatgt ccggaagatg  3060
atcgccaagt cggagcagga gatcgggaag gctactgcga agtacttctt ctacagcaac  3120
attatgaatt tcttcaagac ggagattacg ctggcgaacg gggagattag gaagaggccc  3180
ctcattgaga ctaatgggga gacaggcgag attgtttggg acaagggccg cgacttcgcg  3240
actgtgcgga aggtcctgtc catgccacag gtgaatattg ttaagaagac agaggtgcag  3300
actgggggct tctcgaagga gagcattctc ccaaagcgga acagcgataa gctcatcgcg  3360
cgcaagaagg attgggaccc taagaagtac ggcggcttcg attctcccac tgtggcctac  3420
tccgttctcg tggttgccaa ggttgagaag gggaagtcga agaagctgaa gtcggtcaag  3480
gagctgctcg ggattacaat catggagcgg agcagcttcg agaagaaccc tattgatttc  3540
ctggaggcca agggctacaa ggaggttaag aaggatctca ttatcaagct ccctaagtac  3600
tctctgttcg agctggagaa tggccggaag aggatgctgg cctcggctgg cgagctacag  3660
aaggggaatg agctggccct cccgtcgaag tatgtgaatt tcctgtacct cgcgtcgcac  3720
tacgagaagc tcaagggcag cccggaggat aatgagcaga agcagctctt cgtggagcag  3780
cataagcact acctggacga gatcattgag cagatcagcg agttctcgaa gcgggttatt  3840
ctggctgatg ctaacctgga caaggttctg agcgcctaca ataagcatcg cgacaagccg  3900
attcgcgagc aggcggagaa tattatccac ctgttcaccc tcactaacct cggggctccc  3960
gcggccttca agtacttcga taccacaata gataggaagc ggtacacctc gacgaaggag  4020
gtcctcgacg ccacactcat ccatcagtcg attacaggcc tgtacgagac acggattgac  4080
ctctcgcagc tg                                                       4092

SEQ ID NO: 64          moltype = DNA  length = 4101
FEATURE                Location/Qualifiers
source                 1..4101
                       mol_type = other DNA
                       organism = synthetic construct
SEQUENCE: 64
gacaagaagt attccatagg cctggctatc ggcaccaaca gcgtgggctg ggccgtcatc  60
accgacgagt acaaagtgcc gagtaaaaag ttcaaagtgc tcggcaacac cgaccgccac  120
tccataaaga aaaacctgat cggggcgctc ctgttcgaca gcggcgagac ggcggaggcc  180
acccgcttga aacgcacggc ccgacggcgc tacacgcggc gcaagaaccg gatctgttac  240
ctacaggaga ttttctctaa cgagatggcg aaggtggacg actcgttctt tcaccgcctc  300
gaagagtcct tcctcgtgga ggaggacaag aaacacgagc gccacccgat cttcggcaac  360
atcgtggacg aggtggccta ccacgagaag tacccgacca tctaccacct ccggaagaaa  420
ctcgtggaca gcacggacaa ggccgacctg aggctcatct acctcgccct ggcgcacatg  480
attaagttcc ggggccactt cctgatcgag ggcgacctga acccggacaa cagcgacgtg  540
gacaagctgt tcatccagct agtccagacc tacaaccagc ttttcgagga aaaccccatc  600
aacgccagcg gggtggacgc gaaggcgatc ctgtccgccc ggctgagcaa gtcccggcgg  660
ctggagaacc tcatcgcgca gttgcccggc gagaagaaga acgggctgtt cgggaacctg  720
atcgccctct ccctggggct caccccgaac ttcaagtcca acttcgacct cgccgaggac  780
gccaaactac agctgagcaa ggacacctac gacgacgacc tcgacaacct gctggcccag  840
atcggggacc agtacgcaga cctgttcctc gccgccaaga acctctccga cgccatcctg  900
ctgtcggaca tcctgcgggt gaacacggag atcacgaagg ccccgctctc ggcctcgatg  960
attaaacgct acgacgagca ccaccaggac ttgaccctcc tcaaggcgct ggtccgccag  1020
cagcttcccg agaagtacaa ggaaatcttt ttcgatcaga gcaagaacgg gtacgccggg  1080
tacatcgacg gcggggcgtc ccaggaggag ttctacaagt tcatcaagcc catcctggag  1140
aaaatggacg ggaccgagga gctgctcgtg aagctcaacc gcgaagattt gctccgcaag  1200
cagcgcacgt tcgacaacgg gtcgatcccg caccagatcc acctgggcga gctgcacgcg  1260
atcctcaggc gtcaggaaga cttctacccc ttcctcaagg acaaccgcga gaagatagag  1320
aagattctga ccttcagaat tccttattac gtgggcccgc tggctcgggg caactcgcgc  1380
ttcgcctgga tgacgcgcaa gtccgaggag accatcaccc cgtggaactt cgaggaggtg  1440
gtggataagg gtgcctcggc ccagtccttc atcgagcgga tgaccaactt cgacaagaac  1500
ctgccgaacg agaaggtgct ccccaagcac agcctgctct acgaatattt cacggtgtac  1560
aacgagctga cgaaggtcaa gtacgtgacc gagggaatga ggaaacctgc attcctctcc  1620
ggggagcaga agaaagccat agtcgacctc ctgttcaaga ccaaccggaa ggtcaccgtc  1680
aagcagctca aggaggacta cttcaagaag atcgagtgct tcgattcagt ggagatcagc  1740
ggcgtcgagg accggttcaa cgccagcctg ggcacctacc acgacctgct caagatcatc  1800
aaggacaagg acttcctcga caacgaggag aacgaggaca tcctggagga catcgtgctg  1860
accctgacgc tcttcgagga ccgcgagatg atcgaggagc gcctcaagac ctacgcccac  1920
ctgttcgacg acaaggtgat gaagcagctc aagcggcgga gatatactgg gtggggccgc  1980
ctctcccgga agctcattaa cggtatcagg gataagcagt ccgggaagac gatcctcgac  2040
ttcctcaagt cggacgggtt cgccaaccgc aacttcatgc agctcatcca cgacgactcc  2100
ctgacgttca aggaggacat ccagaaggcc caagtgtctg gtcaaggtga ctcgctccac  2160
gagcacatcg ccaacctcgc gggcagcccg gccatcaaga agggaatact ccagaccgtc  2220
aaggtggtgg acgagctggt gaaggtcatg ggccgccaca agccggagaa catcgtcatc  2280
gagatggcgc gggagaacca gaccacgcag aaggggcaga aaaatagccg tgagcgcatg  2340
aagcgcatcg aggaggggat taaggagttg ggcagccaga tcctcaagga gcaccctgtg  2400
gagaacacgc agttgcaaaa cgagaagctc tacctgtact acctccagaa cgggagggat  2460
atgtacgtgg accaagaact ggacatcaac cgcctgtccg actacgacgt ggaccacatc  2520
gtgccgcaga gcttcctcaa ggacgacagc atcgacaaca aggtgctcac ccggtccgac  2580
aagaatcggg gcaagtccga caacgtgccc agcgaggagg tcgtcaaaaa gatgaaaaac  2640
tactggcgac aactactgaa cgccaagctc atcacccagc gcaagttcga caacctcaca  2700
aaagccgagc gcggcgggtt gagcgagctg gacaaggccg ggttcatcaa gcgccagctc  2760
gtcgagacgc gccagatcac gaagcacgtc gcgcagatac tcgacagccg gatgaacacc  2820
```

-continued

```
aagtacgacg agaacgacaa gctcatccgg gaggtgaagg tcatcaccct caagtcgaag  2880
ctcgtgagcg acttccgcaa ggacttccag ttctacaagg tccgggagat caacaactac  2940
caccacgccc acgatgctta tcttaacgcc gtggtgggga cggccctcat taagaaatac  3000
ccgaagctgg agtcggagtt cgtgtacggc gactacaagg tgtacgacgt caggaagatg  3060
atcgccaagt ccgaacagga gatcgggaag gccacggcga aatacttctt ctacagcaac  3120
atcatgaact tcttcaagac cgagatcacc ctcgccaacg gcgagatccg caagcgcccg  3180
ctcatcgaga cgaacgggga gaccggcgag atcgtctggg acaaggggcg cgacttcgcc  3240
actgtgcgga aggtgctgtc gatgccccag gtcaacatcg tcaagaagac ggaggtccag  3300
acgggcgggt tcagcaagga gagcatcctg ccgaagcgca acagcgacaa gctgatcgcc  3360
cgcaaaaagg actgggatcc aaaaaagtac ggcggcttcg acagccccac cgtcgcctac  3420
agcgtcctcg tcgtcgctaa agtcgagaag ggcaagtcca aaaagctcaa gagcgtcaag  3480
gagctgctcg ggatcaccat catggagcgg tccagcttcg agaagaaccc aattgatttc  3540
ctggaggcga agggctacaa ggaggtcaag aaagacctca tcataaagct gccgaagtac  3600
tcactcttcg agctggagaa cgggcgcaag cggatgctgg cgtcggccgg agagctccaa  3660
aagggcaacg agctggcgct gccgagcaag tacgtgaact tcctctacct ggcgtcccac  3720
tacgagaagc tcaagggcag tccagaggat aacgagcaga agcagctatt cgtggagcag  3780
cacaagcact acctggacga gatcatcgag cagatcagcg agttctccaa gcgcgtcatc  3840
ctggcggacg ccaacctgga caaggtgctg tccgcgtaca acaagcaccg cgacaagccg  3900
atccgcgagc aagccgagaa catcatccac ctgttcaccc tcacgaacct cggggcaccc  3960
gccgccttca aatatttcga cacgaccatc gaccgcaagc gctacaccag cacgaaggag  4020
gtgctcgacg ccaccctgat ccaccagagc atcaccgggc tgtacgagac ccgcatcgac  4080
ctctcgcagc tcggcgggga c                                            4101

SEQ ID NO: 65          moltype = DNA  length = 4101
FEATURE                Location/Qualifiers
source                 1..4101
                       mol_type = other DNA
                       organism = synthetic construct
SEQUENCE: 65
gacaagaagt acagtattgg attggccatc gggacgaaca gcgtgggctg ggccgtcatc  60
accgacgagt acaaggtgcc atccaagaag tttaaggttc tggggaatac cgaccgccac  120
tcgatcaaga aaaatctcat cggggcgctg cttttcgaca gcggcgagac ggcggaagcg  180
acgcggctca agcggacggc tcgtcgccgt tacacccggc gtaagaaccg catctgttac  240
ctccaggaga tattcagcaa cgagatggcg aaggtggacg actccttttt ccaccgtctt  300
gaggagtcct tcctggtcga ggaggacaag aagcacgagc gccacccgat cttcgggaac  360
atcgtggacg aggtggccta ccacgagaag taccccacga tctaccacct ccgcaaaaaa  420
ctcgtggact caactgacaa ggccgatttg aggcttatct acctcgccct cgcccacatg  480
attaagttcc gtgggcactt cctaatcgag ggtgacctca accccgacaa ctctgacgtg  540
gacaagctgt tcatccagct tgtgcagacc tacaatcagc tctttgagga gaatccgatc  600
aacgcatctg gtgtggacgc aaaggccatc ctcagcgcgc ggctgagcaa gtctaggcgg  660
ttggagaacc tgatcgccca actgcccggc gagaagaaaa atggcctctt cggcaacctg  720
atcgccctgt cgctggggct cacgccgaac ttcaagagta actttgacct ggcggaggac  780
gctaagctcc agctatctaa ggacacatac gacgacgacc tggacaacct gctggcccag  840
atcggcgacc agtacgccga cctcttccta gccgccaaga acctgtccga cgccatcctc  900
ctcagcgaca tcctgcgcgt gaacacggag atcacgaagg ctccgctcag cgcctccatg  960
attaagcggt acgacgagca ccaccaagac ctaactttac tcaaagccct cgtgcggcag  1020
cagcttcccg agaagtacaa agagatattt tttgatcagt ccaagaacgg ttatgcgggc  1080
tacatcgacg gcggcgcgag ccaggaggag ttctacaagt tcatcaagcc catcctggag  1140
aagatggacg gcacggagga gctgctcgtg aagctcaacc gtgaagacct cctgcgaaag  1200
cagcgaacct tcgacaacgg ttcgatcccg caccagatcc acctcgggga gctgcacgcc  1260
atcctgaggc gacaggagga cttctaccct ttcctaaagg acaaccgcga gaagattgaa  1320
aaaatcctga cgtttcgcat accctactac gtcggcccgc tggcgcgcgg caactcccgg  1380
ttcgcctgga tgacccgtaa gagcgaggag acgatcaccc cgtggaactt cgaggaggtc  1440
gtggacaagg gcgcgagcgc gcagagcttc atcgagcgca tgaccaactt cgacaagaac  1500
ctcccgaacg agaaggtgct cccaaagcac tccctcctgt acgagtattt caccgtgtac  1560
aacgagttga caaaggtgaa gtacgtgacg gagggaatgc ggaagcctgc gttcctctcg  1620
ggcgagcaga agaaggcaat cgtggacctg ctcttcaaga ccaaccggaa ggtgacggtg  1680
aagcagctca aggaggacta cttcaaaaaa atcgagtgct tcgactccgt ggagataagc  1740
ggcgtggagg accgattcaa cgcctccctc ggcacctacc acgacctcct taagatcatc  1800
aaggacaagg acttcctgga caacgaggag aacgaggaca tcctggagga catcgtgctc  1860
accctgaccc tcttcgagga ccgggagatg atcgaggagc gcctcaagac gtacgcccac  1920
ttgttcgacg acaaggtgat gaagcagctc aagcggcggc gatacaccgg gtggggccgc  1980
ctatcccgca aacttatcaa cggcatccgc gacaagcagt ccggcaagac gatcctggat  2040
ttcctcaagt cggacgggtt cgccaaccgg aacttcatgc agctcatcca cgacgacagc  2100
ctcacgttca aggaggacat ccagaaggcc caagtgagcg gtcaagggga cagcctccac  2160
gagcacattg cgaaccttgc tgggagccct gcgatcaaga aggggatatt gcaaaccgtg  2220
aaggtcgtgg acgagttggt gaaggtcatg ggcgacacaa agcccgagaa catcgtgatc  2280
gagatggcca gggaaaatca gaccacgcag aagggccaaa aaaacagccg cgagcggatg  2340
aagcggatcg aggagggcat caaggagctg ggtcgcaga tcctcaagga gcacccggtg  2400
gagaacacgc agctccagaa cgagaagctg tacctctatt acctacagaa cgggcgggat  2460
atgtacgtgg accaggagct agacatcaac cgcctgtccg actacgacgt ggaccatatc  2520
gtcccgcagt cgttcttgaa ggacgacagc atcgacaaca aggtgctcac aagatcggat  2580
aagaatcgag gcaagtccga caacgtgccc tcggaggagg tggtcaagaa aatgaaaaac  2640
tactggcggc agttgctgaa cgccaagctc attacgcagc ggaagttcga caacctgacg  2700
aaggctgaac gtggtgggct cagcgagcta gacaaggcgg ggttcatcaa gcggcagctc  2760
gtcgagaccc ggcagatcac caagcacgtg gcgcagatcc tggactcgcg catgaacacc  2820
aagtacgacg agaacgacaa gctcatccgt gaggtgaagg tcatcaccct taagtctaag  2880
ctggtcagtg acttccgcaa ggacttccag ttctacaagg tccgggagat caacaactac  2940
caccacgcgc acgacgccta cctcaacgcg gtggtgggga cggcgcttat taagaaatat  3000
```

-continued cccaagctgg aaagcgagtt cgtttacggc gactacaagg tgtacgacgt ccgcaagatg 3060
atcgcaaagt cggaacagga aatcggaaag gcgacggcca aatatttctt ttactccaac 3120
atcatgaatt tttttaagac ggagatcacc ctggcgaacg gggagatccg caagcggccc 3180
ctcatcgaga ccaacgggga gacgggcgag atcgtctggg acaagggccg ggacttcgcc 3240
accgtgcgga aggtgctttc tatgcctcaa gtcaatatcg tcaaaaagac agaggtgcag 3300
accggcgggt tcagcaagga gtctatcctg ccgaagcgca actcggacaa gctcatcgcg 3360
cgcaagaaag actgggaccc caaaaaatat ggcgggttcg actcgccgac cgtcgcctac 3420
agcgtcctcg tggtggctaa ggtcgagaag ggcaagagca aaaagctaaa gtcggtgaag 3480
gagctgctgg gcatcaccat catggagcgc tcgtctttcg agaagaatcc aatcgacttc 3540
ctagaggcga aggggtacaa ggaggtcaaa aaggatctta tcatcaaact gccgaagtac 3600
agtctgttcg agctggagaa cgggcggaag cggatgctgg ctagtgcggg cgagttgcag 3660
aagggcaacg agttggcact gccctccaag tacgtgaact tcctgtacct ggcctcccac 3720
tacgagaagc tcaaggggag ccccgaggac aacgagcaga agcagctatt cgtcgagcag 3780
cacaagcact acctggacga gatcatcgag cagatcagtg agttctccaa gcgggtcatc 3840
ctcgcggacg ccaacctgga caaggtgctg agcgcgtaca acaagcacag ggacaagcca 3900
atcagggaac aggccgagaa catcatccac ctgttcaccc tgaccaacct gggtgcaccg 3960
gctgccttca agtactttga cacgaccatc gaccggaagc gctacacctc cacgaaggag 4020
gtgctggacg ccacgctgat ccaccagagc atcaccgggc tctacgagac acggatcgac 4080
ctgagccagc ttggcgggga c 4101

SEQ ID NO: 66 moltype = DNA length = 4092
FEATURE Location/Qualifiers
source 1..4092
mol_type = other DNA
organism = synthetic construct
SEQUENCE: 66
gacaaaaagt attccattgg actcgctatc ggcacgaaca gcgtcgggtg ggcggtcatc 60
actgacgagt acaaggtgcc gagcaagaag tttaaggtgc tgggaaacac cgacaggcac 120
tcgatcaaga aaaatcttat cggggcccta ctcttcgact ccggagaaac cgccgaggcc 180
acccggttga agcgcacggc ccgccgtcgc tacaccaggc gcaagaaccg gatctgctac 240
ctccaggaga tattcagcaa tgagatggcg aaggtggacg actcgttttt tcacaggcta 300
gaggagtctt tcctcgtgga ggaggacaag aaacacgagc gccaccccat cttcggcaac 360
atcgtggatg aggtggcata tcacgagaag tacccaacca tctaccacct ccgcaaaaag 420
ctcgtggact ctaccgacaa ggccgacctc cgtctgatct acctcgcgct ggcccacatg 480
attaagttcc gaggacactt tctgatcgag ggcgacctga acccagacaa cagcgacgtg 540
gacaagctgt tcatccaact tgtccagacc tacaatcagc tcttcgagga gaaccctatc 600
aacgcctcgg gcgtggacgc gaaggccatc ctgtccgccc gcctgagcaa gtcgcggcgg 660
ctggagaacc tgatcgccca gctccccggc gaaaaaaaga acggcctctt cggcaacctc 720
atcgcgttgt cgctggggct caccccgaac ttcaagtcca acttcgacct ggccgaggac 780
gctaaactcc agctctcgaa ggatacctac gacgacgacc tcgacaacct gctggcccag 840
atcggcgacc agtacgcgga ccttttcctg gcggccaaga acctgagcga cgcgatcctc 900
cttagcgaca tactccgtgt gaacaccgag atcacgaagg ccccgctctc cgcgtccatg 960
attaagcgct acgacgagca ccaccaagac cttaccctgc ttaaggcgct ggtcaggcag 1020
cagttaccgg agaagtacaa ggagatcttt tttgatcaat ctaagaacgg ttacgccggg 1080
tacatcgacg gcggcgcgtc ccaggaggag ttctacaagt tcatcaagcc gatcttggag 1140
aaaatggacg ggaccgagga gctgctcgtg aagctcaacc gcgaagacct cctccgcaag 1200
cagcgcacct tcgacaacgg gagcatcccg caccagatcc acctgggaga gctgcacgcg 1260
atcctgcgga gacaagagga cttctacccc ttcctcaagg acaaccggga gaagattgaa 1320
aaaatactta cttttcgtat cccgtactac gtcgggcccc ttgcgagggg caactccaga 1380
ttcgcgtgga tgacccgcaa gtccgaggag accatcaccc cgtggaactt cgaggaggtg 1440
gtggacaagg gcgcgtcggc ccagtcgttc atcgagcgca tgaccaactt cgacaagaac 1500
cttccgaacg agaaggtgct cccgaagcac agcctgctct acgaatattt tactgtgtac 1560
aacgagctga cgaaggtcaa gtacgttacg gaggggatga ggaagcccgc cttcctctcc 1620
ggcgagcaga agaaagccat tgtggatctc ctgttcaaga ccaaccgcaa ggtgacggtg 1680
aaacagctca aagaggacta cttcaagaag atcgagtgct tcgactccgt agagatcagc 1740
ggggtcgagg accgcttcaa cgcctcgctg ggcacgtacc acgacctgct aaagattatc 1800
aaggacaaag acttcctaga caatgaggag aacgaggaca ttctggagga catcgtgctg 1860
actctgacgc tgttcgaaga ccgcgagatg atcgaggagc ggcttaagac gtacgcccac 1920
ctgttcgacg acaaggtgat gaagcagttg aaacggcggc gctacaccgg gtggggccgc 1980
ctctcccgca agctcatcaa cggcatccgc gacaagcagt cggggaagac gatcctggac 2040
ttcctcaaga gcgacggctt cgccaaccga aacttcatgc agctaatcca cgacgacagc 2100
ctgacgttca aggaggacat ccagaaggcc caagtgagcg gccagggaga ctcgctacac 2160
gagcatatcg ccaacctggc tggcagcccg gcgattaaga aaggaatcct ccaaaccgtc 2220
aaagtggtgg acgagctggt gaaggtgatg ggccgccaca agcccgagaa cattgtgatc 2280
gagatggcgc gggagaacca gacgacgcag aagggccaaa aaaatagcag ggaaaggatg 2340
aagcgaatag aggaggggat caaggagctg gggagccaga ttctcaaaga gcacccggtc 2400
gagaacacac agctccagaa cgagaagctg tacctctact acctccaaaa cggccgcgat 2460
atgtacgtgg accaggaact agacatcaac cggctgagcg actatgacgt ggaccacatc 2520
gtgccgcagt ccttcctcaa ggacgactcg attgacaaca aagtgctcac tagatccgac 2580
aagaacagag gcaagagcga taacgtcccg tcggaggagg tcgtcaagaa aatgaaaaac 2640
tactggcggc agctcctaaa cgccaagctc atcacgcagc gtaagttcga caacctgacg 2700
aaggcggagc ggggcgggct gagcgagctg gacaaagcgg ggttcatcaa gcggcagctc 2760
gttgagacgc ggcagatcac aaagcacgtc gcgcaaatcc tcgactcccg catgaacacc 2820
aagtacgacg agaacgacaa gctcatccgg gaggtgaagg tcattaccct taaatcgaag 2880
ctcgtcagcg actttcgtaa ggacttccag ttctacaagg tcagagagat caacaactac 2940
caccacgccc acgacgccta tctgaacgcc gtggtgggca ccgcgcttat taagaagtac 3000
cccaagctgg agtccgagtt cgtgtacggc gactacaagg tttatgacgt caggaagatg 3060
atcgccaagt cggaacagga gatcggaaaa gctaccgcca aatatttctt ctatagcaac 3120
atcatgaact tcttcaaaac cgagatcacc ctcgccaacg gcgagatccg gaagcgcccg 3180

```
ctcatcgaga ccaacgggga gaccggggag atcgtctggg acaaggggcg ggacttcgct  3240
actgtccgaa aggtgctctc catgccacaa gtgaatatcg tcaagaaaac agaggtgcag  3300
accggagggt tcagtaagga gtccatcctg cccaagcgga actccgacaa gctaattgct  3360
cgcaaaaagg attgggatcc taaaaaatat ggcggcttcg actcgcccac ggtcgcctac  3420
tctgtgctgg tcgtggcgaa ggtggagaag ggcaagtcca agaagctcaa gagcgtcaag  3480
gagctgctgg ggatcacgat catggagcgt agttcgtttg agaagaatcc catcgacttc  3540
ctggaggcta agggctacaa ggaggtcaaa aaggacctca tcattaagct gccgaagtac  3600
agcctcttcg agctggagaa cgggcggaag cgtatgctcg cctccgctgg ggagttacaa  3660
aaggggaacg agctggcgct gccgtctaag tacgtcaact tcctgtacct ggcctcccac  3720
tacgagaagc tcaaggggtc gccggaggac aacgagcaga agcagctctt cgtagagcag  3780
cacaagcact acctggacga gatcatcgag cagatttcag agttctcaaa gcgggtcatc  3840
ctcgccgacg ccaacctgga caaggtgctc tcggcctaca acaagcaccg ggacaagccg  3900
atccgcgaac aggccgaaaa catcatccac ctgttcacgc tcaccaacct cggtgccccg  3960
gcggccttca agtactttga cacgaccatc gaccggaagc gctatacctc gacgaaggag  4020
gtgctggacg ccaccctgat ccaccagtcc atcaccgggc tttacgagac ccggatcgac  4080
ctctcgcagc ta                                                      4092

SEQ ID NO: 67           moltype = DNA  length = 4101
FEATURE                 Location/Qualifiers
source                  1..4101
                        mol_type = other DNA
                        organism = synthetic construct
SEQUENCE: 67
gacaagaagt atagtattgg actcgccatc ggaaccaact ctgtggggtg ggctgttatt  60
acagatgaat ataaggtgcc atccaaaaag tttaaagttc tgggcaatac tgatagacac  120
tcaatcaaga agaatctgat aggtgcactt ctgtttgata gtggagagac tgccgaggca  180
accagactta aaaggactgc aagaagaaga tataccagaa gaaagaatag gatttgctat  240
ttgcaggaaa tcttcagcaa cgaaatggcc aaggttgatg actcattttt ccataggttg  300
gaggagagtt ttcttgtgga ggaagataag aagcacgaaa gacacccaat tttcgggaat  360
atagtggacg aggtggctta tcatgagaag tatcccacta tctaccacct gagaaagaaa  420
cttgtggact caaccgataa ggctgatctt aggcttatat acttggccct tgcacatatg  480
atcaaattca ggggccattt tcttatcgaa ggcgatctta atcccgataa ctcagatgtg  540
gacaagctgt ttatacaact tgtgcaaacc tacaatcaac tcttcgagga gaatcccatt  600
aacgcctccg gcgtggatgc aaaagccata ctgtcagcca gactgagcaa aagtaggaga  660
ctggagaatc ttatagccca actgcccggt gaaaagaaga atgggctctt cggaaatctg  720
atcgctcttt cattggggtt gacacccaac tttaagagta actttgactt ggcagaagat  780
gcaaagttgc agctcagtaa agacacatat gacgatgacc ttgacaatct cttggcacaa  840
ataggggatc aatacgctga ccttttcctc gctgccaaga acctcagcga cgctatactg  900
ttgtccgaca ttcttagggt taataccgaa attacaaagg cccctcttag tgcaagtatg  960
atcaaaaggt atgatgagca tcaccaagac cttacactgc tgaaggctct ggttagacag  1020
caactccctg aaaagtataa ggaaatattc ttcgaccaaa gtaagaacgg gtacgccggt  1080
tatattgatg gggcgcaag tcaagaagaa ttttacaaat tcatcaagcc aattcttgaa  1140
aagatggacg ggactgagga attgctggtg aaactgaata gagaggacct tcttagaaaa  1200
cagaggacat ttgacaatgg gtccatccca caccagattc atctggggga actccacgca  1260
atattgagga gacaagaaga cttttaccca ttccttaagg ataatagaga gaaaatcgaa  1320
aaaatcctga ctttcaggat tccttactat gttgggccac tggccagggg gaactcaaga  1380
ttcgcttgga tgacaaggaa gtcagaagaa accataaccc cttggaattt tgaagaggtg  1440
gttgataagg gggcatcagc ccagtctttc atagagagga tgaccaactt tgataaaaat  1500
cttccaaatg agaaggtttt gccaaaacat agtcttttgt acgagtactt tactgtttat  1560
aacgaattga ccaaggtgaa gtatgtgacc gagggaatga ggaagccagc atttttgtcc  1620
ggggagcaaa agaaagcaat cgttgatctt ctcttcaaga ccaacagaaa agtgaccgtg  1680
aaacaactga aggaagacta cttcaaaaag atagaatgtt tcgattcagt ggaaattagc  1740
ggtgttgaag acaggttcaa tgcttcattg ggtacttacc acgacctgtt gaagataatc  1800
aaagacaagg actttctcga taatgaggag aacgaagaca tcttggaaga cattgtgctt  1860
acactcactt tgtttgagga cagggaaatg attgaggaaa gactcaaaac ttacgctcat  1920
ttgtttgatg ataaggttat gaaacaacta aaaagaagaa ggtacaccgg ctggggaaga  1980
ttgagtagga aactgatcaa cggtattaga gataaacaat ccggaaagac tatcctcgat  2040
ttccttaaga gtgatggctt tgcaaatagg aattttatgc agctgattca tgacgactca  2100
cttaccttca aagaagacat ccaaaaagct caggtgtctg ggcaaggcga cagtctgcat  2160
gaacatatag ctaacttggc tgggagtccc gccatcaaga aggggatact tcaaacagtt  2220
aaagttgtgg acgaattggt gaaggtaatg ggaaggcaca agcctgaaaa tatagtgata  2280
gaaatggcaa gggaaaatca aacaacccag aagggacaga agaacagtag ggaaaggatg  2340
aaaaggatag aagaggggat caaagagctt ggtagccaga tcctcaagga acatccagtg  2400
gagaataccc aacttcaaaa cgagaaactc tatttgtact acttgcagaa cggaagagat  2460
atgtatgtgg accaagagct tgatattaac aggctgagcg attatgacgt tgaccacata  2520
gtgccccaat cattcctcaa ggatgactct attgataata aggtgctgac aaggagtgac  2580
aagaatagag ggaaatccga caacgttcca tccgaggaag ttgtgaagaa gatgaagaac  2640
tactggaggc agttgctgaa cgctaagctc attacccaga ggaaattcga taacctgacc  2700
aaagcagaga gaggcgggct gagcgaactc gataaagcag gtttcatcaa gagacaactc  2760
gtggagacta ggcaaattac taagcacgtg gctcaaatac tcgacagcag gatgaacaca  2820
aagtacgacg agaacgacaa gctcattaga gaggttaagg ttattactct gaaaagtaaa  2880
ttggttagcg atttcagaaa ggatttccaa ttctataagg ttagagagat caacaattat  2940
catcatgcac atgatgccta tctgaatgct gtggttggta cagcccttat caagaagtac  3000
cctaagctag agagcgagtt tgtgtacgga gattataagg tgtatgatgt gaggaaaatg  3060
atcgctaaaa gtgagcaaga gattggaaag gctaccgcca aatacttctt ttattccaat  3120
attatgaatt tcttcaagac agaaatcacc ctggctaacg gcgagataag gaagaggccg  3180
cttatcgaaa ctaatgggga gacaggcgaa atagtgtggg acaaagggag ggatttcgca  3240
actgtgagga aggttttgag catgcctcag gtgaatatcg ttaagaaaac cgaagttcaa  3300
actggagggt tctctaagga aagcattctc cccaagagga actccgacaa gctgattgct  3360
```

```
agaaagaaag actgggaccc caagaagtat ggcggattcg actcacccac tgtggcatat  3420
agcgttctcg tggtggcaaa ggttgaaaag ggtaaatcca aaaaactcaa atccgtgaag  3480
gaactccttg gcataactat tatggaaagg agtagctttg aaaagaatcc catcgacttt  3540
ctcgaagcta agggctataa ggaagttaag aaggacctta taatcaaact tccaaaatac  3600
tcccttttg agttggaaaa cggcagaaag agaatgttgg ccagtgccgg ggagcttcaa  3660
aagggcaacg aactggctct gcctagcaaa tatgtgaact tttgtatct ggcatcacac  3720
tacgagaaac ttaaaggctc tcctgaggac aacgagcaaa aacagctctt tgttgaacag  3780
cataagcact acctcgacga gattattgag cagatcagcg agttctcaaa gagagttatt  3840
ctggctgacg ctaatcttga caaggttttg tccgcttaca acaaacacag ggataagcca  3900
atcagggagc aggcagaaaa cataatccat ctctttaccc tgacaaacct cggtgccccc  3960
gctgctttca agtattttga tactaccatt gacaggaaga gatatacttc cactaaggaa  4020
gtgctcgacg caaccctcat acaccaaagt atcacaggcc tctatgaaac taggatagat  4080
ttgtctcaac ttgggggcga t                                             4101

SEQ ID NO: 68          moltype = DNA  length = 4101
FEATURE                Location/Qualifiers
source                 1..4101
                       mol_type = other DNA
                       organism = synthetic construct
SEQUENCE: 68
gacaaaaagt attccatcgg gcttgctatc ggaaccaact ctgtggggtg ggcagttatt  60
accgacgaat acaaggtgcc cagcaagaag tttaaggttc tggggaacac agatagacat  120
agcataaaga aaaacctgat aggcgcactg ttgttcgact ccggggaaac agccgaagct  180
accaggctga agagaactgc aagaagaagg tacaccagaa gaaaaaacag aatatgttat  240
ctccaagaga ttttctctaa cgagatggcc aaggtggacg actcattctt tcacagactg  300
gaagaatctt tccttgtgga agaagataag aaacacgaga ggcaccctat ttttggcaat  360
atcgtggatg aggtggctta ccacgaaaaa taccctacaa tataccacct caggaaaaaa  420
ttggttgata gtacagacaa ggccgacctc aggctcatct atttggccct ggcccatatg  480
attaaattca gggggcactt tctcatcgag ggagatttga accccgacaa cagtgatgtt  540
gataagctct ttattcagct cgtgcagact tacaatcagt tgtttgagga aaaccccatt  600
aatgcttccg gggtggacgc caaggcaatc ctttctgcaa gactctcaaa gtcaaggaga  660
ctcgaaaatc tgatagcaca gcttccagga gagaagaaga acgggctctt tggaaacctg  720
atcgctctgt cactcggact cacacccaat ttcaaaagca attttgattt ggcagaggac  780
gctaagctgc aactcagtaa ggatacctac gacgatgact tggataatct gctcgcacaa  840
attggggacc agtatgcaga cctgtttctc gcagctaaga acttgagtga cgccatattg  900
ctcagtgaca tcctcagggt taataccgag attacaaaag ctccactctc tgcaagcatg  960
atcaagaggt atgacgagca ccatcaagac ctgacactcc ttaaggcgtt ggttaggcag  1020
caacttcctg aaaagtataa ggaaatcttc ttcgatcaaa gcaaaaacgg ctacgccggc  1080
tatatagacg gggagcatcc ccaagaagaa ttttataagt tcataaaacc tatattggag  1140
aagatggacg ggacagagga attgctcgtg aaactgaaca gggaggatct cctcaggaag  1200
caaaggacct tcgacaatgg ctccatccca catcagattc acctcggcga actgcacgca  1260
atactgagaa gacaagagga cttttatcct ttcctgaagg acaacaggga gaaaatcgag  1320
aaaatcttga cattcagaat cccatactac gttgggcctc tggccagagg taacagtagg  1380
ttcgcctgga tgactaggaa atcagaggag actattacac cctggaactt tgaagaagtt  1440
gttgataagg gagcttcagc acaatcattc atcgaaagaa tgacaaactt tgacaaaaat  1500
ctgcctaatg agaaagtgct cccaaaacat tccctgctgt atgagtattt taccgtttat  1560
aacgagctta ccaaggtgaa atacgttact gaaggtatga gaaagccagc ttttctttca  1620
ggggagcaaa agaaggctat cgtggatctt ctctttaaga ccaacagaaa ggttaccgtg  1680
aagcagctta aggaagacta ctttaaaaag atcgagtgtt ttgactcagt ggaaataagc  1740
ggtgttgaag atagattcaa cgcatccttg ggaacttatc atgatcttct taagataatc  1800
aaggataaag actttctcga caacgaggaa aacgaagata tactggagga catagttctg  1860
acacttactt tgttcgagga tagggagatg atcgaggaaa gactgaaaac atatgctcac  1920
cttttcgacg acaaagttat gaaacaactc aagagaagga gatatacagg gtgggggaga  1980
ttgagcagga aactgattaa tggtatcaga gacaaacagt caggaaaaac aatactcgac  2040
tttttgaaat cagacgggtt cgcaaatagg aatttcatgc agcttataca cgacgattca  2100
cttactttta aagaggacat tcaaaaggct caagttagtg gacaaggtga ctccctccac  2160
gaacacatcg caaatctcgc tggcagccct gcaattaaga agggtatact ccagacagtt  2220
aaggttgttg acgagctggt taaagtgatg ggaagacaca aacccgagaa catagtgata  2280
gagatggcca gggaaaacca aaccactcaa aaagggcaga aaaattccag agagaggatg  2340
aaaaggattg aagaaggtat caaggagctg ggtagccaaa ttctgaaaga acatcctgtg  2400
gaaaacactc aactccagaa tgagaaactc tatctgtact atctgcaaaa tgggagagat  2460
atgtatgtgg accaggaact ggacataaac aggctctcag attacgatgt ggatcatatc  2520
gtgccacagt cctttcttaa ggatgatagc atcgacaata aggtgcttac caggtccgac  2580
aagaacaggg gaaagtcaga taacgtgcct tctgaagaag ttgttaaaaa gatgaagaac  2640
tactggagac agctgcttaa cgctaagctc ataacacaga ggaagtttga caacttgacc  2700
aaggccgaga gaggcggact ctcagaattg gataaggcag ggttcataaa aaggcagctg  2760
gtggaaacaa ggcagataac taaacatgtg gctcagatcc tcgatagtag gatgaataca  2820
aaatacgatg agaacgacaa gctcataagg gaggttaaag tgataactct gaaatccaaa  2880
ctggttagcg attttaggaa ggatttccag ttttacaaag ttagggagat caacaattat  2940
catcacgccc acgatgccta cttgaacgca gttgtgggta ctgcacttat caaaaagtac  3000
cctaagctgg aatccgagtt tgtttatgga gactataagg tgtacgacgt tagaaaaatg  3060
attgcaaagt cagagcagga gatagggaaa gccactgcaa aatatttctt ttatagcaat  3120
atcatgaatt tctttaagac agaaatcaca ctggccaatg gggaaataag gaagaggccc  3180
ctgatcgaaa ctaatggcga gacaggggag attgtgtggg ataaaggtag ggactttgca  3240
acagtgagga aagtgctgag catgccccaa gttaatatcg ttaaaaagac cgaggttcaa  3300
acagggggct ttagtaagga aagcattttg cccaagagga atagtgacaa attgattgct  3360
aggaaaaaag attgggaccc caaaaagtat ggcggatttg atagccccac tgttgcttac  3420
tccgtgctcg tggttgcaaa ggtggagaag ggaaagagca agaaactgaa gtcagttaag  3480
gaactccttg gtatcactat catggaaaga agctcctttg agaagaaccc tattgacttc  3540
```

```
ctggaggcta aagggtacaa agaggttaag aaagacctta tcattaaatt gcccaaatat  3600
agtcttttcg agcttgaaaa cggaagaaag aggatgcttg catccgctgg cgaattgcaa  3660
aagggcaatg agcttgctct cccttccaag tatgtgaact tcctttatct tgcctcacac  3720
tatgaaaaac tcaaaggttc acccgaagac aacgaacaaa agcaactatt tgtggaacaa  3780
cacaagcact acctggacga aatcattgag caaatttctg agttttcaaa aagggtaatc  3840
ttggctgacg caaatctcga caaagttttg tcagcttaca acaaacatag agataagcca  3900
attagagagc aagctgagaa tatcatccat ctgtttaccc tgactaacct tggagcgcct  3960
gctgctttta aatatttcga caccacaatc gacaggaaga ggtacactag cactaaggaa  4020
gttctcgacg ccaccctcat ccaccagagt attacaggcc tgtacgagac aagaattgat  4080
ctttctcaac ttggtggtga c                                            4101

SEQ ID NO: 69          moltype = DNA  length = 4101
FEATURE                Location/Qualifiers
source                 1..4101
                       mol_type = other DNA
                       organism = synthetic construct
SEQUENCE: 69
gataagaagt actcaatcgg tctggcaatc ggaaccaact ctgtgggttg ggcagtgatt  60
acagatgagt ataaggtgcc aagcaaaaaa ttcaaggtgc tgggtaatac cgacagacac  120
agcattaaga agaatttgat tggagcactc ctctttgact caggggaaac agcagaggca  180
acaaggctga agaggacagc aaggcggagg tacacaaggc ggaaaaacag gatatgctac  240
ctccaggaaa tctttagcaa cgagatggct aaagtggatg atagcttttt ccatagactc  300
gaagaatcct ttcttgttga agaggacaaa aagcatgaaa ggcatcccat cttcggcaat  360
atagttgatg aggttgcata ccatgagaag taccccacaa tctaccacct cagaaagaaa  420
cttgtggact ccacagataa agcagacctg aggctcatat acctcgcact cgcacacatg  480
atcaagttca gagggcactt tctcatcgaa ggtgacctga atccagataa ttcagatgtg  540
gataaactgt ttatacagct ggtgcaaaca tacaaccaac ttttcgagga aaacccaatc  600
aatgcctccg gtgttgatgc aaaggccatc ctgtcagcaa gactcagcaa aagcaggcgg  660
ctcgaaaacc tcatcgccca gcttcccggt gaaaagaaga acgggctctt tggtaatctc  720
atcgcattga gccttggtct tactccaaac ttcaagagca attttgatct ggcagaggat  780
gctaaactgc aactctcaaa ggacacatat gacgatgacc ttgacaatct gttggcccag  840
atcggggacc aatatgcaga cctcttcctg gccgcaaaga atctgtcaga tgcaatcctc  900
ttgtccgaca tactgagagt taacactgag atcacaaagg cacctctgtc cgcctccatg  960
attaagagat acgatgagca tcaccaggat ctgactttgc tcaaagccct cgttagacag  1020
cagttgccag aaaagtacaa agaaatattc tttgatcaat caaaaaacgg atatgcaggg  1080
tacatcgacg gtggggcaag ccaggaagag ttctacaaat tcatcaaacc tatcctggaa  1140
aagatggatg ggacagaaga gctgctggtt aagctgaata gggaagacct cctcagaaag  1200
cagaggacat ttgataacgg gagcatccct catcaaatcc acctcggtga actccatgct  1260
atcctgagaa ggcaggaaga cttttatcca tttttgaagg acaataggga gaaaatcgaa  1320
aaaatcctga cattcagaat cccatactac gttggtcctc tggcaagagg taacagtagg  1380
ttcgcatgga tgacaaggaa aagcgaggag acaatcacac cctggaattt tgaggaagtt  1440
gttgacaagg gtgccagcgc acaatccttt atcgaaagaa tgacaaattt cgacaagaat  1500
ctgcctaacg aaaaggttct cccaaagcat tcactcctgt acgaatattt tacagtttat  1560
aacgaactga ctaaagttaa atacgttacc gagggtatga ggaagccagc attcctttcc  1620
ggggaacaga agaaagctat tgtggacctc ctgttcaaga caaatagaaa agtgacagtt  1680
aagcaactca aagaggatta cttcaaaaag atcgaatgtt ttgactctgt ggagatcagc  1740
ggggtggagg atagattcaa cgccagcctg ggtacatatc atgatctcct gaaaatcatt  1800
aaagacaagg acttccttga caacgaggag aacgaggaca ttctggaaga cattgttctg  1860
accctcacac tctttgagga tagggagatg attgaggaaa gactgaagac ctacgcccac  1920
ctctttgacg ataaagtgat gaaacagctc aagagaagaa ggtatacagg ttgggggaga  1980
ctgagcagga agttgatcaa tgggattagg gacaaacagt ccgggaaaac aatcctcgat  2040
tttctgaagt cagacggttt cgcaaacaga aattttatgc agctcattca cgatgacagc  2100
ttgacattca aggaagacat ccaaaaggct caagtgagcg gccaagggga tagcctccac  2160
gagcatattg caaatctggc aggttcacca gccatcaaaa agggcatact tcagacagtt  2220
aaggttgtgg acgaattggt taaagttatg ggcaggcata agccagagaa tatcgttatc  2280
gaaatggcaa gggagaacca aacaactcaa aaagggcaga aaaatagcag agagaggatg  2340
aaaagaatcg aggaagggat caaggaactt gggtcccaaa tcctcaagga gcacccagtt  2400
gaaaatactc aactgcaaaa cgagaagctc tatctctact atctccaaaa cgggagggat  2460
atgtatgttg accaggagct ggatattaac agactgtcag attatgatgt tgatcatatc  2520
gtgccccagt cattcctgaa ggacgattcc atcgacaaca aagttctcac aaggtccgat  2580
aaaaacaggg gcaagtccga taacgttcca agcgaagaag tggtgaaaaa gatgaaaaac  2640
tattggagac aacttctgaa tgcaaagttg attactcaga gaaagtttga caacctcaca  2700
aaagcagaaa gaggcgggct tagcgaactc gataaggcag ggtttatcaa aagacagctg  2760
gttgagacaa ggcagatcac aaaacatgtg gcacagatcc ttgactcaag gatgaatacc  2820
aagtatgatg agaatgataa gttgatcagg gaggttaaag ttatcacact caaatccaaa  2880
ctggtgtcag acttcaggaa agactttcaa ttttataagg tgagggagat caataactac  2940
caccatgcac atgacgccta cctgaacgca gtggtgggta cagcattgat taaaaaatac  3000
cctaagctgg agtctgagtt tgtgtacggg gactacaagg tgtacgacgt gaggaaaatg  3060
atagccaagt ccgagcagga gatcgggaaa gcaacagcta agtatttctt ttacagtaat  3120
atcatgaatt tctttaaaac tgagattact ctggcaaacg gggagatcag gaaaagaccc  3180
ctcatcgaga ctaatggtga aacaggtgag atcgtttggg acaaggggag ggattttgct  3240
actgttagaa aagttctgag tatgccacaa gtgaatattg tgaaaaagac agaagttcag  3300
acaggtgggt tctccaaaga atccatcctg cccaagagaa attcagacaa gctcatcgca  3360
agaaagaagg actgggaccc taagaagtac ggaggatttg acagccccac cgtggcctat  3420
tccgtgcttg ttgtggcaaa ggtggagaaa gggaagagca aaaaactgaa atccgtgaaa  3480
gaactgctgg gaattaccat catggaaaga agctcctttg agaagaaccc aatcgacttc  3540
ctggaagcaa aggatataa ggaagtgaaa aaggacctca ttatcaagct cccaaaatac  3600
tcacttttcg agttggagaa cggtagaaag aggatgctgg caagcgcagg ggaacttcag  3660
aaaggcaatg agctggcatt gccatcaaag tatgtgaact tcctctactt ggccagccat  3720
```

-continued

```
tacgagaaac ttaaaggtag cccagaagat aacgagcaaa aacagctctt tgtggaacag  3780
cataagcatt atctggatga gatcatagaa caaatctcag agttttccaa gagagttatc  3840
ctcgcagatg caaacctgga taaggttctc tcagcctata ataagcatag agacaagcca  3900
attagagagc aagcagagaa cattatccac ttgttcactc ttacaaacct gggggcacca  3960
gccgccttca aatatttcga tacaacaata gacagaaaga ggtataccag caccaaagaa  4020
gttctcgacg ccacactgat ccatcaatca atcacaggcc tttacgaaac taggatcgac  4080
ttgtcacaac tgggtgggga t                                            4101

SEQ ID NO: 70          moltype = DNA  length = 3307
FEATURE                Location/Qualifiers
source                 1..3307
                       mol_type = other DNA
                       organism = synthetic construct
SEQUENCE: 70
gagcaaggac acctacgacg acgacttgga caacctattg gcccagatag gtgaccagta  60
tgcagacctc ttccttgcgg ccaagaactt gagtgacgct atactgctca gtgacatcct  120
gagggtgaac actgagatca ctaaggcccc tctctctgcc tcaatgatta agcgttacga  180
cgagcatcac caggatctca ccctgcttaa ggcccttgtt cggcagcagc tccctgagaa  240
gtacaaggag atatttttg  accagtctaa gaacggctac gccggttaca ttgacggtgg  300
ggcaagccag gaggagttct acaagttcat caagccgatc cttgagaaga tggacggcac  360
cgaggagcta cttgtcaagt tgaaccggga agacctgctc cggaaacagc gtacattcga  420
caacggcagc atccctcacc agatccacct gggcgaacta cacgccatcc tccgacgtca  480
ggaggacttc tatccattct tgaaagataa cagggaaaaa atcgaaaaaa tacttacgtt  540
tcgaatacct tactacgtgg ggccccttgc tcggggaaac tccagattcg catggatgac  600
caggaagtca gaggagacca tcacaccctg gaactttgag gaggtggttg acaaaggtgc  660
ttctgcccag tccttcattg agcggatgac taacttcgac aagaacctgc ccaacgagaa  720
ggtgctgcca aagcacagcc tgctctacga atactttact gtgtacaatg agctgacgaa  780
ggtgaagtac gtgacagagg ggatgcggaa gcccgctttc ctgagcggcg agcaaaaaaa  840
agcaatcgtg gacctactgt tcaagaccaa ccgaaaggtg acagtgaagc agctcaagga  900
ggactacttc aaaaaaatcg agtgcttcga ctctgttgag ataagcggcg tggaggaccg  960
attcaacgcc tcattgggaa cctatcacga cctgctcaag atcattaagg acaaggactt  1020
cctggataat gaggagaatg aggacatcct ggaggatatt gtgctgaccc ttactctatt  1080
cgaggacagg gagatgatcg aggagcgact caagacctac gctcacctgt tcgacgacaa  1140
ggttatgaag caattgaagc gtaggcgata cacggggtgg ggaagactct cccgaaaact  1200
gataaacggc atcagggaca agcagtcagg gaagacgatc ttggacttcc tgaaatccga  1260
cgggttcgcc aaccgcaact tcatgcagct cattcacgac gactcactaa cgttcaaaga  1320
ggacattcag aaggctcaag tcagtggaca aggcgactcc ctgcacgagc acattgcaaa  1380
ccttgcgggc tccccggcga ttaaaaaggg cattctccaa acggttaagg tggtggacga  1440
gctggtgaag gtgatgggcc gacacaagcc tgagaacatc gtgatcgaga tggccaggga  1500
gaaccagact acccagaagg gtcagaagaa ctctcgggaa cgtatgaagc gtattgagga  1560
ggggattaag gagttgggct ctcaaatcct caaggagcac cctgtggaga acactcagct  1620
ccaaaacgag aagctgtacc tgtactacct gcaaaacggg cgcgatatgt acgtggatca  1680
ggagttggac atcaacaggc ttagcgatta cgacgtggac cacatcgtgc cacagtcatt  1740
cttaaaggac gacagcatcg acaacaaggt tctgacgagg agcgacaaga atcgagggaa  1800
aagtgacaat gttccatccg aggaggtggt caagaaaatg aagaactatt ggcgtcagct  1860
tctgaacgcc aagctcatca cccagcggaa attcgacaac ctgactaagg ctgagcgagg  1920
cggactctcc gagcttgaca aggctggctt catcaagcgg cagttggtcg aaacccgaca  1980
gataacgaag cacgttgccc agatacttga ctcccgtatg aacaccaagt acgacgagaa  2040
cgacaagctc atcagggagg tgaaggtcat taccctcaag tccaaactcg tcagcgactt  2100
tcgtaaggac ttccagttct acaaggtgcg cgagatcaat aactaccacc acgcacacga  2160
cgcctacctg aacgcagtgg ttggaaccgc gttgattaaa aagtacccca agttggagtc  2220
ggagttcgtt tacggggact acaaggtgta cgacgttcgg aagatgatcg ccaagtctga  2280
acaggagatc gggaaagcaa ccgccaagta tttcttctat agcaacatca tgaacttctt  2340
taaaaccgag atcacacttg ccaatggcga gatccgtaag aggccgctga tcgagacaaa  2400
tggggagact ggcgagatcg tgtgggacaa gggccgcgac ttcgcaaccg ttcggaaagt  2460
cttgtccatg cctcaagtca acatcgtcaa gaagactgag gtgcaaacag gcgggttctc  2520
gaaggagtcc atactgccca agaggaactc agacaagctc atagcacgca aaaaagactg  2580
ggatccaaag aaatacggcg ggttcgactc gccgacagtc gcatactccg tgttagtggt  2640
ggctaaagtg gaaaagggga agtccaagaa gctcaagtcc gtcaaggagt tgctcgggat  2700
caccattatg gaacggtcct cattcgagaa gaatcccatt gacttcctag aggcgaaggg  2760
ctacaaagag gtcaaaaagg acctaattat taagctcccc aagtattcac tcttcgaact  2820
tgaaaatggt cgtaagcgga tgttggcaag cgctggagag cttcagaagg ggaacgagct  2880
tgcactgcct tccaagtacg tgaacttcct gtacctcgcc tctcattacg agaagttgaa  2940
gggctcaccg gaggacaacg agcagaagca gttgttcgtg gagcagcaca agcactacct  3000
cgacgagatc attgagcaga taagtgagtt cagcaaacgg gtgatccttg ccgacgctaa  3060
cctggacaag gtgctgagcg cctacaacaa gcacagagac aagccgatcc gagagcaagc  3120
ggagaacatc atacacctgt tcaccctcac gaacctcggg gctcccgcag ccttcaaata  3180
ttttgacacg accatcgacc gtaaacgcta cactagcacg aaggaggtgc tggacgctac  3240
ccttatccac cagtccatca ccggcctgta cgagacgaga atcgacttgt cgcagctcgg  3300
tggtgac                                                            3307

SEQ ID NO: 71          moltype = DNA  length = 4101
FEATURE                Location/Qualifiers
source                 1..4101
                       mol_type = other DNA
                       organism = synthetic construct
SEQUENCE: 71
gacaaaaaat actcaattgg tctggcaatt gggaccaaca gtgtcggatg ggccgtgatt  60
accgacgagt acaaggtgcc gtccaaaaaa ttcaaggtgc ttgggaacac cgaccgccac  120
```

-continued

```
tcgatcaaga aaaacctaat cggtgcgttg cttttcgaca gtggggagac cgccgaggca  180
acacgcttaa aacgcacagc taggaggaga tatacacggc gcaagaaccg aatatgctac  240
ttacaggaga tattctccaa tgagatggcg aaggtggacg actctttctt ccatcggctt  300
gaggaatcct tcctggtcga ggaggacaag aagcacgagc gacacccgat attcgggaac  360
atcgttgatg aggtggcgta ccacgagaag tacccaacga tataccactt acgcaagaag  420
ctcgtggact ctacggacaa ggccgacttg cgccttatct acttggcact ggcccacatg  480
attaagttcc gaggccactt ccttatcgag ggtgacctga accccgataa ctccgacgtg  540
gacaagctct tcatccaact cgtccagaca tacaaccagc tattcgagga gaatcctatc  600
aacgcctctg ggtggacgc taaagctatc ctctcagccc gcctgtcaaa gtcgaggagg  660
ttggagaacc taatcgccca gcttccaggc gagaagaaaa atgggctgtt cggaaacctt  720
atcgcactct cactgggcct aaccccgaac ttcaagtcca acttcgacct ggcagaggac  780
gcgaaattgc agttgtcgaa agacacctat gacgatgacc tggacaacct gttggcccag  840
ataggggacc agtacgccga cctgttccta gcggccaaga acctgtccga cgccatcttg  900
ctgtcggata tactgcgggt gaacaccgag atcactaaag cacctctctc cgccagcatg  960
attaagcgtt acgacgagca ccaccaagat ttgaccctgc taaaggcact tgtacggcag  1020
cagcttcccg agaagtacaa ggagatcttt ttcgaccaaa gcaagaacgg ctacgccggg  1080
tacatcgacg gaggtgccag ccaggaggag ttctacaagt tcattaagcc catcctggag  1140
aagatggacg ggactgagga actacttgtg aagctgaacc gggaagactt actacggaag  1200
cagcgtacct tcgacaacgg ttctatccca catcagatcc atcttgggga gttgcacgcg  1260
atcctgcgac gccaggagga cttttacccc ttcctgaaag acaaccgcga gaaaatcgag  1320
aagatactga ccttcagaat accttactac gtcggaccccc ttgcgcgagg caactcaaga  1380
ttcgcgtgga tgaccaggaa atcagaggag accatcacac cctggaattt cgaggaggtg  1440
gttgacaagg gtgcctccgc ccagtccttt atcgaacgaa tgaccaactt cgacaagaac  1500
ttgcccaacg agaaggtgct ccccaaacac agcctcctct acgaatattt cacagtgtac  1560
aacgagctta ctaaagttaa gtatgttact gagggcatga ggaaacccgc cttcctgtca  1620
ggcgagcaga agaaagctat tgtggacctc cttttcaaga ccaaccggaa ggtgacagtg  1680
aagcagctca aggaggacta cttcaagaag atagagtgct tcgacagcgt ggagatcagc  1740
ggggtggagg acagattcaa tgcctctctc ggaacatacc acgacttgct taagatcatc  1800
aaggacaagg acttcctcga caacgaggaa aacgaggata ttctggagga tattgttctg  1860
actcttaccc tgttcgagga ccgggagatg atcgaggagc gtctcaagac ctacgcccac  1920
ctgttcgacg acaaagttat gaagcagctc aagcgtcgga gatataccgg atggggccgt  1980
ctgtctcgga agctcatcaa cgggatcagg gacaagcagt cagggaagac gatcttagac  2040
ttccttaagt ctgacggctt cgccaacagg aacttcatgc agttgatcca cgacgacagc  2100
cttaccttca aggaggacat ccagaaggcc caagtgagtg gccagggtga cagcctccac  2160
gagcatattg ctaatcttgc gggttcccca gcgattaaaa agggcatact tcaaaccgtt  2220
aaggtggtgg acgagcttgt caaggtgatg gggcgacaca agcccgagaa catcgtgatc  2280
gagatggcca gggagaacca gaccacccag aaggggcaga agaatagccg agaacgcatg  2340
aagcgcatcg aggaggggat taaggagcta gggagccaga tcctcaagga acatcccgtc  2400
gagaacaccc agctccagaa cgagaagcta tacctctact acttgcaaaa cgggagggat  2460
atgtacgtgg atcaggagtt ggacattaac cgcctaagcg actacgacgt agatcacatc  2520
gtgcctcagt cattcctcaa agacgacagc attgacaaca aagtcttgac ccgatccgac  2580
aagaaccgag gaaaatccga caatgtgccc tcagaggagg tcgtcaagaa aatgaagaac  2640
tattggaggc agctacttaa cgccaaactc ataacccagc ggaagttcga caacctgaca  2700
aaggctgagc ggggtgggct cagcgagctt gacaaggctg gcttcatcaa gcggcagttg  2760
gtggagacaa gacagataac gaagcacgtg gctcagatcc tggactctcg catgaacacg  2820
aagtacgacg agaacgacaa attgatccgc gaggtcaagg ttattacgct caagagcaaa  2880
cttgtcagcg atttccgcaa ggacttccag ttctacaagg tgagggagat taacaactac  2940
caccatgcac atgatgccta cttgaacgca gtggtgggga ccgcgcttat taaaaagtac  3000
cctaagttgg agtcagagtt cgtttatggg gactacaagg tgtacgacgt ccggaagatg  3060
attgcaaagt ctgaacagga aatcgggaag gccaccgcca aatatttctt ctacagtaac  3120
attatgaatt tttttaagac tgaaattact ctcgcaaacg gcgagatcag gaagcgtccc  3180
ctcatcgaga caaacgggga gaccggggag atagtctggg acaaggggcg ggacttcgct  3240
acggtgagga aggtgctctc gatgccacaa gtgaacatcg tcaaaaagac agaggtgcag  3300
accggtggct tctcaaagga gtcaatcctg ccaaaacgta acagcgacaa gctcatcgcc  3360
cgcaagaaag actgggaccc taagaagtat ggtgggttcg actcaccgac ggtcgcatac  3420
tccgttctgg tcgtggcaaa ggtggaaaag ggcaagtcca aaaaactgaa atccgtgaag  3480
gagttgcttg gcattaccat catggaacgc agcagcttcg agaagaaccc cattgacttc  3540
ctggaggcta aagggtacaa ggaggtcaag aaagatttaa ttattaagct acctaagtac  3600
agcttgttcg agctggagaa cggccgaaaa cgaatgctcg catccgccgg ggaacttcaa  3660
aagggcaacg agcttgcgct gccctccaag tacgtgaact tcctgtactt ggcatcccac  3720
tacgagaaac tcaagggtag cccagaggac aacgagcaga agcagctatt cgtggagcag  3780
cacaagcact acctcgacga gataatcgag cagatcagtg agttcagtaa gcgggtgata  3840
ctcgcggacg ccaacttgga caaggtgctt agtgcctaca acaagcaccg tgacaagccc  3900
atccgagaac aggctgagaa catcatccac cttttcactc tgacaaacct cggtgctccc  3960
gccgccttca aatacttcga cactaccatc gacaggaagc gctacacatc tacgaaggaa  4020
gttcttgacg ctacgcttat tcatcagtct atcacagggc tgtacgagac aaggatcgac  4080
cttagccaac tcggcgggga t                                            4101

SEQ ID NO: 72          moltype = DNA  length = 4488
FEATURE                Location/Qualifiers
source                 1..4488
                       mol_type = genomic DNA
                       organism = Zea mays
SEQUENCE: 72
tgttaggagt taatgagtat aatgttttga gcatattttg acacctacaa gtaatttttt  60
ctatatcctt ctttatgata tactatactt gaaagaagat tgaattaaaa ctaaaatctc  120
tctctcaagt tgaattgttg tgccacatct ttcactaatt tataattaaa gggtctcata  180
tttttgtac tttttataa ttatatttaa ttgtaaatct cataaaatat tgttagctcg  240
tgtcatcaaa tcactaaaat ccataaatag gattgatgca cttagctctt taaaatgaaa  300
```

-continued

```
aaggtacaaa aatataaaaa aaatcgtgaa ccccccaatc aatttctaat tgcattgtga  360
aaacttcgac aacaaaaata taagatacca ccaaaataaa atagtatcaa acaatatcat  420
cctctatttc aaacttcttt atgcaagcag cgtcattcac aatttcgcgt cctctatttt  480
acacactgta ctgcagacaa ccttaacatc tatgttggtt gtatcacata tttttgttgt  540
agaaaatttc caaagcacat ttaaacttga ttaaaatatt ttgggggttt aacgatattt  600
ttttattatt ctagaactaa atatattttt aaagcttata gatatatttt cgcgggctct  660
aaatactttt ttctccggtc ccaatctatt tctaatattt ttgaactttt tatatacttt  720
caatgtttta aataaacttt ttccgatttt cttagtaaaa agttgaaacc atcctaaaat  780
aaaaactatt tctaaccatg gtagagagct aatttaagcg gctttaagat ttgaagaaga  840
aattgcctta ttttagagtt cattcaagaa ggaaaaaatg gagtcctagt tgagggaaaa  900
caccacagat tccacagcct tcgcctgttc gccacctttc ctccaaaatt tgacccacac  960
gcggcgacgc ccgaggcccc gagcgaccac atcctccgcg gccgcggcga cgcccgaggc  1020
ctgcaaaacc ctaaccactc aggttctgcc ggccaccgcc accaccacca ccagtccacc  1080
accatgctga cagccactcc cctaccccat cagctcctgg ccaccttcct cctcgtcctg  1140
gcgtcggcga cccaacctgc agtccctgcc tccaccgacc gcgcagcgct tctcgccttc  1200
cgcgcgtccc tgtcgccgcc ctcccgcgcc gcgctatcct cgtggagcgg cccgctctcg  1260
ccatcctggc tcggcgtgtc gctccacccc gccacggcgc cagccccttc ggtcaccact  1320
ccctccgttg ccgaactctc gctccggggc ctcaacctca cgggcgtgat ccccgcggcg  1380
ccgctcgcgc tcctccgacg tctccggacg ctcgacctct ccgccaacgc gctttcggga  1440
gagcttccct gctccctccc gcgctcgctc ctcgcgctcg acctctcccg caacgcgctc  1500
tcgggggctg tccccacctg cctgccgtcc tcgctccccg cgctccgcac cctcaacctc  1560
tccgccaact tcctccgcct cccgctctcc ccgcgtctct ccttccccgc gcgcctcgct  1620
gcccttgatc tctcccgcaa cgccatctcc ggcgccgtcc cgccgcggat cgtcgccgac  1680
cccgacaact ccgctctcct cctcctcgac ctctcccaca accgcttctc cggcgagatc  1740
cccgccggta tcgcagccgt acggagcctg caggggcttt ttctcgcgga caaccagctt  1800
tccggggaca ttcctccggg gatagggaac ctgacctatt tgcaggtgct ggatttgtcg  1860
aataaccgat tgtccggttc agtgcctgcc ggacttgcag gctgcttcca gcttctgtac  1920
ctgcagcttg gggtaacca gctctctggg gcactccgtc cggagctcga cgcactagct  1980
agtctcaagg ttctagattt gtcgaataac aagatatctg gggagattcc cctgccgctg  2040
gctgggtgca ggtctttgga ggtggtggac ttgtcaggaa atgagatctc cggtgagctc  2100
agcagtgctg tagcgaaatg gctgagcttg aagttcttat cactggctgg taaccagctc  2160
tccggccacc tacctgactg gatgttctcg ttccccctgc tccagtggct tgatttgtct  2220
agtaataagt ttgtgggttt catcccagat ggggggttca atgtcagtga agtgcttaac  2280
ggtggaggtg gtcaggggac tccatcagag agtgtgcttc caccccaatt gtttgtgtca  2340
gcttctgtgg acacggtgtc atggcagttg gatttggggt atgatgttca ggcaactact  2400
ggtatagacc tgtctgggaa tgagctctgt ggggagatac cagaagggtt ggttgacatg  2460
aaggggttgg agtatttgaa cctctcctgt aattacttgg ctgggcagat ccctgcgggg  2520
cttgggggca tggggaggtt gcatacgctt gacttctcac ataatgggct gtcaggggag  2580
gtgcctcctg gaattgcagc catgacagtg cttgaggtgc ttaacctctc ctacaatagc  2640
ctgtctgggc ctttgccaac aacgaagttc ccaggagcat tagctggaaa cccaggaatt  2700
tgcagtggga aagggtgctc tgagaatgca aggactccag aagggaaaat ggaaggtagc  2760
aatcaccgcg gttggcttgg tggctggcat ggagagaatg gatgggtatc tcttggtgca  2820
ttttgtatca gcacaatgac tagcttctat gtatcattag caaccttact atgctcctct  2880
aatgcaagaa acttcgtgtt tcggcctgtg agggttgaat attaacaaga ggggagattg  2940
caaaatcagg ttgttttgaa gttcgagcga ctctggtctg cagctgatta acaagaaata  3000
tgagcatatg agatggatat cttcagccaa gaggaagtgc tgtctctttt aatgatcaat  3060
caagctctct tgattgtttc ctaatattct tgatcttggg atgtgtagat ctagttctaa  3120
tattcctact gttatagaat gcaatcacct gctggtgctt ggttgtagcc ctggcgtgtt  3180
tggaggattg gacaccaagg atgcacataa tttgaagcgc tggtactgtg aaccacttca  3240
gatgtaaata ttttctttgg tttttagttc tgatctagtt taaaactgga catgtattta  3300
gtgttgttga gctacctttc gatgttatat tatgtcaatt tgctggaaga tcatttgata  3360
acaattgtct aatccagtgg attagtcgtg tagattgtga agttcgttat gtttcttctt  3420
agtgctatgt atatcatctt tctgtctgaa cttagtttgg gggtaaaagg ctttgttatt  3480
atgtgactga aactgcaaat gtgcttgact atttcttggt gctgctcctg taacacctat  3540
agttttatag gtcaatggta atagctgcct gaagcagcat ccagcaggcc ggcaactgtt  3600
tttggtactg taatactttg gaacagaggc gcaaagtttg tgattgcaga atgatcaaca  3660
aatgtattta ttgcaaagtg tgagacaagg caacatacat atctctgttt tgtgcattac  3720
caaactaacc caggctgtaa ttgcagattg ataattccta tagccgtagc ttcttcagct  3780
ggataaggtg gagaataagc atcagtggct tttcaaaggg ttcggcactt gtgcagaatc  3840
agactcatgc aggaatccgg ttctaacttt tccactaaaa ccttttttcct ttctgaactt  3900
gctgcagtac ctaccactac ttgtaatgtt ggatcagttt cacagttaac cacagaattt  3960
cattgctttt aatcaaacgt gaaatggtca cacagaaaaa ccaacatcct tcagaaccgc  4020
tcgttttatc ttgttcttta gattacttca aatgtgagcg ctttgagatg gtcacctaag  4080
gtgtgtttgg ttgatgtact aaggtgtgtt tggttggatg tacaaagagt gatggaaggg  4140
ggcaacaaca gtttctatag tgtttggatg agtcacgtga ggacgagata aacattagag  4200
taatttttta tggcggcgtg atcccaaaaa atcgagggaa cggtgttatt cctgccttat  4260
cctattttga tctcaaacca aacacatcct aaactgtctt ggatctagat aaggtgacct  4320
ggacgcaaac gacgactgct gatggttggt ctcctgtcag gaactggctc gtctggccta  4380
gacaaaagaa ctggctcgtc tggcctagac aaaactttca tgtggccgtt ggccgttgac  4440
gttaagagga attgagatca ccgccggcgc caggtctatc atctgatc              4488

SEQ ID NO: 73           moltype = DNA  length = 1842
FEATURE                 Location/Qualifiers
source                  1..1842
                        mol_type = other DNA
                        organism = Zea mays
SEQUENCE: 73
atgctgacag ccactcccct accccatcag ctcctggcca ccttcctcct cgtcctggcg  60
tcggcgaccc aacctgcagt ccctgcctcc accgaccgcg cagcgcttct cgccttccgc  120
```

-continued

```
gcgtccctgt cgccgccctc ccgcgccgcg ctatcctcgt ggagcggccc gctctcgcca  180
tcctggctcg gcgtgtcgct ccaccccgcc acggcgccag ccccttcggt caccactccc  240
tccgttgccg aactctcgct ccggggcctc aacctcacgg gcgtgatccc cgcggcgccg  300
ctcgcgctcc tccgacgtct ccggacgctc gacctctccg ccaacgcgct ttcgggagag  360
cttccctgct ccctcccgcg ctcgctcctc gcgctcgacc tctcccgcaa cgcgctctcg  420
ggggctgtcc ccacctgcct gccgtcctcg ctccccgcgc tccgcaccct caacctctcc  480
gccaacttcc tccgcctccc gctctccccg cgtctctcct tccccgcgcg cctcgctgcc  540
cttgatctct cccgcaacgc catctccggc gccgtcccgc cgcggatcgt cgccgacccc  600
gacaactccg ctctcctcct cctcgacctc tcccacaacc gcttctccgg cgagatcccc  660
gccggtatcg cagccgtacg gagcctgcag gggcttttc tcgcggacaa ccagctttcc  720
ggggacattc ctccggggat agggaacctg acctatttgc aggtgctgga tttgtcgaat  780
aaccgattgt ccggttcagt gcctgccgga cttgcaggct gcttccagct tctgtacctg  840
cagcttgggg gtaaccagct ctctggggca ctccgtccgg agctcgacgc actagctagt  900
ctcaaggttc tagatttgtc gaataacaag atatctgggg agattcccct gccgctggct  960
gggtgcaggt ctttggaggt ggtggacttg tcaggaaatg agatctccgg tgagctcagc  1020
agtgctgtag cgaaatggct gagcttgaag ttcttatcac tggctggtaa ccagctctcc  1080
ggccacctac ctgactggat gttctcgttc cccctgctcc agtggcttga tttgtctagt  1140
aataagtttg tgggtttcat cccagatggg ggttcaatg tcagtgaagt gcttaacggt  1200
ggaggtggtc aggggactcc atcagagagt gtgcttccac cccaattgtt tgtgtcagct  1260
tctgtggaca cggtgtcatg gcagttggat ttggggtatg atgttcaggc aactactggt  1320
atagacctgt ctgggaatga gctctgtggg gagataccag aagggttggt tgacatgaag  1380
gggttggagt atttgaacct ctcctgtaat tacttggctg ggcagatccc tgcggggctt  1440
gggggcatgg ggaggttgca tacgcttgac ttctcacata atgggctgtc aggggaggtg  1500
cctcctggaa ttgcagccat gacagtgctt gaggtgctta acctctccta caatagcctg  1560
tctgggcctt tgccaacaac gaagttccca ggagcattag ctggaaaccc aggaatttgc  1620
agtgggaaag ggtgctctga gaatgcaagg actccagaag ggaaaatgga aggtagcaat  1680
caccgcggtt ggcttggtgg ctggcatgga gagaatggat gggtatctct tggtgcattt  1740
tgtatcagca caatgactag cttctatgta tcattagcaa ccttactatg ctcctctaat  1800
gcaagaaact tcgtgtttcg gcctgtgagg gttgaatatt aa                      1842

SEQ ID NO: 74          moltype = AA  length = 613
FEATURE                Location/Qualifiers
source                 1..613
                       mol_type = protein
                       organism = Zea mays
SEQUENCE: 74
MLTATPLPHQ LLATFLLVLA SATQPAVPAS TDRAALLAFR ASLSPPSRAA LSSWSGPLSP  60
SWLGVSLHPA TAPAPSVTTP SVAELSLRGL NLTGVIPAAP LALLRRLRTL DLSANALSGE  120
LPCSLPRSLL ALDLSRNALS GAVPTCLPSS LPALRTLNLS ANFLRLPLSP RLSFPARLAA  180
LDLSRNAISG AVPPRIVADP DNSALLLLDL SHNRFSGEIP AGIAAVRSLQ GLFLADNQLS  240
GDIPPGIGNL TYLQVLDLSN NRLSGSVPAG LAGCFQLLYL QLGGNQLSGA LRPELDALAS  300
LKVLDLSNNK ISGEIPLPLA GCRSLEVVDL SGNEISGELS SAVAKWLSLK FLSLAGNQLS  360
GHLPDWMFSF PLLQWLDLSS NKFVGFIPDG GFNVSEVLNG GGGQGTPSES VLPPQLFVSA  420
SVDTVSWQLD LGYDVQATTG IDLSGNELCG EIPEGLVDMK GLEYLNLSCN YLAGQIPAGL  480
GGMGRLHTLD FSHNGLSGEV PPGIAAMTVL EVLNLSYNSL SGPLPTTKFP GALAGNPGIC  540
SGKGCSENAR TPEGKMEGSN HRGWLGGWHG ENGWVSLGAF CISTMTSFYV SLATLLCSSN  600
ARNFVFRPVR VEY                                                     613

SEQ ID NO: 75          moltype = DNA  length = 223
FEATURE                Location/Qualifiers
source                 1..223
                       mol_type = other DNA
                       organism = Zea mays
SEQUENCE: 75
tccggagctc gacgcactag ctagtctcaa ggttctagat ttgtcgaata acaagatatc  60
tggggagatt cccctgccgc tggctgggtg caggtctttg gaggtggtgg acttgtcagg  120
aaatgagatc tccggtgagc tcagcagtgc tgtagcgaaa tggctgagct tgaagttctt  180
atcactggct ggtaaccagc tctccggcca cctacctgac tgg                      223

SEQ ID NO: 76          moltype = DNA  length = 103
FEATURE                Location/Qualifiers
source                 1..103
                       mol_type = other DNA
                       organism = Zea mays
SEQUENCE: 76
tggggagatt cccctgccgc tggctgggtg caggtctttg gaggtggtgg acttgtcagg  60
aaatgagatc tccggtgagc tcagcagtgc tgtagcgaaa tgg                      103

SEQ ID NO: 77          moltype = DNA  length = 63
FEATURE                Location/Qualifiers
source                 1..63
                       mol_type = other DNA
                       organism = Zea mays
SEQUENCE: 77
tggctgggtg caggtctttg gaggtggtgg acttgtcagg aaatgagatc tccggtgagc  60
tca                                                                63

SEQ ID NO: 78          moltype = AA  length = 74
FEATURE                Location/Qualifiers
```

-continued

```
source                  1..74
                        mol_type = protein
                        organism = Zea mays
SEQUENCE: 78
PELDALASLK VLDLSNNKIS GEIPLPLAGC RSLEVVDLSG NEISGELSSA VAKWLSLKFL  60
SLAGNQLSGH LPDW                                                   74

SEQ ID NO: 79           moltype = AA  length = 27
FEATURE                 Location/Qualifiers
source                  1..27
                        mol_type = protein
                        organism = Zea mays
SEQUENCE: 79
PLPLAGCRSL EVVDLSGNEI SGELSSA                                     27

SEQ ID NO: 80           moltype = AA  length = 11
FEATURE                 Location/Qualifiers
source                  1..11
                        mol_type = protein
                        organism = Zea mays
SEQUENCE: 80
LEVVDLSGNE I                                                      11

SEQ ID NO: 81           moltype = DNA  length = 23
FEATURE                 Location/Qualifiers
source                  1..23
                        mol_type = other DNA
                        organism = synthetic construct
SEQUENCE: 81
gaggtggtgg acttgtcagg aaa                                         23

SEQ ID NO: 82           moltype = DNA  length = 2367
FEATURE                 Location/Qualifiers
source                  1..2367
                        mol_type = other DNA
                        organism = synthetic construct
SEQUENCE: 82
gccgcggcga cgcccgaggc ctgcaaaacc ctaaccactc aggttctgcc ggccaccgcc  60
accaccacca ccagtccacc accatgctga cagccactcc cctaccccat cagctcctgg  120
ccaccttcct cctcgtcctg gcgtcggcga cccaacctgc agtccctgcc tccaccgacc  180
gcgcagcgct tctcgccttc cgcgcgtccc tgtcgccgcc ctcccgcgcc gcgctatcct  240
cgtggagcgg cccgctctcg ccatcctggc tcggcgtgtc gctccacccc gccacggcgc  300
cagccccttc ggtcaccact ccctccgttg ccgaactctc gctccggggc ctcaacctca  360
cgggcgtgat ccccgcggcg ccgctcgcgc tcctccgacg tctccggacg ctcgacctct  420
ccgccaacgc gctttcggga gagcttccct gctccctccc gcgctcgctc ctcgcgctcg  480
acctctcccg caacgcgctc tcgggggctg tccccacctg cctgccgtcc tcgctccccg  540
cgctccgcac cctcaacctc tccgccaact tcctccgcct cccgctctcc ccgcgtctct  600
ccttccccgc gcgcctcgct gcccttgatc tctcccgcaa cgccatctcc ggcgccgtcc  660
cgccgcggat cgtcgccgac cccgacaact ccgctctcct cctcctcgac ctctcccaca  720
accgcttctc cggcgagatc cccgccggta tcgcagccgt acggagcctg caggggcttt  780
ttctcgcgga caaccagctt tccggggaca ttcctccggg gatagggaac ctgacctatt  840
tgcaggtgct ggatttgtcg aataaccgat tgtccggttc agtgcctgcc ggacttgcag  900
gctgcttcca gcttctgtac ctgcagcttg gggtaacca gctctctggg gcactccgtc  960
cggagctcga cgcactagct agtctcaagg ttctagattt gtcgaataac aagatatctg  1020
gggagattcc cctgccgctg gctgggtgca ggtctttgga ggtctccggt gagctcagca  1080
gtgctgtagc gaaatggctg agcttgaagt tcttatcact ggctggtaac cagctctccg  1140
gccacctacc tgactggatg ttctcgttcc ccctgctcca gtggcttgat ttgtctagta  1200
ataagtttgt gggtttcatc ccagatgggg ggttcaatgt cagtgaagtg cttaacggtg  1260
gaggtggtca ggggactcca tcagagagtg tgcttccacc ccaattgttt gtgtcagctt  1320
ctgtggacac ggtgtcatgg cagttggatt tggggtatga tgttcaggca actactggta  1380
tagacctgtc tgggaatgag ctctgtgggg agataccaga agggttggtt gacatgaagg  1440
ggttggagta tttgaacctc tcctgtaatt acttggctgg gcagatccct gcggggcttg  1500
ggggcatggg gaggttgcat acgcttgact tctcacataa tgggctgtca ggggaggtgc  1560
ctcctggaat tgcagccatg acagtgcttg aggtgcttaa cctctcctac aatagcctgt  1620
ctgggccttt gccaacaacg aagttcccag gagcattagc tggaaaccca ggaatttgca  1680
gtgggaaagg gtgctctgag aatgcaagga ctccagaagg gaaaatggaa ggtagcaatc  1740
accgcggttg gcttggtggc tggcatggag agaatggatg ggtatctctt ggtgcatttt  1800
gtatcagcac aatgactagc ttctatgtat cattagcaac cttactatgc tcctctaatg  1860
caagaaactt cgtgtttcgg cctgtgaggg ttgaatatta acaagagggg agattgcaaa  1920
atcaggttgt tttgaagttc gagcgactct ggtctgcagc tgattaacaa gaaatatgag  1980
catatgagat ggatatcttc agccaagagg aagtgctgtc tcttttaatg atcaatcaag  2040
ctctcttgat tgtttcctaa tattcttgat cttgggatgt gtagatctag ttctaatatt  2100
cctactgtta tagaatgcaa tcacctgctg gtgcttggtt gtagccctgg cgtgtttgga  2160
ggattggaca ccaaggatgc acataatttg aagcgctggt actgtgaacc acttcagatg  2220
taaatatttt ctttggtttt tagttctgat ctagtttaaa actggacatg tatttagtgt  2280
tgttgagcta cctttcgatg ttatattatg tcaatttgct ggaagatcat ttgataacaa  2340
ttgtctaatc cagtggatta gtcgtgt                                     2367

SEQ ID NO: 83           moltype = AA  length = 605
```

-continued

```
FEATURE                Location/Qualifiers
source                 1..605
                       mol_type = protein
                       organism = synthetic construct
SEQUENCE: 83
MLTATPLPHQ LLATFLLVLA SATQPAVPAS TDRAALLAFR ASLSPPSRAA LSSWSGPLSP  60
SWLGVSLHPA TAPAPSVTTP SVAELSLRGL NLTGVIPAAP LALLRRLRTL DLSANALSGE  120
LPCSLPRSLL ALDLSRNALS GAVPTCLPSS LPALRTLNLS ANFLRLPLSP RLSFPARLAA  180
LDLSRNAISG AVPPRIVADP DNSALLLLDL SHNRFSGEIP AGIAAVRSLQ GLFLADNQLS  240
GDIPPGIGNL TYLQVLDLSN NRLSGSVPAG LAGCFQLLYL QLGGNQLSGA LRPELDALAS  300
LKVLDLSNNK ISGEIPLPLA GCRSLEVSGE LSSAVAKWLS LKFLSLAGNQ LSGHLPDWMF  360
SFPLLQWLDL SSNKFVGFIP DGGFNVSEVL NGGGGQGTPS ESVLPPQLFV SASVDTVSWQ  420
LDLGYDVQAT TGIDLSGNEL CGEIPEGLVD MKGLEYLNLS CNYLAGQIPA GLGGMGRLHT  480
LDFSHNGLSG EVPPGIAAMT VLEVLNLSYN SLSGPLPTTK FPGALAGNPG ICSGKGCSEN  540
ARTPEGKMEG SNHRGWLGGW HGENGWVSLG AFCISTMTSF YVSLATLLCS SNARNFVFRP  600
VRVEY                                                            605

SEQ ID NO: 84          moltype = DNA  length = 2392
FEATURE                Location/Qualifiers
source                 1..2392
                       mol_type = other DNA
                       organism = synthetic construct
SEQUENCE: 84
gccgcggcga cgcccgaggc ctgcaaaacc ctaaccactc aggttctgcc ggccaccgcc  60
accaccacca ccagtccacc accatgctga cagccactcc cctaccccat cagctcctgg  120
ccaccttcct cctcgtcctg gcgtcggcga cccaacctgc agtccctgcc tccaccgacc  180
gcgcagcgct tctcgccttc cgcgcgtccc tgtcgccgcc ctcccgcgcc gcgctatcct  240
cgtggagcgg cccgctctcg ccatcctggc tcggcgtgtc gctccacccc gccacggcgc  300
cagccccttc ggtcaccact ccctccgttg ccgaactctc gctccggggc ctcaacctca  360
cgggcgtgat ccccgcggcg ccgctcgcgc tcctccgacg tctccggacg ctcgacctct  420
ccgccaacgc gctttcggga gagcttccct gctccctccc gcgctcgctc ctcgcgctcg  480
acctctcccg caacgcgctc tcgggggctg tccccacctg cctgccgtcc tcgctccccg  540
cgctccgcac cctcaacctc tccgccaact tcctccgcct cccgctctcc ccgcgtctct  600
ccttccccgc gcgcctcgct gcccttgatc tctcccgcaa cgccatctcc ggcgccgtcc  660
cgcccgcggat cgtcgccgac cccgacaact ccgctctcct cctcctcgac ctctcccaca  720
accgcttctc cggcgagatc cccgccggta tcgcagccgt acggagcctg caggggcttt  780
ttctcgcgga caaccagctt tccggggaca ttcctccggg gatagggaac ctgacctatt  840
tgcaggtgct ggatttgtcg aataaccgat tgtccggttc agtgcctgcc ggacttgcag  900
gctgcttcca gcttctgtac ctgcagcttg ggggtaacca gctctctggg gcactccgtc  960
cggagctcga cgcactagct agtctcaagg ttctagattt gtcgaataac aagatatctg  1020
gggagattcc cctgccgctg gctgggtgca ggtctttgga ggtggtggac ttngtcagga  1080
aatgagatct ccggtgagct cagcagtgct gtagcgaaat ggctgagctt gaagttctta  1140
tcactggctg gtaaccagct ctccggccac ctacctgact ggatgttctc gttccccctg  1200
ctccagtggc ttgatttgtc tagtaataag tttgtgggtt tcatcccaga tggggggttc  1260
aatgtcagtg aagtgcttaa cggtggaggt ggtcagggga ctccatcaga gagtgtgctt  1320
ccaccccaat tgtttgtgtc agcttctgtg gacacggtgt catggcagtt ggatttgggg  1380
tatgatgttc aggcaactac tggtatagac ctgtctggga atgagctctg tggggagata  1440
ccagaagggt tggttgacat gaaggggttg gagtatttga acctctcctg taattacttg  1500
gctgggcaga tccctgcggg gcttgggggc atggggaggt tgcatacgct tgacttctca  1560
cataatgggc tgtcagggga ggtgcctcct ggaattgcag ccatgacagt gcttgaggtg  1620
cttaacctct cctacaatag cctgtctggg cctttgccaa caacgaagtt cccaggagca  1680
ttagctggaa acccaggaat ttgcagtggg aaagggtgct ctgagaatgc aaggactcca  1740
gaagggaaaa tggaaggtag caatcaccgc ggttggcttg gtggctggca tggagagaat  1800
ggatgggtat ctcttggtgc attttgtatc agcacaatga ctagcttcta tgtatcatta  1860
gcaaccttac tatgctcctc taatgcaaga aacttcgtgt ttcggcctgt gagggttgaa  1920
tattaacaag aggggagatt gcaaaatcag gttgttttga agttcgagcg actctggtct  1980
gcagctgatt aacaagaaat atgagcatat gagatggata tcttcagcca agaggaagtg  2040
ctgtctcttt taatgatcaa tcaagctctc ttgattgttt cctaatattc ttgatcttgg  2100
gatgtgtaga tctagttcta atattcctac tgttatagaa tgcaatcacc tgctggtgct  2160
tggttgtagc cctggcgtgt ttggaggatt ggacaccaag gatgcacata atttgaagcg  2220
ctggtactgt gaaccacttc agatgtaaat attttcttg gtttttagtt ctgatctagt  2280
ttaaaactgg acatgtattt agtgttgttg agctaccttt cgatgttata ttatgtcaat  2340
ttgctggaag atcatttgat aacaattgtc taatccagtg gattagtcgt gt          2392

SEQ ID NO: 85          moltype = AA  length = 333
FEATURE                Location/Qualifiers
source                 1..333
                       mol_type = protein
                       organism = synthetic construct
SEQUENCE: 85
MLTATPLPHQ LLATFLLVLA SATQPAVPAS TDRAALLAFR ASLSPPSRAA LSSWSGPLSP  60
SWLGVSLHPA TAPAPSVTTP SVAELSLRGL NLTGVIPAAP LALLRRLRTL DLSANALSGE  120
LPCSLPRSLL ALDLSRNALS GAVPTCLPSS LPALRTLNLS ANFLRLPLSP RLSFPARLAA  180
LDLSRNAISG AVPPRIVADP DNSALLLLDL SHNRFSGEIP AGIAAVRSLQ GLFLADNQLS  240
GDIPPGIGNL TYLQVLDLSN NRLSGSVPAG LAGCFQLLYL QLGGNQLSGA LRPELDALAS  300
LKVLDLSNNK ISGEIPLPLA GCRSLEVVDX VRK                              333

SEQ ID NO: 86          moltype = DNA  length = 2383
FEATURE                Location/Qualifiers
```

-continued

```
source                 1..2383
                       mol_type = other DNA
                       organism = synthetic construct
SEQUENCE: 86
gccgcggcga cgcccgaggc ctgcaaaacc ctaaccactc aggttctgcc ggccaccgcc  60
accaccacca ccagtccacc accatgctga cagccactcc cctaccccat cagctcctgg  120
ccaccttcct cctcgtcctg gcgtcggcga cccaacctgc agtccctgcc tccaccgacc  180
gcgcagcgct tctcgccttc cgcgcgtccc tgtcgccgcc ctcccgcgcc gcgctatcct  240
cgtggagcgg cccgctctcg ccatcctggc tcggcgtgtc gctccacccc gccacggcgc  300
cagccccttc ggtcaccact ccctccgttg ccgaactctc gctccggggc ctcaacctca  360
cgggcgtgat ccccgcggcg ccgctcgcgc tcctccgacg tctccggacg ctcgacctct  420
ccgccaacgc gctttcggga gagcttccct gctccctccc gcgctcgctc ctcgcgctcg  480
acctctcccg caacgcgctc tcgggggctg tccccacctg cctgccgtcc tcgctccccg  540
cgctccgcac cctcaacctc tccgccaact tcctccgcct cccgctctcc ccgcgtctct  600
ccttccccgc gcgcctcgct gcccttgatc tctcccgcaa cgccatctcc ggcgccgtcc  660
cgccgcggat cgtcgccgac cccgacaact ccgctctcct cctcctcgac ctctcccaca  720
accgcttctc cggcgagatc cccgccggta tcgcagccgt acggagcctg caggggcttt  780
ttctcgcgga caaccagctt tccggggaca ttcctccggg gatagggaac ctgacctatt  840
tgcaggtgct ggatttgtcg aataaccgat tgtccggttc agtgcctgcc ggacttgcag  900
gctgcttcca gcttctgtac ctgcagcttg gggtaaccca gctctctggg gcactccgtc  960
cggagctcga cgcactagct agtctcaagg ttctagattt gtcgaataac aagatatctg  1020
gggagattcc cctgccgctg gctgggtgca ggtctttgga ggtggtggac ttgtgagatc  1080
tccggtgagc tcagcagtgc tgtagcgaaa tggctgagct tgaagttctt atcactggct  1140
ggtaaccagc tctccggcca cctacctgac tggatgttct cgttccccct gctccagtgg  1200
cttgatttgt ctagtaataa gtttgtgggt ttcatcccag atggggggtt caatgtcagt  1260
gaagtgctta acggtggagg tggtcagggg actccatcag agagtgtgct tccaccccaa  1320
ttgtttgtgt cagcttctgt ggacacggtg tcatggcagt tggatttggg gtatgatgtt  1380
caggcaacta ctggtataga cctgtctggg aatgagctct gtggggagat accagaaggg  1440
ttggttgaca tgaaggggtt ggagtatttg aacctctcct gtaattactt ggctgggcag  1500
atccctgcgg ggcttggggg catggggagg ttgcatacgc ttgacttctc acataatggg  1560
ctgtcagggg aggtgcctcc tggaattgca gccatgacag tgcttgaggt gcttaacctc  1620
tcctacaata gcctgtctgg gcctttgcca acaacgaagt tcccaggagc attagctgga  1680
aacccaggaa tttgcagtgg gaaagggtgc tctgagaatg caaggactcc agaagggaaa  1740
atggaaggta gcaatcaccg cggttggctt ggtggctggc atggagagaa tggatgggta  1800
tctcttggtg cattttgtat cagcacaatg actagcttct atgtatcatt agcaacctta  1860
ctatgctcct ctaatgcaag aaacttcgtg tttcggcctg tgagggttga atattaacaa  1920
gaggggagat tgcaaaatca ggttgttttg aagttcgagc gactctggtc tgcagctgat  1980
taacaagaaa tatgagcata tgagatggat atcttcagcc aagaggaagt gctgtctctt  2040
ttaatgatca atcaagctct cttgattgtt tcctaatatt cttgatcttg ggatgtgtag  2100
atctagttct aatattccta ctgttataga atgcaatcac ctgctggtgc ttggttgtag  2160
ccctggcgtg tttggaggat tggacaccaa ggatgcacat aatttgaagc gctggtactg  2220
tgaaccactt cagatgtaaa tattttcttt ggtttttagt tctgatctag tttaaaactg  2280
gacatgtatt tagtgttgtt gagctacctt tcgatgttat attatgtcaa tttgctggaa  2340
gatcatttga taacaattgt ctaatccagt ggattagtcg tgt                    2383

SEQ ID NO: 87          moltype = AA  length = 330
FEATURE                Location/Qualifiers
source                 1..330
                       mol_type = protein
                       organism = synthetic construct
SEQUENCE: 87
MLTATPLPHQ LLATFLLVLA SATQPAVPAS TDRAALLAFR ASLSPPSRAA LSSWSGPLSP  60
SWLGVSLHPA TAPAPSVTTP SVAELSLRGL NLTGVIPAAP LALLRRLRTL DLSANALSGE  120
LPCSLPRSLL ALDLSRNALS GAVPTCLPSS LPALRTLNLS ANFLRLPLSP RLSFPARLAA  180
LDLSRNAISG AVPPRIVADP DNSALLLLDL SHNRFSGEIP AGIAAVRSLQ GLFLADNQLS  240
GDIPPGIGNL TYLQVLDLSN NRLSGSVPAG LAGCFQLLYL QLGGNQLSGA LRPELDALAS  300
LKVLDLSNNK ISGEIPLPLA GCRSLEVVDL                                   330

SEQ ID NO: 88          moltype = DNA  length = 2379
FEATURE                Location/Qualifiers
source                 1..2379
                       mol_type = other DNA
                       organism = synthetic construct
SEQUENCE: 88
gccgcggcga cgcccgaggc ctgcaaaacc ctaaccactc aggttctgcc ggccaccgcc  60
accaccacca ccagtccacc accatgctga cagccactcc cctaccccat cagctcctgg  120
ccaccttcct cctcgtcctg gcgtcggcga cccaacctgc agtccctgcc tccaccgacc  180
gcgcagcgct tctcgccttc cgcgcgtccc tgtcgccgcc ctcccgcgcc gcgctatcct  240
cgtggagcgg cccgctctcg ccatcctggc tcggcgtgtc gctccacccc gccacggcgc  300
cagccccttc ggtcaccact ccctccgttg ccgaactctc gctccggggc ctcaacctca  360
cgggcgtgat ccccgcggcg ccgctcgcgc tcctccgacg tctccggacg ctcgacctct  420
ccgccaacgc gctttcggga gagcttccct gctccctccc gcgctcgctc ctcgcgctcg  480
acctctcccg caacgcgctc tcgggggctg tccccacctg cctgccgtcc tcgctccccg  540
cgctccgcac cctcaacctc tccgccaact tcctccgcct cccgctctcc ccgcgtctct  600
ccttccccgc gcgcctcgct gcccttgatc tctcccgcaa cgccatctcc ggcgccgtcc  660
cgccgcggat cgtcgccgac cccgacaact ccgctctcct cctcctcgac ctctcccaca  720
accgcttctc cggcgagatc cccgccggta tcgcagccgt acggagcctg caggggcttt  780
ttctcgcgga caaccagctt tccggggaca ttcctccggg gatagggaac ctgacctatt  840
tgcaggtgct ggatttgtcg aataaccgat tgtccggttc agtgcctgcc ggacttgcag  900
```

-continued

```
gctgcttcca gcttctgtac ctgcagcttg gggtaacca gctctctggg gcactccgtc  960
cggagctcga cgcactagct agtctcaagg ttctagattt gtcgaataac aagatatctg  1020
gggagattcc cctgccgctg gctgggtgca ggtctttgga ggtggtggac gagatctccg  1080
gtgagctcag cagtgctgta gcgaaatggc tgagcttgaa gttcttatca ctggctggta  1140
accagctctc cggccaccta cctgactgga tgttctcgtt cccccctgctc cagtggcttg  1200
atttgtctag taataagttt gtgggtttca tcccagatgg ggggttcaat gtcagtgaag  1260
tgcttaacgg tggaggtggt caggggactc catcagagag tgtgcttcca ccccaattgt  1320
ttgtgtcagc ttctgtggac acggtgtcat ggcagttgga tttggggtat gatgttcagg  1380
caactactgg tatagacctg tctgggaatg agctctgtgg ggagatacca gaagggttgg  1440
ttgacatgaa ggggttggag tatttgaacc tctcctgtaa ttacttggct gggcagatcc  1500
ctgcggggct tgggggcatg gggaggttgc atacgcttga cttctcacat aatgggctgt  1560
caggggaggt gcctcctgga attgcagcca tgacagtgct tgaggtgctt aacctctcct  1620
acaatagcct gtctgggcct ttgccaacaa cgaagttccc aggagcatta gctggaaacc  1680
caggaatttg cagtgggaaa gggtgctctg agaatgcaag gactccagaa gggaaaatgg  1740
aaggtagcaa tcaccgcggt tggcttggtg gctggcatgg agagaatgga tgggtatctc  1800
ttggtgcatt ttgtatcagc acaatgacta gcttctatgt atcattagca accttactat  1860
gctcctctaa tgcaagaaac ttcgtgtttc ggcctgtgag ggttgaatat taacaagagg  1920
ggagattgca aaatcaggtt gttttgaagt tcgagcgact ctggtctgca gctgattaac  1980
aagaaatatg agcatatgag atggatatct tcagccaaga ggaagtgctg tctcttttaa  2040
tgatcaatca agctctcttg attgtttcct aatattcttg atcttgggat gtgtagatct  2100
agttctaata ttcctactgt tatagaatgc aatcacctgc tggtgcttgg ttgtagccct  2160
ggcgtgtttg gaggattgga caccaaggat gcacataatt tgaagcgctg gtactgtgaa  2220
ccacttcaga tgtaaatatt ttctttggtt tttagttctg atctagttta aaactggaca  2280
tgtatttagt gttgttgagc tacctttcga tgttatatta tgtcaatttg ctggaagatc  2340
atttgataac aattgtctaa tccagtggat tagtcgtgt                         2379

SEQ ID NO: 89           moltype = AA  length = 609
FEATURE                 Location/Qualifiers
source                  1..609
                        mol_type = protein
                        organism = synthetic construct
SEQUENCE: 89
MLTATPLPHQ LLATFLLVLA SATQPAVPAS TDRAALLAFR ASLSPPSRAA LSSWSGPLSP  60
SWLGVSLHPA TAPAPSVTTP SVAELSLRGL NLTGVIPAAP LALLRRLRTL DLSANALSGE  120
LPCSLPRSLL ALDLSRNALS GAVPTCLPSS LPALRTLNLS ANFLRLPLSP RLSFPARLAA  180
LDLSRNAISG AVPPRIVADP DNSALLLLDL SHNRFSGEIP AGIAAVRSLQ GLFLADNQLS  240
GDIPPGIGNL TYLQVLDLSN NRLSGSVPAG LAGCFQLLYL QLGGNQLSGA LRPELDALAS  300
LKVLDLSNNK ISGEIPLPLA GCRSLEVVDE ISGELSSAVA KWLSLKFLSL AGNQLSGHLP  360
DWMFSFPLLQ WLDLSSNKFV GFIPDGGFNV SEVLNGGGGQ GTPSESVLPP QLFVSASVDT  420
VSWQLDLGYD VQATTGIDLS GNELCGEIPE GLVDMKGLEY LNLSCNYLAG QIPAGLGGMG  480
RLHTLDFSHN GLSGEVPPGI AAMTVLEVLN LSYNSLSGPL PTTKFPGALA GNPGICSGKG  540
CSENARTPEG KMEGSNHRGW LGGWHGENGW VSLGAFCIST MTSFYVSLAT LLCSSNARNF  600
VFRPVRVEY                                                         609

SEQ ID NO: 90           moltype = DNA  length = 2352
FEATURE                 Location/Qualifiers
source                  1..2352
                        mol_type = other DNA
                        organism = synthetic construct
SEQUENCE: 90
gccgcggcga cgcccgaggc ctgcaaaacc ctaaccactc aggttctgcc ggccaccgcc  60
accaccacca ccagtccacc accatgctga cagccactcc cctaccccat cagctcctgg  120
ccaccttcct cctcgtcctg gcgtcggcga cccaacctgc agtccctgcc tccaccgacc  180
gcgcagcgct tctcgccttc cgcgcgtccc tgtcgccgcc ctcccgcgcc gcgctatcct  240
cgtggagcgg cccgctctcg ccatcctggc tcggcgtgtc gctccacccc gccacggcgc  300
cagccccttc ggtcaccact ccctccgttg ccgaactctc gctccggggc ctcaacctca  360
cgggcgtgat ccccgcggcg ccgctcgcgc tcctccgacg tctccggacg ctcgacctct  420
ccgccaacgc gctttcggga gagcttccct gctccctccc gcgctcgctc ctcgcgctcg  480
acctctcccg caacgcgctc tcgggggctg tccccacctg cctgccgtcc tcgctccccg  540
cgctccgcac cctcaacctc tccgccaact tcctccgcct cccgctctcc ccgcgtctct  600
ccttccccgc gcgcctcgct gcccttgatc tctcccgcaa cgccatctcc ggcgccgtcc  660
cgccgcggat cgtcgccgac cccgacaact ccgctctcct cctcctcgac ctctcccaca  720
accgcttctc cggcgagatc cccgccggta tcgcagccgt acggagcctg caggggcttt  780
ttctcgcgga caaccagctt tccggggaca ttcctccggg gatagggaac ctgacctatt  840
tgcaggtgct ggatttgtcg aataaccgat tgtccggttc agtgcctgcc ggacttgcag  900
gctgcttcca gcttctgtac ctgcagcttg gggtaacca gctctctggg gcactccgtc  960
cggagctcga cgcactagct agtctcaagg ttctagattt gtcgaataac aagatatctg  1020
gggagattcc cctgccgctg gctgggtgca ggggtgagct cagcagtgct gtagcgaaat  1080
ggctgagctt gaagttctta tcactggctg gtaaccagct ctccggccac ctacctgact  1140
ggatgttctc gttcccccctg ctccagtggc ttgatttgtc tagtaataag tttgtgggtt  1200
tcatcccaga tggggggttc aatgtcagtg aagtgcttaa cggtggaggt ggtcagggga  1260
ctccatcaga gagtgtgctt ccaccccaat tgtttgtgtc agcttctgtg gacacggtgt  1320
catggcagtt ggatttgggg tatgatgttc aggcaactac tggtatagac ctgtctggga  1380
atgagctctg tggggagata ccagaagggt tggttgacat gaaggggttg gagtatttga  1440
acctctcctg taattacttg gctgggcaga tccctgcggg gcttgggggc atggggaggt  1500
tgcatacgct tgacttctca cataatgggc tgtcagggga ggtgcctcct ggaattgcag  1560
ccatgacagt gcttgaggtg cttaacctct cctacaatag cctgtctggg cctttgccaa  1620
caacgaagtt cccaggagca ttagctggaa acccaggaat ttgcagtggg aaagggtgct  1680
ctgagaatgc aaggactcca gaagggaaaa tggaaggtag caatcaccgc ggttggcttg  1740
```

```
gtggctggca tggagagaat ggatgggtat ctcttggtgc attttgtatc agcacaatga  1800
ctagcttcta tgtatcatta gcaaccttac tatgctcctc taatgcaaga aacttcgtgt  1860
ttcggcctgt gagggttgaa tattaacaag aggggagatt gcaaaatcag gttgttttga  1920
agttcgagcg actctggtct gcagctgatt aacaagaaat atgagcatat gagatggata  1980
tcttcagcca agaggaagtg ctgtctcttt taatgatcaa tcaagctctc ttgattgttt  2040
cctaatattc ttgatcttgg gatgtgtaga tctagttcta atattcctac tgttatagaa  2100
tgcaatcacc tgctggtgct tggttgtagc cctggcgtgt ttggaggatt ggacaccaag  2160
gatgcacata atttgaagcg ctggtactgt gaaccacttc agatgtaaat attttctttg  2220
gtttttagtt ctgatctagt ttaaaactgg acatgtattt agtgttgttg agctaccttt  2280
cgatgttata ttatgtcaat ttgctggaag atcatttgat aacaattgtc taatccagtg  2340
gattagtcgt gt                                                      2352

SEQ ID NO: 91          moltype = AA  length = 600
FEATURE                Location/Qualifiers
source                 1..600
                       mol_type = protein
                       organism = synthetic construct
SEQUENCE: 91
MLTATPLPHQ LLATFLLVLA SATQPAVPAS TDRAALLAFR ASLSPPSRAA LSSWSGPLSP  60
SWLGVSLHPA TAPAPSVTTP SVAELSLRGL NLTGVIPAAP LALLRRLRTL DLSANALSGE  120
LPCSLPRSLL ALDLSRNALS GAVPTCLPSS LPALRTLNLS ANFLRLPLSP RLSFPARLAA  180
LDLSRNAISG AVPPRIVADP DNSALLLLDL SHNRFSGEIP AGIAAVRSLQ GLFLADNQLS  240
GDIPPGIGNL TYLQVLDLSN NRLSGSVPAG LAGCFQLLYL QLGGNQLSGA LRPELDALAS  300
LKVLDLSNNK ISGEIPLPLA GCRGELSSAV AKWLSLKFLS LAGNQLSGHL PDWMFSFPLL  360
QWLDLSSNKF VGFIPDGGFN VSEVLNGGGG QGTPSESVLP PQLFVSASVD TVSWQLDLGY  420
DVQATTGIDL SGNELCGEIP EGLVDMKGLE YLNLSCNYLA GQIPAGLGGM GRLHTLDFSH  480
NGLSGEVPPG IAAMTVLEVL NLSYNSLSGP LPTTKFPGAL AGNPGICSGK GCSENARTPE  540
GKMEGSNHRG WLGGWHGENG WVSLGAFCIS TMTSFYVSLA TLLCSSNARN FVFRPVRVEY  600

SEQ ID NO: 92          moltype = DNA  length = 2389
FEATURE                Location/Qualifiers
source                 1..2389
                       mol_type = other DNA
                       organism = synthetic construct
SEQUENCE: 92
gccgcggcga cgcccgaggc ctgcaaaacc ctaaccactc aggttctgcc ggccaccgcc  60
accaccacca ccagtccacc accatgctga cagccactcc cctaccccat cagctcctgg  120
ccaccttcct cctcgtcctg gcgtcggcga cccaacctgc agtccctgcc tccaccgacc  180
gcgcagcgct tctcgccttc cgcgcgtccc tgtcgccgcc ctcccgcgcc gcgctatcct  240
cgtggagcgg cccgctctcg ccatcctggc tcggcgtgtc gctccacccc gccacggcgc  300
cagccccttc ggtcaccact ccctccgttg ccgaactctc gctccggggc ctcaacctca  360
cgggcgtgat ccccgcggcg ccgctcgcgc tcctccgacg tctccggacg ctcgacctct  420
ccgccaacgc gctttcggga gagcttccct gctccctccc gcgctcgctc ctcgcgctcg  480
acctctcccg caacgcgctc tcgggggctg tccccacctg cctgccgtcc tcgctccccg  540
cgctccgcac cctcaacctc tccgccaact tcctccgcct cccgctctcc ccgcgtctct  600
ccttccccgc gcgcctcgct gcccttgatc tctcccgcaa cgccatctcc ggcgccgtcc  660
cgccgcggat cgtcgccgac cccgacaact ccgctctcct cctcctcgac ctctcccaca  720
accgcttctc cggcgagatc cccgccggta tcgcagccgt acggagcctg caggggcttt  780
ttctcgcgga caaccagctt tccggggaca ttcctccggg gatagggaac ctgacctatt  840
tgcaggtgct ggatttgtcg aataaccgat tgtccggttc agtgcctgcc ggacttgcag  900
gctgcttcca gcttctgtac ctgcagcttg gggtaacca gctctctggg gcactccgtc  960
cggagctcga cgcactagct agtctcaagg ttctagattt gtcgaataac aagatatctg  1020
gggagattcc cctgccgctg gctgggtgca ggtctttgga ggtggtggac ttgtggaaat  1080
gagatctccg gtgagctcag cagtgctgta gcgaaatggc tgagcttgaa gttcttatca  1140
ctggctggta accagctctc cggccaccta cctgactgga tgttctcgtt cccccctgctc  1200
cagtggcttg atttgtctag taataagttt gtgggtttca tcccagatgg ggggttcaat  1260
gtcagtgaag tgcttaacgg tggaggtggt caggggactc catcagagag tgtgcttcca  1320
ccccaattgt ttgtgtcagc ttctgtggac acggtgtcat ggcagttgga tttggggtat  1380
gatgttcagg caactactgg tatagacctg tctgggaatg agctctgtgg ggagatacca  1440
gaagggttgg ttgacatgaa ggggttggag tatttgaacc tctcctgtaa ttacttggct  1500
gggcagatcc ctgcggggct tgggggcatg gggaggttgc atacgcttga cttctcacat  1560
aatgggctgt caggggaggt gcctcctgga attgcagcca tgacagtgct tgaggtgctt  1620
aacctctcct acaatagcct gtctgggcct ttgccaacaa cgaagttccc aggagcatta  1680
gctggaaacc caggaatttg cagtgggaaa gggtgctctg agaatgcaag gactccagaa  1740
gggaaaatgg aaggtagcaa tcaccgcggt tggcttggtg gctggcatgg agagaatgga  1800
tgggtatctc ttggtgcatt ttgtatcagc acaatgacta gcttctatgt atcattagca  1860
accttactat gctcctctaa tgcaagaaac ttcgtgtttc ggcctgtgag ggttgaatat  1920
taacaagagg ggagattgca aaatcaggtt gttttgaagt tcgagcgact ctggtctgca  1980
gctgattaac aagaaatatg agcatatgag atggatatct tcagccaaga ggaagtgctg  2040
tctcttttaa tgatcaatca agctctcttg attgtttcct aatattcttg atcttgggat  2100
gtgtagatct agttctaata ttcctactgt tatagaatgc aatcacctgc tggtgcttgg  2160
ttgtagccct ggcgtgtttg gaggattgga caccaaggat gcacataatt tgaagcgctg  2220
gtactgtgaa ccacttcaga tgtaaatatt ttctttggtt tttagttctg atctagttta  2280
aaactggaca tgtatttagt gttgttgagc tacctttcga tgttatatta tgtcaatttg  2340
ctggaagatc atttgataac aattgtctaa tccagtggat tagtcgtgt              2389

SEQ ID NO: 93          moltype = AA  length = 332
FEATURE                Location/Qualifiers
source                 1..332
```

```
                      mol_type = protein
                      organism = synthetic construct
SEQUENCE: 93
MLTATPLPHQ LLATFLLVLA SATQPAVPAS TDRAALLAFR ASLSPPSRAA LSSWSGPLSP  60
SWLGVSLHPA TAPAPSVTTP SVAELSLRGL NLTGVIPAAP LALLRRLRTL DLSANALSGE  120
LPCSLPRSLL ALDLSRNALS GAVPTCLPSS LPALRTLNLS ANFLRLPLSP RLSFPARLAA  180
LDLSRNAISG AVPPRIVADP DNSALLLLDL SHNRFSGEIP AGIAAVRSLQ GLFLADNQLS  240
GDIPPGIGNL TYLQVLDLSN NRLSGSVPAG LAGCFQLLYL QLGGNQLSGA LRPELDALAS  300
LKVLDLSNNK ISGEIPLPLA GCRSLEVVDL WK                                332

SEQ ID NO: 94         moltype = DNA  length = 2367
FEATURE               Location/Qualifiers
source                1..2367
                      mol_type = other DNA
                      organism = synthetic construct
SEQUENCE: 94
gccgcggcga cgcccgaggc ctgcaaaacc ctaaccactc aggttctgcc ggccaccgcc  60
accaccacca ccagtccacc accatgctga cagccactcc cctaccccat cagctcctgg  120
ccaccttcct cctcgtcctg gcgtcggcga cccaacctgc agtccctgcc tccaccgacc  180
gcgcagcgct tctcgccttc cgcgcgtccc tgtcgccgcc ctcccgcgcc gcgctatcct  240
cgtggagcgg cccgctctcg ccatcctggc tcggcgtgtc gctccacccc gccacggcgc  300
cagcccctte ggtcaccact ccctccgttg ccgaactctc gctccggggc ctcaacctca  360
cgggcgtgat ccccgcggcg ccgctcgcgc tcctccgacg tctccggacg ctcgacctct  420
ccgccaacgc gctttcggga gagcttccct gctccctccc gcgctcgctc ctcgcgctcg  480
acctctcccg caacgcgctc tcgggggctg tccccacctg cctgccgtcc tcgctccccg  540
cgctccgcac cctcaacctc tccgccaact tcctccgcct cccgctctcc ccgcgtctct  600
ccttccccgc gcgcctcgct gcccttgatc tctcccgcaa cgccatctcc ggcgccgtcc  660
cgccgcggat cgtcgccgac cccgacaact ccgctctcct cctcctcgac ctctcccaca  720
accgcttctc cggcgagatc cccgccggta tcgcagccgt acggagcctg caggggcttt  780
ttctcgcgga caaccagctt tccggggaca ttcctccggg gatagggaac ctgacctatt  840
tgcaggtgct ggatttgtcg aataaccgat tgtccggttc agtgcctgcc ggacttgcag  900
gctgcttcca gcttctgtac ctgcagcttg gggtaacca gctctctggg gcactccgtc  960
cggagctcga cgcactagct agtctcaagg ttctagattt gtcgaataac aagatatctg  1020
gggagattcc cctgccgctg gctgggtgca ggtctttgga gatctccggt gagctcagca  1080
gtgctgtagc gaaatggctg agcttgaagt tcttatcact ggctggtaac cagctctccg  1140
gccacctacc tgactggatg ttctcgttcc ccctgctcca gtggcttgat ttgtctagta  1200
ataagtttgt gggtttcatc ccagatgggg ggttcaatgt cagtgaagtg cttaacggtg  1260
gaggtggtca ggggactcca tcagagagtg tgcttccacc ccaattgttt gtgtcagctt  1320
ctgtggacac ggtgtcatgg cagttggatt tggggtatga tgttcaggca actactggta  1380
tagacctgtc tgggaatgag ctctgtgggg agataccaga agggttggtt gacatgaagg  1440
ggttggagta tttgaacctc tcctgtaatt acttggctgg gcagatccct gcggggcttg  1500
ggggcatggg gaggttgcat acgcttgact tctcacataa tgggctgtca ggggaggtgc  1560
ctcctggaat tgcagccatg acagtgcttg aggtgcttaa cctctcctac aatagcctgt  1620
ctgggccttt gccaacaacg aagttcccag gagcattagc tggaaaccca ggaatttgca  1680
gtgggaaagg gtgctctgag aatgcaagga ctccagaagg gaaaatggaa ggtagcaatc  1740
accgcggttg gcttggtggc tggcatggag agaatggatg ggtatctctt ggtgcatttt  1800
gtatcagcac aatgactagc ttctatgtat cattagcaac cttactatgc tcctctaatg  1860
caagaaactt cgtgtttcgg cctgtgaggg ttgaatatta acaagagggg agattgcaaa  1920
atcaggttgt tttgaagttc gagcgactct ggtctgcagc tgattaacaa gaaatatgag  1980
catatgagat ggatatcttc agccaagagg aagtgctgtc tcttttaatg atcaatcaag  2040
ctctcttgat tgtttcctaa tattcttgat cttgggatgt gtagatctag ttctaatatt  2100
cctactgtta tagaatgcaa tcacctgctg gtgcttggtt gtagccctgg cgtgtttgga  2160
ggattggaca ccaaggatgc acataatttg aagcgctggt actgtgaacc acttcagatg  2220
taaatatttt ctttggtttt tagttctgat ctagtttaaa actggacatg tatttagtgt  2280
tgttgagcta cctttcgatg ttatattatg tcaatttgct ggaagatcat ttgataacaa  2340
ttgtctaatc cagtggatta gtcgtgt                                      2367

SEQ ID NO: 95         moltype = AA  length = 605
FEATURE               Location/Qualifiers
source                1..605
                      mol_type = protein
                      organism = synthetic construct
SEQUENCE: 95
MLTATPLPHQ LLATFLLVLA SATQPAVPAS TDRAALLAFR ASLSPPSRAA LSSWSGPLSP  60
SWLGVSLHPA TAPAPSVTTP SVAELSLRGL NLTGVIPAAP LALLRRLRTL DLSANALSGE  120
LPCSLPRSLL ALDLSRNALS GAVPTCLPSS LPALRTLNLS ANFLRLPLSP RLSFPARLAA  180
LDLSRNAISG AVPPRIVADP DNSALLLLDL SHNRFSGEIP AGIAAVRSLQ GLFLADNQLS  240
GDIPPGIGNL TYLQVLDLSN NRLSGSVPAG LAGCFQLLYL QLGGNQLSGA LRPELDALAS  300
LKVLDLSNNK ISGEIPLPLA GCRSLEISGE LSSAVAKWLS LKFLSLAGNQ LSGHLPDWMF  360
SFPLLQWLDL SSNKFVGFIP DGGFNVSEVL NGGGGQGTPS ESVLPPQLFV SASVDTVSWQ  420
LDLGYDVQAT TGIDLSGNEL CGEIPEGLVD MKGLEYLNLS CNYLAGQIPA GLGGMGRLHT  480
LDFSHNGLSG EVPPGIAAMT VLEVLNLSYN SLSGPLPTTK FPGALAGNPG ICSGKGCSEN  540
ARTPEGKMEG SNHRGWLGGW HGENGWVSLG AFCISTMTSF YVSLATLLCS SNARNFVFRP  600
VRVEY                                                              605

SEQ ID NO: 96         moltype = DNA  length = 2382
FEATURE               Location/Qualifiers
source                1..2382
                      mol_type = other DNA
```

```
                        organism = synthetic construct
SEQUENCE: 96
gccgcggcga cgcccgaggc ctgcaaaacc ctaaccactc aggttctgcc ggccaccgcc  60
accaccacca ccagtccacc accatgctga cagccactcc cctaccccat cagctcctgg  120
ccaccttcct cctcgtcctg gcgtcggcga cccaacctgc agtccctgcc tccaccgacc  180
gcgcagcgct tctcgccttc cgcgcgtccc tgtcgccgcc ctcccgcgcc gcgctatcct  240
cgtggagcgg cccgctctcg ccatcctggc tcggcgtgtc gctccacccc gccacggcgc  300
cagccccttc ggtcaccact ccctccgttg ccgaactctc gctccggggc ctcaacctca  360
cgggcgtgat ccccgcggcg ccgctcgcgc tcctccgacg tctccggacg ctcgacctct  420
ccgccaacgc gctttcggga gagcttccct gctccctccc gcgctcgctc ctcgcgctcg  480
acctctcccg caacgcgctc tcgggggctg tccccacctg cctgccgtcc tcgctccccg  540
cgctccgcac cctcaacctc tccgccaact tcctccgcct cccgctctcc ccgcgtctct  600
ccttccccgc gcgcctcgct gcccttgatc tctcccgcaa cgccatctcc ggcgccgtcc  660
cgccgcggat cgtcgccgac cccgacaact ccgctctcct cctcctcgac ctctcccaca  720
accgcttctc cggcgagatc cccgccggta tcgcagccgt acggagcctg caggggcttt  780
ttctcgcgga caaccagctt tccggggaca ttcctccggg gatagggaac ctgacctatt  840
tgcaggtgct ggatttgtcg aataaccgat tgtccggttc agtgcctgcc ggacttgcag  900
gctgcttcca gcttctgtac ctgcagcttg gggtaacca gctctctggg gcactccgtc  960
cggagctcga cgcactagct agtctcaagg ttctagattt gtcgaataac aagatatctg  1020
gggagattcc cctgccgctg gctgggtgca ggtctttgga ggtggtggac tatgagatct  1080
ccggtgagct cagcagtgct gtagcgaaat ggctgagctt gaagttctta tcactggctg  1140
gtaaccagct ctccggccac ctacctgact ggatgttctc gttccccctg ctccagtggc  1200
ttgatttgtc tagtaataag tttgtgggtt tcatcccaga tggggggttc aatgtcagtg  1260
aagtgcttaa cggtggaggt ggtcagggga ctccatcaga gagtgtgctt ccaccccaat  1320
tgtttgtgtc agcttctgtg gacacggtgt catggcagtt ggatttgggg tatgatgttc  1380
aggcaactac tggtatagac ctgtctggga atgagctctg tggggagata ccagaagggt  1440
tggttgacat gaaggggttg gagtatttga acctctcctg taattacttg gctgggcaga  1500
tccctgcggg gcttgggggc atggggaggt tgcatacgct tgacttctca cataatgggc  1560
tgtcagggga ggtgcctcct ggaattgcag ccatgacagt gcttgaggtg cttaacctct  1620
cctacaatag cctgtctggg cctttgccaa caacgaagtt cccaggagca ttagctggaa  1680
acccaggaat ttgcagtggg aaagggtgct ctgagaatgc aaggactcca gaagggaaaa  1740
tggaaggtag caatcaccgc ggttggcttg gtggctggca tggagagaat ggatgggtat  1800
ctcttggtgc attttgtatc agcacaatga ctagcttcta tgtatcatta gcaaccttac  1860
tatgctcctc taatgcaaga aacttcgtgt ttcggcctgt gagggttgaa tattaacaag  1920
aggggagatt gcaaaatcag gttgttttga agttcgagcg actctggtct gcagctgatt  1980
aacaagaaat atgagcatat gagatggata tcttcagcca agaggaagtg ctgtctcttt  2040
taatgatcaa tcaagctctc ttgattgttt cctaatattc ttgatcttgg gatgtgtaga  2100
tctagttcta atattcctac tgttatagaa tgcaatcacc tgctggtgct tggttgtagc  2160
cctggcgtgt ttggaggatt ggacaccaag gatgcacata atttgaagcg ctggtactgt  2220
gaaccacttc agatgtaaat atttctttg gtttttagtt ctgatctagt ttaaaactgg  2280
acatgtattt agtgttgttg agctaccttt cgatgttata ttatgtcaat ttgctggaag  2340
atcatttgat aacaattgtc taatccagtg gattagtcgt gt                    2382

SEQ ID NO: 97           moltype = AA  length = 610
FEATURE                 Location/Qualifiers
source                  1..610
                        mol_type = protein
                        organism = synthetic construct
SEQUENCE: 97
MLTATPLPHQ LLATFLLVLA SATQPAVPAS TDRAALLAFR ASLSPPSRAA LSSWSGPLSP  60
SWLGVSLHPA TAPAPSVTTP SVAELSLRGL NLTGVIPAAP LALLRRLRTL DLSANALSGE  120
LPCSLPRSLL ALDLSRNALS GAVPTCLPSS LPALRTLNLS ANFLRLPLSP RLSFPARLAA  180
LDLSRNAISG AVPPRIVADP DNSALLLLDL SHNRFSGEIP AGIAAVRSLQ GLFLADNQLS  240
GDIPPGIGNL TYLQVLDLSN NRLSGSVPAG LAGCFQLLYL QLGGNQLSGA LRPELDALAS  300
LKVLDLSNNK ISGEIPLPLA GCRSLEVVDY EISGELSSAV AKWLSLKFLS LAGNQLSGHL  360
PDWMFSFPLL QWLDLSSNKF VGFIPDGGFN VSEVLNGGGG QGTPSESVLP PQLFVSASVD  420
TVSWQLDLGY DVQATTGIDL SGNELCGEIP EGLVDMKGLE YLNLSCNYLA GQIPAGLGGM  480
GRLHTLDFSH NGLSGEVPPG IAAMTVLEVL NLSYNSLSGP LPTTKFPGAL AGNPGICSGK  540
GCSENARTPE GKMEGSNHRG WLGGWHGENG WVSLGAFCIS TMTSFYVSLA TLLCSSNARN  600
FVFRPVRVEY                                                        610

SEQ ID NO: 98           moltype = DNA  length = 2387
FEATURE                 Location/Qualifiers
source                  1..2387
                        mol_type = other DNA
                        organism = synthetic construct
SEQUENCE: 98
gccgcggcga cgcccgaggc ctgcaaaacc ctaaccactc aggttctgcc ggccaccgcc  60
accaccacca ccagtccacc accatgctga cagccactcc cctaccccat cagctcctgg  120
ccaccttcct cctcgtcctg gcgtcggcga cccaacctgc agtccctgcc tccaccgacc  180
gcgcagcgct tctcgccttc cgcgcgtccc tgtcgccgcc ctcccgcgcc gcgctatcct  240
cgtggagcgg cccgctctcg ccatcctggc tcggcgtgtc gctccacccc gccacggcgc  300
cagccccttc ggtcaccact ccctccgttg ccgaactctc gctccggggc ctcaacctca  360
cgggcgtgat ccccgcggcg ccgctcgcgc tcctccgacg tctccggacg ctcgacctct  420
ccgccaacgc gctttcggga gagcttccct gctccctccc gcgctcgctc ctcgcgctcg  480
acctctcccg caacgcgctc tcgggggctg tccccacctg cctgccgtcc tcgctccccg  540
cgctccgcac cctcaacctc tccgccaact tcctccgcct cccgctctcc ccgcgtctct  600
ccttccccgc gcgcctcgct gcccttgatc tctcccgcaa cgccatctcc ggcgccgtcc  660
cgccgcggat cgtcgccgac cccgacaact ccgctctcct cctcctcgac ctctcccaca  720
```

-continued

```
accgcttctc cggcgagatc cccgccggta tcgcagccgt acggagcctg caggggcttt  780
ttctcgcgga caaccagctt tccggggaca ttcctccggg gatagggaac ctgacctatt  840
tgcaggtgct ggatttgtcg aataaccgat tgtccggttc agtgcctgcc ggacttgcag  900
gctgcttcca gcttctgtac ctgcagcttg ggggtaacca gctctctggg gcactccgtc  960
cggagctcga cgcactagct agtctcaagg ttctagattt gtcgaataac aagatatctg  1020
gggagattcc cctgccgctg gctgggtgca ggtctttgga ggtggtggac ttggaaatga  1080
gatctccggt gagctcagca gtgctgtagc gaaatggctg agcttgaagt tcttatcact  1140
ggctggtaac cagctctccg gccacctacc tgactggatg ttctcgttcc ccctgctcca  1200
gtggcttgat ttgtctagta ataagtttgt gggtttcatc ccagatgggg ggttcaatgt  1260
cagtgaagtg cttaacggtg gaggtggtca ggggactcca tcagagagtg tgcttccacc  1320
ccaattgttt gtgtcagctt ctgtggacac ggtgtcatgg cagttggatt tggggtatga  1380
tgttcaggca actactggta tagacctgtc tgggaatgag ctctgtgggg agataccaga  1440
agggttggtt gacatgaagg ggttggagta tttgaacctc tcctgtaatt acttggctgg  1500
gcagatccct gcggggcttg gggcatggg  gaggttgcat acgcttgact tctcacataa  1560
tgggctgtca ggggaggtgc ctcctggaat tgcagccatg acagtgcttg aggtgcttaa  1620
cctctcctac aatagcctgt ctgggccttt gccaacaacg aagttcccag gagcattagc  1680
tggaaaccca ggaatttgca gtgggaaagg gtgctctgag aatgcaagga ctccagaagg  1740
gaaaatggaa ggtagcaatc accgcggttg gcttggtggc tggcatggag agaatggatg  1800
ggtatctctt ggtgcatttt gtatcagcac aatgactagc ttctatgtat cattagcaac  1860
cttactatgc tcctctaatg caagaaactt cgtgtttcgg cctgtgaggg ttgaatatta  1920
acaagagggg agattgcaaa atcaggttgt tttgaagttc gagcgactct ggtctgcagc  1980
tgattaacaa gaaatatgag catatgagat ggatatcttc agccaagagg aagtgctgtc  2040
tcttttaatg atcaatcaag ctctcttgat tgtttcctaa tattcttgat cttgggatgt  2100
gtagatctag ttctaatatt cctactgtta tagaatgcaa tcacctgctg gtgcttggtt  2160
gtagccctgg cgtgtttgga ggattggaca ccaaggatgc acataatttg aagcgctggt  2220
actgtgaacc acttcagatg taaatatttt ctttggtttt tagttctgat ctagtttaaa  2280
actggacatg tatttagtgt tgttgagcta cctttcgatg ttatattatg tcaatttgct  2340
ggaagatcat ttgataacaa ttgtctaatc cagtggatta gtcgtgt                2387

SEQ ID NO: 99          moltype = AA  length = 341
FEATURE                Location/Qualifiers
source                 1..341
                       mol_type = protein
                       organism = synthetic construct
SEQUENCE: 99
MLTATPLPHQ LLATFLLVLA SATQPAVPAS TDRAALLAFR ASLSPPSRAA LSSWSGPLSP  60
SWLGVSLHPA TAPAPSVTTP SVAELSLRGL NLTGVIPAAP LALLRRLRTL DLSANALSGE  120
LPCSLPRSLL ALDLSRNALS GAVPTCLPSS LPALRTLNLS ANFLRLPLSP RLSFPARLAA  180
LDLSRNAISG AVPPRIVADP DNSALLLLDL SHNRFSGEIP AGIAAVRSLQ GLFLADNQLS  240
GDIPPGIGNL TYLQVLDLSN NRLSGSVPAG LAGCFQLLYL QLGGNQLSGA LRPELDALAS  300
LKVLDLSNNK ISGEIPLPLA GCRSLEVVDL EMRSPVSSAV L                       341

SEQ ID NO: 100         moltype = DNA  length = 24
FEATURE                Location/Qualifiers
source                 1..24
                       mol_type = genomic DNA
                       organism = Zea mays
SEQUENCE: 100
ggtggacttg tcaggaaatg agat                                          24

SEQ ID NO: 101         moltype = AA  length = 8
FEATURE                Location/Qualifiers
source                 1..8
                       mol_type = protein
                       organism = Zea mays
SEQUENCE: 101
VDLSGNEI                                                            8

SEQ ID NO: 102         moltype = DNA  length = 12
FEATURE                Location/Qualifiers
source                 1..12
                       mol_type = genomic DNA
                       organism = Zea mays
SEQUENCE: 102
ttgtcaggaa at                                                       12

SEQ ID NO: 103         moltype = AA  length = 4
FEATURE                Location/Qualifiers
source                 1..4
                       mol_type = protein
                       organism = Zea mays
SEQUENCE: 103
LSGN                                                                4

SEQ ID NO: 104         moltype = DNA  length = 39
FEATURE                Location/Qualifiers
source                 1..39
                       mol_type = genomic DNA
                       organism = Zea mays
```

-continued

```
SEQUENCE: 104
tctttggagg tggtggactt gtcaggaaat gagatctcc                        39

SEQ ID NO: 105         moltype = AA  length = 13
FEATURE                Location/Qualifiers
source                 1..13
                       mol_type = protein
                       organism = Zea mays
SEQUENCE: 105
SLEVVDLSGN EIS                                                    13

SEQ ID NO: 106         moltype = DNA  length = 24
FEATURE                Location/Qualifiers
source                 1..24
                       mol_type = genomic DNA
                       organism = Zea mays
SEQUENCE: 106
ggtggtggac ttgtcaggaa atga                                        24

SEQ ID NO: 107         moltype = AA  length = 8
FEATURE                Location/Qualifiers
source                 1..8
                       mol_type = protein
                       organism = Zea mays
SEQUENCE: 107
VVDLSGNE                                                          8
```

What is claimed is:

1. A corn plant or plant part thereof comprising at least one mutation in an endogenous FASCIATED EAR2 (FEA2) gene that encodes a FEA2 polypeptide, wherein the endogenous FEA2 gene (a) comprises a nucleotide sequence having at least 90% sequence identity to SEQ ID NO:72 or SEQ ID NO:73, (b) comprises a region having at least 90% sequence identity to any one of the nucleotide sequences of SEQ ID NOs: 75-77, (c) encodes an amino acid sequence having at least 90% sequence identity to SEQ ID NO:74, and/or (d) encodes a polypeptide comprising a region having at least 90% sequence identity to any one of the amino acid sequences of SEQ ID NOs: 78-80; the at least one mutation is an insertion located in a region comprising a sequence having at least 90% sequence identity to any one of SEQ ID NOs: 75-77; the at least one mutation results in a premature stop codon; and the at least one mutation results in a mutated FEA2 gene with a nucleotide sequence having at least 90% sequence identity to SEQ ID NO:84 and/or encoding a mutated FEA2 polypeptide having at least 90% sequence identity to SEQ ID NO:85.

2. The corn plant or plant part thereof of claim 1, wherein the at least one mutation results in a mutated FEA2 polypeptide having an altered ability to complex with other polypeptides, an altered ability to transit the plasma membrane, and/or locate from the endoplasmic reticulum to the plasma membrane.

3. The corn plant or plant part thereof of claim 1, wherein the corn plant comprising the at least one mutation exhibits increased yield as compared to a control plant devoid of the at least one mutation.

4. The corn plant or plant part thereof of claim 3, wherein the corn plant exhibits a phenotype of increased kernel row number (KRN).

5. A method for producing a corn plant or plant part thereof comprising at least one cell having a mutated endogenous FASCIATED EAR2 (FEA2) gene, the method comprising:

contacting a target site in an endogenous FEA2 gene in the corn plant or plant part with a nuclease comprising a cleavage domain and a nucleic acid binding domain, wherein the nucleic acid binding domain binds to a target site in the endogenous FEA2 gene, wherein the endogenous FEA2 gene (a) comprises a nucleotide sequence having at least 90% sequence identity to the sequence of SEQ ID NO:72 or SEQ ID NO:73;

(b) encodes an amino acid sequence having at least 90% sequence identity to the sequence of SEQ ID NO:74;

(c) comprises a region having at least 90% sequence identity to the nucleotide sequence of any one of SEQ ID NOs: 75-77; and/or (d) encodes a region of a polypeptide having at least 90% sequence identity to any one of the amino acid sequences of SEQ ID NOs: 78-80;

the target site is located in a nucleotide sequence having at least 90% sequence identity to any one of SEQ ID NOs: 75-77 or encoding any one of the polypeptide sequences of SEQ ID NOs: 78-80; the mutation in the endogenous FEA2 gene results in a premature stop codon, and the mutation results in a mutated FEA2 gene with a nucleotide sequence having at least 90% sequence identity to SEQ ID NO:84 and/or encoding a mutated FEA2 polypeptide having at least 90% sequence identity to SEQ ID NO:85, thereby producing the corn plant or plant part thereof comprising at least one cell having a mutation in the endogenous FEA2 gene.

6. The method of claim 5, wherein the mutation results in a mutated FEA2 polypeptide having an altered ability to complex with other polypeptides, an altered ability to transit the plasma membrane, and/or locate from the endoplasmic reticulum to the plasma membrane.

7. A corn plant or part thereof comprising a nucleic acid comprising a sequence having at least 90% sequence identity to SEQ ID NO: 84 and/or encoding a mutated FEA2 polypeptide having at least 90% sequence identity to any one of SEQ ID NO: 85, wherein the nucleic acid comprises at least one mutation.

8. A corn plant or part thereof comprising a truncated corn FASCIATED EAR2 (FEA2) polypeptide comprising the polypeptide sequence of SEQ ID NO: 85.

* * * * *